(12) United States Patent
Mousa et al.

(10) Patent No.: US 10,201,616 B2
(45) Date of Patent: Feb. 12, 2019

(54) NON-CLEAVABLE POLYMER CONJUGATED WITH αVβ3 INTEGRIN THYROID ANTAGONISTS

(71) Applicant: NANOPHARMACEUTICALS, LLC, Rensselaer, NY (US)

(72) Inventors: Shaker A. Mousa, Wynantskill, NY (US); Mehdi Rajabi, Albany, NY (US)

(73) Assignee: NANOPHARMACEUTICALS, LLC, Rensselaer, NY (US)

( * ) Notice: Subject to any disclaimer, the term of this patent is extended or adjusted under 35 U.S.C. 154(b) by 0 days.

(21) Appl. No.: 15/616,637

(22) Filed: Jun. 7, 2017

(65) Prior Publication Data

US 2017/0348425 A1    Dec. 7, 2017

Related U.S. Application Data

(60) Provisional application No. 62/346,659, filed on Jun. 7, 2016.

(51) Int. Cl.
| | | |
|---|---|---|
| *A61K 31/19* | (2006.01) | |
| *A61K 47/60* | (2017.01) | |
| *A61K 47/54* | (2017.01) | |
| *A61K 47/61* | (2017.01) | |

(52) U.S. Cl.
CPC .............. *A61K 47/60* (2017.08); *A61K 31/19* (2013.01); *A61K 47/545* (2017.08); *A61K 47/61* (2017.08)

(58) Field of Classification Search
None
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,208,483 A | 6/1980 | Lee |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,515,100 B2 | 2/2003 | Harris |
| 6,534,676 B2 | 3/2003 | Morkin et al. |
| 6,596,712 B2 | 7/2003 | Zasloff et al. |
| 6,677,473 B1 | 1/2004 | Madison et al. |

(Continued)

FOREIGN PATENT DOCUMENTS

| | | |
|---|---|---|
| CA | 2673133 A1 | 11/2008 |
| CN | 1126589 | 7/1996 |

(Continued)

OTHER PUBLICATIONS

Veronese, Biomaterials 22 (2001) 405-417.*
A.D.A.M. Medical Encyclopedia, www.ncbi.nlm.nih.gov/pubmedhealth/PMH0001308/ , downloaded Jul. 12, 2012. 6 pages.
Abdollahi et al., "Inhibition of αvβ3 Integrin Survival Signaling Enhances Antiangiogenic and Antitumor Effects of Radiotherapy", Clin. Cancer Research., 11(17):6270-6279 (2005) 10 pages.
Albert et al., "Integrin αvβ3 Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.

(Continued)

*Primary Examiner* — Layla D Berry
(74) *Attorney, Agent, or Firm* — Schmeiser, Olsen & Watts, LLP

(57) ABSTRACT

Chemical compositions and methods of synthesis thereof. The compositions disclosed and described herein are directed toward and classified as anti-angiogenic thyrointegrin antagonists, which may be capable of reacting with one or more cell surface receptors of the integrin αvβ3 receptor family. Anti-angiogenic thyrointegrin antagonists or derivatives thereof are conjugated via a non-cleavable linker having an amine, diamine or triazole linkage to polymers of Polyethylene Glycol, cyclodextrin, chitosan, alginic acid or hyaluronic acid, forming a single chemical entity. Utility of the compositions disclosed may treat angiogenesis-mediated disorders such as Cancer (Solid tumors and Liquid tumors), ocular disorders (Diabetic Retinopathy and Age-related Macular Degeneration), inflammatory disorders (arthritis, osteoarthritis), atherosclerosis, lesions, and dermatology (Rosacea, Psoriasis, skin cancer) and diseases mediated or dependent upon the generation of new blood cells via angiogenesis to persist and the treatment thereof or dependent on antagonizing the formation of new blood vessels to slow or eliminate angiogenic pathways.

23 Claims, 52 Drawing Sheets

(56) References Cited

U.S. PATENT DOCUMENTS

| | | |
|---|---|---|
| 6,740,680 B1 | 5/2004 | Danforth, Jr. et al. |
| 6,818,620 B2 | 11/2004 | Bhatnagar |
| 6,821,947 B2 | 11/2004 | Renato |
| 6,936,274 B2 | 8/2005 | Hanshew, Jr. |
| 7,166,155 B2 | 1/2007 | Takeshi |
| 7,358,085 B2 | 4/2008 | Zhang et al. |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,515,451 B2 | 8/2013 | Mousa et al. |
| 8,668,926 B1 | 8/2014 | Davis et al. |
| 8,802,240 B2 | 8/2014 | Davis et al. |
| 9,180,107 B2 | 11/2015 | Mousa et al. |
| 9,198,887 B2 | 12/2015 | Mousa et al. |
| 9,220,788 B2 | 12/2015 | Davis et al. |
| 9,272,049 B2 | 3/2016 | Alexander-Bridges et al. |
| 9,289,395 B2 | 3/2016 | Davis et al. |
| 9,498,536 B2 | 11/2016 | Mousa et al. |
| 9,539,345 B2 | 1/2017 | Kim et al. |
| 9,579,300 B2 | 2/2017 | Mousa et al. |
| 9,750,709 B2 | 9/2017 | Mousa et al. |
| 9,839,614 B2 | 12/2017 | Mousa et al. |
| 2001/0021763 A1 | 9/2001 | Harris |
| 2001/0023254 A1 | 9/2001 | McElroy |
| 2001/0046521 A1 | 11/2001 | Zasloff et al. |
| 2002/0049247 A1 | 4/2002 | Chen |
| 2002/0013205 A1 | 9/2002 | Faour |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0104999 A1 | 6/2003 | Izzo |
| 2003/0138557 A1 | 7/2003 | Allison |
| 2003/0143727 A1 | 7/2003 | Chang |
| 2003/0157098 A1 | 8/2003 | Laug |
| 2003/0162758 A1 | 8/2003 | Schwartz et al. |
| 2003/0165576 A1 | 9/2003 | Fuji et al. |
| 2004/0013728 A1 | 1/2004 | Oh et al. |
| 2004/0033259 A1 | 2/2004 | Hanshew, Jr. et al. |
| 2004/0208844 A1 | 10/2004 | Ignatious |
| 2004/0219668 A1 | 11/2004 | Frei et al. |
| 2005/0124862 A1 | 6/2005 | Mousa et al. |
| 2005/0158376 A1 | 7/2005 | Sardi et al. |
| 2005/0171027 A1 | 8/2005 | Sinclair et al. |
| 2005/0222387 A1 | 10/2005 | Debatin et al. |
| 2005/0249721 A1 | 11/2005 | Houston et al. |
| 2005/0266393 A1 | 12/2005 | Baxter et al. |
| 2005/0272817 A1 | 12/2005 | Heino |
| 2006/0166303 A1 | 7/2006 | Spanuth |
| 2006/0210539 A1 | 9/2006 | Zhang |
| 2006/0216251 A1 | 9/2006 | Morariu |
| 2007/0117841 A1 | 5/2007 | Ozes et al. |
| 2007/0190160 A1 | 8/2007 | Turos et al. |
| 2008/0081074 A1 | 4/2008 | Gu et al. |
| 2008/0124280 A1 | 5/2008 | Mousa et al. |
| 2008/0193377 A1 | 8/2008 | Line et al. |
| 2008/0199850 A1 | 8/2008 | Sutter et al. |
| 2009/0022806 A1 | 1/2009 | Mousa et al. |
| 2009/0175862 A1 | 7/2009 | Silverio et al. |
| 2009/0197240 A1 | 8/2009 | Fishman et al. |
| 2010/0159021 A1 | 6/2010 | Davis et al. |
| 2010/0209382 A1 | 8/2010 | Alexander-Bridges et al. |
| 2010/0255108 A1 | 10/2010 | Lin et al. |
| 2011/0052715 A1 | 3/2011 | Davis et al. |
| 2011/0112079 A1 | 5/2011 | Thomas et al. |
| 2011/0142941 A1 | 6/2011 | Davis et al. |
| 2012/0258069 A1 | 10/2012 | Alexander-Bridges et al. |
| 2012/0315320 A1 | 12/2012 | Davis et al. |
| 2014/0744646 | 2/2014 | Li et al. |
| 2014/0072635 A1 | 3/2014 | Mousa et al. |
| 2014/0072646 A1 | 3/2014 | Mousa et al. |
| 2014/0170066 A1 | 6/2014 | Rajopadhye et al. |
| 2014/0199375 A1 | 7/2014 | Mousa et al. |
| 2014/0294931 A1 | 10/2014 | Mousa et al. |
| 2015/0139934 A1 | 5/2015 | Mousa et al. |
| 2015/0238631 A1 | 8/2015 | Kim et al. |
| 2016/0178615 A1 | 6/2016 | Alexander-Bridges et al. |
| 2016/0348052 A1 | 12/2016 | Lin et al. |
| 2017/0080058 A1 | 3/2017 | Mousa et al. |
| 2017/0348425 A1 | 12/2017 | Mousa et al. |

FOREIGN PATENT DOCUMENTS

| | | |
|---|---|---|
| CN | 104530417 A | 4/2015 |
| EP | 2954933 A1 | 12/2015 |
| JP | 04-356184 A | 12/1992 |
| KR | 100830889 B1 | 5/2008 |
| WO | 9500135 | 1/1995 |
| WO | 9640048 | 12/1996 |
| WO | 9833942 | 8/1998 |
| WO | 9856771 | 12/1998 |
| WO | 99/51638 A1 | 10/1999 |
| WO | 9958119 A1 | 11/1999 |
| WO | 9959548 A1 | 11/1999 |
| WO | 9962549 | 12/1999 |
| WO | 0064431 A1 | 11/2000 |
| WO | 0078815 A1 | 12/2000 |
| WO | 0113031 A1 | 2/2001 |
| WO | 0113936 A1 | 3/2001 |
| WO | 076589 A1 | 10/2001 |
| WO | 0203914 A2 | 1/2002 |
| WO | 0249501 A2 | 6/2002 |
| WO | 02060389 A2 | 8/2002 |
| WO | 03075741 A2 | 9/2003 |
| WO | 2004013728 A2 | 2/2004 |
| WO | 2004069201 A2 | 8/2004 |
| WO | 2005027895 A2 | 3/2005 |
| WO | 2006003014 A2 | 1/2006 |
| WO | 2006031022 A2 | 3/2006 |
| WO | 2006031922 A2 | 3/2006 |
| WO | 2007035612 A2 | 3/2007 |
| WO | 2008051291 A2 | 5/2008 |
| WO | 2008140507 A2 | 11/2008 |
| WO | 2010075332 A1 | 7/2010 |
| WO | 2010120506 A1 | 10/2010 |
| WO | 2010148007 A1 | 12/2010 |
| WO | 2012/009425 A2 | 1/2012 |
| WO | 2015/074050 A1 | 5/2015 |
| WO | 2016/004043 A1 | 1/2016 |
| WO | 2017/214299 A1 | 12/2017 |

OTHER PUBLICATIONS

Alexis et al., "Nonocclusive Common Carotid Artery Thrombosis in the Rat Results in Reversible Sensorimotor and Cognitive Behavorial Deficits", Stroke, 26:2338-2346 (1995) 16 pages.

Ali et al., "Angiogenesis as a potential biomarker in prostate cancer chemoprevention trials", Urology, 57(Suppl 4A):143-147 (2001) 5 pages.

Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.

Ali et al., "High levels of oestrogen receptor-α in tumorigenesis: inhibition of cell growth and angiogenic factors", Cell Prolif., 34(4):223-231 (2001) 10 pages.

Allen, A.R., "Surgery of experimental lesion of spinal cord equivalent to crush injury of fracture dislocation of spinal column", J. Am. Med. Assoc., 57(11):878-880 (1911) 4 pages.

Almog et al., "Transcriptional Switch of Dormant Tumors to Fast-Growing Angiogenic Phenotype", Cancer Res., 69 (3):836-844 (2009).

Amirkhosravi et al., "Antimetastatic effect of tinzaparin, a low-molecular-weight heparin", J. Thromb. Haemost., 1:1972-1976 (2003) 5 pages.

Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.

(56) References Cited

OTHER PUBLICATIONS

Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, Supplemental European Search Report dated Apr. 20, 2015. 7 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Application No. PCT/US2017/36396, International Search Report dated Jun. 7, 2017.
Application No. PCT/US2014/66154, International Search Report dated Jan. 27, 2015. 12 pages.
Strieth, et al., "Antiangiogenic combination tumor therapy blocking αv-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n in Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.

Tanaka et al., J. Soc. Gastroenterological Surgery, 27(2):360 (1996) 3 pages.
Tang et al., "Resveratrol-induced Cyclooxygenase-2 facilitates p53-dependent apoptosis in human breast cancer cells", Mol. Cancer Ther., 5(8):2034-2042 (2006) 9 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.
Thraves et al., "Radiosensitization of Human Fibroblasts by 3-Aminobenzamide: An Inhibitor of Poly(ADP-Ribosylation)", Radiat Res., 104:119-127 (1985) 9 pages.
Tol et al., "Chemotherapy, Bevacizumab, and Cetuximab in Metastatic Colorectal Cancer", N. Engl. J. Med., 360(6):563-572 (2009) 10 pages.
Tomanek et al., "A Thyroid Hormone Analog Stimulates Angiogenesis in the Post-infarcted Rat Heart", J. Mol. Cell Cardiol., 30(5):923-932 (1998) 10 pages.
Tomanek et al., "Angiogenesis: New Insights and Therapeutic Potential", Anatomical Record (New Anat.), 261:126-135 (2000) 10 pages.
Tomanek et al., "Early Coronary Angiogenesis in Response to Thyroxine: Growth Characteristics and Upregulation of Basic Fibroblast Growth Factor", Circ. Res., 82(5):587-593 (1998) 8 pages.
Tomanek et al., "Growth of the Coronary Vasculature in Hypertrophy: Mechanisms and Model Dependence", Cell. Mol. Bio. Res., 40(2):129-136 (1994) 8 pages.
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.
Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel αv integrin antagonist SM256 and cis-platinum on growth of murine squamous cell carcinoma PAM LY8", Int. J. Oncol., 16(6):1189-1195 (2000) 8 pages.
VanCutsem et al., "Cetuximab and Chemotherapy as Initial Treatment for Metastatic Colorectal Cancer", N. Engl. J. Med., 360:1408-1417 (2009) 10 pages.
Varnes et al., "The Effect of pH on Potentially Lethal Damage Recovery in A549 Cells", Radiat. Res., 108:80-90 (1986) 11 pages.
Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.
Wang et al., "Integrin-associated Protein Stimulates α2β1-dependent Chemotaxis via Gi-mediated inhibition of Adenylate Cyclase and Extracellular-regulated Kinases", J. Cell. Biol., 147:389-399 (1999) 11 pages.
Wen et al., "Prognostic Value of EGFR and TGF-α in Early Laryngeal Cancer Treated With Radiotherapy", Laryngoscope, 106(7):884-888 (1996) 6 pages.
Werdelin et al., "Neuropeptides and neural cell adhesion molecule (NCAM) in CSF from patients with ALS", Acta Neurol. Scand., 79(3)177-181 (1989).

(56) References Cited

OTHER PUBLICATIONS

Wilkinson, J.H., "Synthesis of some Possible Metabolites of Thyroxine and Triiodothyronine", Biochem. J., 63:601-605 (1956) 5 pages.
Xia et al., "Chemokines/chemokine receptors in the central nervous system and Alzheimer's disease", J. NeuroVirol., 5:32-41 (1999) 11 pages.
Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.
Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.
Yanase et al., "Role of N-methyl-D-aspartate receptor in acute spinal cord injury", J. Neurosurg., 83:884-888 (1995) 6 pages.
Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.
Yang, et al., "Enhanced inhibition of adipogenesis and induction of apoptosis in 3T3-L1 adipocytes with combinations of resveratrol and quercetin", Life Sci., 82:1032-1039 (2008) 8 pages.
Yonkers et al., "Sensory Neuron Sodium Current Requires Nongenomic Actions of Thyroid Hormone During Development", J. Neurophysiol., 100:2719-2725 (2008) 7 pages.
Young, W., "Role of Calcium in Central Nervous System Injuries", J. Neurotrauma, 9(Suppl. 1): S9-S25 (1992) 18 pages.
Young, W., "Secondary injury mechanisms in acute spinal cord injury", J. Emerg. Med., 11:13-22 (1993) 11 pages.
Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.
Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.
Zhang et al., "Oestrogen inhibits resveratrol-induced post-translational modification of p53 and apoptosis in breast cancer cells", Br. J. Cancer, 91:178-185 (2004) 8 pages.
Zhang et al., "Quantitative PET Imaging of Tumor Integrin αvβ3 Expression with 18F-FRGD2", J. Nucl. Med., 47:113-121 (2006) 9 pages.
Zhen et al., "Synthesis and Amyloid Binding Properties of Rhenium Complexes: Preliminary Progress Toward a Reagent for SPECT Imaging of Alzheimer's Disease Brain", J. Med. Chem., 42:2805-2815 (1999) 11 pages.
Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.
Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages.
NCI Cancer Drug Information, Cetuximab, 2006,http://www.cancer.gov/cancertopics/druginfo/cetuximab,downloaded Jul. 18, 2014.
Leuthy,A.; et al. "Autologous stem cell transplantation: leukapheresis product has anti-angiogenic effects in vivo correlating with neutrophil-derived 'VEGFR1" Anticancer Research, 2001, v.31, 9.3115-3124.
Mythyroid.com. "Blood tests" (Http://222.mythyroid.com/bloodtests.html) cached 2005 wayback machine.
Huang Kuo-Shiang et al. "Combination of baculovirus-mediated gene delivery and packed-bed reactor for scalable production of adeno-associated virus", Human Gene Therapy, Mary Ann Liebert, Inc., publishers, us., vol. 18, No. 11. 2007, pp. 1161-1170.

Hung-Yun Lin et al. "Pharmacodynamic modeling of anti-cancer activity of tetraiodotheyroacetic acid in a perfused cell culture system" Plos Computational Biology, vol. 7, n.2, 2011, p. e1001073.
Notice of Allowance dated Jan. 31, 2018 U.S. Appl. No. 13/975,725, filed Aug. 26, 2013.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573(1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Oncol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an in Vitro Hollow-Fiber Model System", Antimicrob. Agents Chemother, 46(2):464-470 (2002) 7 pages.
Dupont et al., "Antiangiogenic and antimetastatic properties of Neovastat Æ 941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138 (1993) 8 pages.
Everts et al., "Uptake of 3,3',5.5'-Tetraiodothyroacetic Acid and 3,3 ',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17(4):386-390 (1985) 5 pages.
Faden, A.I., "Experimental Neurobiology of Central Nervous System Trauma", Crit. Rev. Neurobiol., 7(3-4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.

(56) References Cited

OTHER PUBLICATIONS

Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of αv/β3 mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521(1-2):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death in Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Geng et al., "A Specific Antagonist of the p110δ Catalytic Component of Phosphatidylinositol 3'-Kinase, IC486068, Enhances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.
Gladson, C.L., "Expression of integrin αvβ3 in Small Blood Vessels of Glioblastoma Tumors", J. Neuropath. Exp. Neurol., 55(11):1143-1149(1996) 7 pages.
Glinskii et al., "Modification of survival pathway gene expression in human breast cancer cells by tetraiodothyroacetic acid (tetrac)", Cell Cycle, 8(21):3562-3570 (2009) 9 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression profiling predicts clinical outcome of prostate cancer", J. Clin. Invest., 113(6):913-923 (2004) 11 pages.
Glinsky et al., "Microarray analysis identifies a death-from-cancer signature predicting therapy failure in patients with multiple types of cancer", J. Clin. Invest., 115(6):1503-1521 (2005) 19 pages.
Glinsky et al., "Microarray Analysis of Xenograft-Derived Cancer Cell Lines Representing Multiple Experimental Models of Human Prostate Cancer", Mol. Carcinog., 37:209-221 (2003) 13 pages.
Goldstein et al., "Influence of Lesion Size and Location on Amphetamine-Facilitated Recovery of Beam-Walking in Rats", Behav. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.

Grant, D.B. "Monitoring TSH concentrations during treatment for congenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
Guigon et al., "Regulation of β-Catenin by a Novel Nongenomic Action of Thyroid Hormone β Receptor", Mol. Cell. Biol., 28(14):4598-4608 (2008) 11 pages.
Hahn et al., "Plateau-phase cultures of mammalian cells: An in vitro model for human cancer", Curr. Top. Radiat. Res. Q., 8:39-83 (1972) 45 pages.
Halks-Miller et al., "CCR1 Immunoreactivity in Alzheimer's Disease Brains", Society for Neuroscience Meeting, Abstract #787.6, vol. 24 (1998) Abstract Only. 1 page.
Hansebout, R.R., "A Comprehensive Review of Methods of Improving Cord Recovery After Acute Spinal Cord Injury", in Early Management of Acute Spinal Cord Injury, pp. 181-196 (1982) 16 pages.
Hartert H., "Blutgerinnungsstud Mit Der Thrombelastogeraphie, Einem Neuen Untersuchungsverfahren", Klinische Wochenschrift 26(37/38):577-583 (1948) German Language Only. 9 pages.
Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.
Heller et al., "Inhibition of potentially lethal damage recovery by altered pH, glucose utilization and proliferation in plateau growth phase human glioma cells", Int. J. Radiat. Biol., 66(1):41-47 (1994) 7 pages.
Hercbergs et al., "GL261 brain tumor cells: responses to single or fractionated x-irradiation with the αvβ3 integrin thyroxine receptor antagonist tetrac (tetraiodothyroacetic acid)", 20th EORTC-NCI-AACR Symposium on Molecular Targets and Cancer Therapeutics, Geneva, Switzerland, Oct. 2008.
Hercbergs et al., "GL261 brain tumor cells: responses to single or fractionated x-irradiation with the αvβ33 integrin thyroxine receptor antagonist tetrac (tetraiodothyroacetic acid)", Euro. J. Cancer, 6(12):172 (Abstract Only) 4 pages.
Hercbergs et al., "Propylthiouracil-induced Chemical Hypothyroidism with High-Dose Tamoxifen Prolongs Survival in Recurrent High Grade Glioma: A Phase I/II Study", Anticancer Res., 23:617-626 (2003) 10 pages.
Hercbergs, A., "The Thyroid Gland as an Intrinsic Biologic Response-Modifier in Advanced Neoplasia—A Novel Paradigm", in vivo, 10:245-247 (1996) 3 pages.
Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.
Hercbergs, et al., "Radiosensitization of GL261 glioma cells by tetraiodothyroacetic acid (tetrac)", Cell Cycle, 8(16):2586-2591 (2009) 6 pages.
Hermanson, "Modification with Synthetic Polymers", in Bioconjugate Tech., Ch. 15, Academic Press, San Diego, CA, pp. 617-618 (1996) 4 pages.
Hoff et al., "Medullary Thyroid Carcinoma", Hematol. Oncol. Cin. North Am., 21(3):475-488 (2007) 14 pages.
Horuk et al., "Expression of Chemokine Receptors by Subsets of Neurons in the Central Nervous System", J. Immunol., 158:2882-2890 (1997) 9 pages.
Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.
Hudlicka et al., "Factors involved in capillary growth in the heart", Mol. Cell. Biochem, 147:57-68 (1995) 12 pages.
Igarashi et al., "Techniques Supporting Angiogenesis Therapy 2: DDS Technique Supporting Regenerative Medicine." Inflamm. Immun. 10.6(2002):652-658 7 pages.
Illario et al., "Fibronectin-Induced Proliferation in Thyroid Cells is Mediated by αvβ3 Integrin through Ras/Raf-1/MEK/ERK and Calcium/CaMKII Signals", J. Clin. Endocrinol. Metab., 90(5):2865-2873 (2005) 9 pages.

(56) References Cited

OTHER PUBLICATIONS

Ingerman-Wojenski et al., "Evaluation of electrical aggregometry: comparison with optical aggregometry, secretion of ATP, and accumulation of radiolabeled platelets", J. Lab. Clin. Med., 101(1):44-52 (1983) 10 pages.

Iwata et al., "A new, convenient method for the preparation of 4-[18F]fluorobenzyl halides", Applied Radiation and Isotopes, 52(1):87-92 (2000) 7 pages.

Jain, K.K., "Strategies and technologies for drug delivery systems", TIPS, 19:155-157 (1998) 5 pages.

Janssen et al., "Pathogenesis of Spinal Cord Injury and Newer Treatments—A Review", Spine, 14(1):23-32 (1989) 11 pages.

Jeffrey et al., "The preparation and characterisation of poly(lactide-co-glycolide) microparticles. 1. Oil-in-water emulsion solvent evaporation", Int. J. Pharm., 77:169-175 (1991) 7 pages.

Jonker et al., "Cetuximab for the Treatment of Colorectal Cancer", N. Engl. J. Med., 357(20):2040-2048 (2007) 9 pages.

Jordan et al., "Thyroid Status is a Key Modulator of Tumor Oxygenation: Implication for Radiation Therapy", Radiat. Res., 168:428-432 (2007) 5 pages.

Kalofonos et al., "Monoclonal Antibodies in the Management of Solid Tumors", Curr. Top. Med. Chem., 6:1687-1705 (2006) 19 pages.

Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.

Kastan et al., "A Mammalian Cell Cycle Checkpoint Pathway Utliziing P53 and GADD45 is Defective in Ataxia-Telangiectasia", Cell. 71:587-597 (1992) 11 pages.

Kawasuji et al., Jap. Circ. J., 63(Suppl. 1):65 (1999) Japanese Abstract Only. 3 pages.

Kerr et al., "Novel Small Molecule αv Integrin Antagonists: Comparative Anti-Cancer Efficacy with Known Angiogenesis Inhibitors", Anticancer Res., 19:959-968 (1999).

Kerr et al., "Small molecule αvintegrin antagonists: novel anticancer agents", Exp. Opin. Invest. Drugs, 9(6)1271-1279 (2000) 9 pages.

Kim et al., "Regulation of Angiogenesis in Vivo, by Ligation of Integrin α5β1 with the Central Cell-Binding Domain of Fibronectin", Am. J. Pathol., 156(4): 1345-1362 (2000) 18 pages.

Kim et al., "Soluble Flt-1 gene delivery using PEI-g-PEG-RGD conjugate for anti-angiogenesis", J. Control Release, 106:224-234 (2005) 11 pages.

Kimelberg, H.K., "Astrocytic Edema in CNS Trauma", J. Neurotrauma, 9(Suppl. 1):S71-S81 (1992) 12 pages.

Kitevska et al., "Caspase-2: controversial killer or checkpoint controller?", Apoptosis, 14:829-848(2009) 20 pages.

Kleczkowska et al., "Differential poly(ADP-ribose) metabolism in repair-proficient and repair-deficient murine lymphoma cells", Mut. Res., 235:93-99 (1990) 7 pages.

Klunk et al., "Development of Small Molecule Probes for the Beta-Amyloid Protein of Alzheimer's Disease", Neurobiol. Aging, 15(6):691-698 (1994) 8 pages.

Kobayashi et al., "Drug Delivery Catheter." Surg. Front. 9.1(2002):55-57 3 pages.

Konno et al., "Antiogenetic therapy for carcinoma", Igaku No Ayumi, 194(10): 824-828 (2000) 5 pages.

Koutras et al., "Antiproliferative effect of exemestane in lung cancer cells", Mol. Cancer, 8(1):109 (2009) 12 pages.

Koyama et al., "Recent Status and Future Perspectives in Therapeutic Angiogenesis", Prog. Med., 22(12):3070-3076 (2002) (English Abstract) 7 pages.

Kramer et al., "Human Microvascular Endothelial Cells Use β1 and β3 Integrin Receptor Complexes to Attach to Laminin", J. Cell Biol., 111:1233-1343 (1990) 11 pages.

Kumar et al., "Enhancing Effect of Thyroxine on Tumor Growth and Metastases in Syngeneic Mouse Tumor Systems", Cancer Res., 39:3515-3518 (1979) 4 pages.

Kuroki et al., "Diabetic retinopathy—The mechanisms of the ocular neovascularization of the development of anti-angiogenic drugs-", Nippon Rinsho, 57(3):584-589 (1999) (English Abstract Only) 6 pages.

Kwok et al., "Differences in EGF rated radiosensitisation of human squamous carcinoma cells with high and low numbers of EGF receptors", Br. J. Cancer, 64:251-254 (1991) 4 pages.

Lameloise et al., "Differences between the effects of thyroxine and tetraiodothyroacetic acid on TSH suppression and cardiac hypertrophy", Eur. J. Endocrinol., 144:145-154 (2001) 10 pages.

Lawler et al., "Cell Attachment to Thrombospondin: The Role of ARG-GLY-ASP, Calcium and Integrin Receptors", J. Cell Biol., 107(6 Pt. 1): 2351-2361 (1988) 11 pages.

Letterio et al., "Maternal Rescue of Transforming Growth Factor-β1 Null Mice", Science, 264:1936-1938 (1994) 4 pages.

Li et al., "Requirement of hypoxia-inducible factor-1α down-regulation in mediating the antitumor activity of the anti-epidermal growth factor receptor monoclonal antibody cetuximab", Mol. Cancer Ther., 7(5):1207-1217 (2008) 11 pages.

Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.

Lin et al., "Identification of the Putative MAP Kinase Docking Site in the Thyroid Hormone Receptor-β1 DNA-Binding Domain: Functional Consequences of Mutations at the Docking Site", Biochem., 42:7571-7579 (2003) 9 pages.

Lin et al., "Integrin αvβ3 contains a receptor site for resveratrol", FASEB J., 20(10): 1742-1744 (2006) 3 pages.

Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.

Lin et al., "Resveratrol Causes COX-2- and p53-Dependent Apoptosis in Head and Neck Squamous Cell Cancer Cells", J. Cell Biochem., 104:2131-2142 (2008) 12 pages.

Lin et al., "Resveratrol Induced Serine Phosphorylation of p53 Causes Apoptosis in a Mutant p53 Prostate Cancer Cell Line", J. Urol., 168:748-755 (2002) 8 pages.

Lin et al., "Resveratrol is pro-apoptotic and thyroid hormone is anti-apoptotic in glioma cells: both actions are integrin and ERK mediated", Carcinogenesis, 29(1):62-69 (2008) 8 pages.

Lin et al., "The pro-apoptotic action of stilbene-induced COX-2 in cancer cells: Convergence with the anti-apoptotic affect of thyroid hormone", Cell Cycle, 8(12):1877-1882 (2009) 6 pages.

Lin et al., "Thyroid hormone is a MAPK-dependent growth factor for thyroid cancer cells and is anti-apoptotic", Steroids, 72:180-187 (2007) 8 pages.

Liu et al., "Calcineurin Is a Common Target of Cyclophilin-Cyclosporin A and FKBP-FK506 Complexes", Cell, 66:807-815 (1991) 9 pages.

Lorger et al., "Activation of tumor cell integrin αvβ3 controls angiogenesis and metastatic growth in the brain", Proc. Natl. Acad. Sci. U.S.A., 106(26):10666-10671 (2009) 7 pages.

Louie et al. "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.

Luidens et al., "Thyroid hormone and angiogenesis", Vascular Pharmacology, 52(3-4): 142-145 (2010) 4 pages.

Lyons et al., "The Expression of an N-CAM Serum Fragment is Positively Correlated with Severity of Negative Features in Type II Schizophrenia", Biol. Psychiatry, 23:769-775 (1988) 7 pages.

Ma, et al., "Use of Encapsulated Single Chain Antibodies for Induction of Anti-Idiotypic Humoral and Cellular Immune Responses", J. Pharm. Sci., 87:1375-1378 (1998). 4 pages.

Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.

(56) References Cited

OTHER PUBLICATIONS

Mandelin et al., "Extracellular and Intracellular Mechanisms That Mediate the Metastatic Activity of Exogenous Osteopontin", Cancer, 115:1753-1764 (2009) 12 pages.
Mangale et al., "Identification of genes regulated by an interaction between αvβ3 integrin and vitronectin in murine decidua", Reprod. Fertil. Dev., 20:311-319 (2008) 10 pages.
Markgraf et al., "Sensorimotor and cognitive consequences of middle cerebral artery occlusion in rats", Brain Res., 575(2):238-246 (1992) 10 pages.
Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.
Masson-Gadais et al., "Integrin αvβ3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.
McCarty et al., "Promises and Pitfalls of Anti-Angiogenic Therapy in Clinical Trials." Trends Mol. Med. 9.2(2003):53-58 6 pages.
Meneses et al., "Recombinant angiostatin prevents retinal neovascularization in a murine proliferative retinopathy model", Gene Therapy, 8(8):646-648 (2011) 3 pages.
Mezosi et al., "Nongenomic effect of thyroid hormone on free-radical production in human polymorphonuclear eukocytes", J. Endocrinol., 185:121-129 (2005) 9 pages.
Mishkin et al., "Increased Survival of Rats Bearing Morris Hepatoma 7800 after Induction of Hypothyroidism", Cancer Res., 39:2371-2375 (1979) 5 pages.
Miyaguchi et al., "Correlation of Epidermal Growth Factor Receptor and Radiosensitivity in Human Maxillary Carcinoma Cell Lines", ActaOtolaryngol., 118:428-431 (1998) 4 pages.
Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.
Moeller et al., "Thyroid hormone mediated changes in gene expression can be initiated by cytosolic action of the thyroid hormone receptor beta through the phosphatidylinositol 3-kinase pathway", Nuclear Receptor Signaling, 4: E020 (2006) 4 pages.
Mohamed et al., "Wound healing properties of cimetidine in vitro", Drug Intell. Clin. Pharm., 20(12):973-975 (1986) 4 pages.
Monferran et al., "αvβ3 and αvβ5 integrins control glioma cell response to ionising radiation through ILK and RhoB", Int. J. Cancer, 123:357-364 (2008) 8 pages.
Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.
Moreno et al., "Metabolic Effects of Thyroid Hormone Derivatives", Thyroid, 18(2):239-253 (2008) 15 pages.
Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18 (2):239-253 (2008) 15 pages.
Mousa et al., "Cellular and Molecular Mechanisms of Nicotine's Pro-Angiogenesis Activity and Its Potential Impact on Cancer", J. Cell. Biochem., 97:1370-1378 (2006) 9 pages.
Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.
Mousa et al., "Discovery of pro-angiogenic effects of thyroid hormone analogs", Database Biosis (Online) Biosciences Information Service, Database Accession No. PREV20040016169 (Nov. 16, 2003) Same as 220 and 221.
Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.
Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.
Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.
Mousa et al., "The Proangiogenic Action of Thyroid Hormone Analogue GC-1 Is Initiated at an Integrin", J. Cardiovasc. Pharmacol., 46(3):356-360 (2005) 6 pages.
Mousa, et al., "Pro-angiogenesis action of thyroid hormone and analogs in a three-dimensional in vitro microvascular endothelial sprouting model", Int. Angiol., 25(4):407-413 (2006).
Mousa, S.A., "Mechanisms of Angiogenesis: Potential Therapeutic Targets", in Angiogenesis Inhibitors and Stimulators: Potential Therapeutic Implications, Landes Bioscience, Georgetown, Texas, Chapter I, pp. 1-12 (2000) 14 pages.
Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.
Muller et al., "The Double Life of the Ku Protein: Facing the DNA Breaks and the Extracellular Environment", Cell Cycle, 4(3):438-441 (2005) 4 pages.
Gu et al. 2007, Nanotoday 2:14-21 . . . .
J Wood, K Bonjean, S Ruetz, A Bellahcene, L Devy, JM Foidart, V Castronovo, JR Green. "Novel Antiangiogenic Effects of the u Bisphosphonate Compound Zoledronic Acid." The Journal of Pharmacology and Experimental Therapeutics, vol. 302, No. 3, 2002, pp. 1055-1061.
M Yalcin, DJ Bharali, L Lansing, E Dyskin, SS Mousa, A Hercbergs, FB Davis, PJ Davis, SA Mousa. "Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.
Park, T.G., "Bioconjugation of Biodegradable Poly (lactic'glycolic acid) to Protein, Peptide, and Anti-Cancer Drug: An Alternative Pathway for Achieving Controlled Release from Micro- and Nanoparticles." in Polymeric Drugs and Drug Delivery Systems, Ottenbrite R.M. and Kim S.W., eds., Ch. 7, pp. 101-114 (2001).
Oh, Jong Eun, et al., "Conjugation of drug to poly (D,L-lacitic-coglycoli acid) for controlled release from biodegradable microspheres." Journal of Controlled Release 57, 269-280 (1999).
Ditsch, Nina, et al., "Thyroid Function in Breast Cancer Patients." Anticancer Research 30: 1713-1718 (2010).
Davis, Faith B., et al., "Proangiogenic Action of Thyroid Hormone Is Fibroblast Growth Factor-Dependent and Is Initiated at the Cell Surface." Circulation Research, 2004, 94, 1500-1506.
Webmd.com (http://www.webmd.com/women/news/20030410/underactive-thyroid-lowers-breast-cancer). Dated Apr. 10, 2003.
Mousa, Shaker A., et al., "Tetraiodothyroacetic acid and its nanoformulation inhibit thyroid hormone stimulation of non-small cell lung cancer cells in vitro and its growth in xenografts." Lung Cancer 76; 39-45 (2012).
Restriction Requirement dated May 5, 2016 for U.S. Appl. No. 14/977,776.
Office Action dated Nov. 4, 2016 for U.S. Appl. No. 14/977,776.
Office Action dated Mar. 24, 2015 for U.S. Appl. No. 13/975,725, filed Aug. 26, 2013.
Final Office Action dated Oct. 9, 2015 for U.S. Appl. No. 13/975,725, filed Aug. 26, 2013.
Avisory Action dated Dec. 31, 2015 for U.S. Appl. No. 13/975,725, filed Aug. 26, 2013.
Office Action dated Jun. 17, 2016 for U.S. Appl. No. 13/975,725, filed Aug. 26, 2013.
Final Office Action dated Apr. 3, 2017 for U.S. Appl. No. 13/975,725, filed Aug. 26, 2013.
Office Action dated Oct. 5, 2012 for U.S. Appl. No. 12/644,493, filed Dec. 22, 2009.
Office Action dated Oct. 16, 2014 for U.S. Appl. No. 12/644,493, filed Dec. 22, 2009.
Office Action dated Oct. 12, 2016 for U.S. Appl. No. 12/644,493, filed Dec. 22, 2009.

(56) References Cited

OTHER PUBLICATIONS

Office Action dated Apr. 24, 2017 for U.S. Appl. No. 12/644,493, filed Dec. 22, 2009.
Office Action dated Apr. 2, 2013 for U.S. Appl. No. 13/156,047, filed Jun. 8, 2011.
Office Action dated Feb. 25, 2014 for U.S. Appl. No. 13/156,047, filed Jun. 8, 2011.
Office Action dated Apr. 16, 2015 for U.S. Appl. No. 13/156,047, filed Jun. 8, 2011.
Notice of Allowance dated Nov. 2, 2015 for U.S. Appl. No. 13/256,047, filed Jun. 8, 2011.
Restriction Requirement dated Nov. 4, 2015 for U.S. Appl. No. 14/546,440, filed Nov. 18, 2014.
Office Action dated Mar. 24, 2016 for U.S. Appl. No. 14/546,440, filed Nov. 18, 2014.
Office Action dated Sep. 30, 2016 for U.S. Appl. No. 14/546,440, filed Nov. 18, 2014.
European Office Action for EP Application No. 07867073.4, dated Jul. 16, 2015.
Restriction Requirement dated Feb. 9, 2017 for U.S. Appl. No. 15/056,522, filed Feb. 29, 2016.
Office Action dated Dec. 21, 2007 for U.S. Appl. No. 10/943,072, filed Sep. 14, 2004.
Advisory Action dated Feb. 27, 2008 for U.S. Appl. No. 10/943,072, filed Sep. 14, 2004.
Office Action dated May 15, 2008 for U.S. Appl. No. 10/943,072, filed Sep. 14, 2004.
Office Action dated Jan. 8, 2009 for U.S. Appl. No. 10/943,072, filed Sep. 14, 2004.
Office Action dated Jun. 22, 2009 for U.S. Appl. No. 10/943,072, filed Sep. 14, 2004.
Notice of Allowance dated Dec. 11, 2009 for U.S. Appl. No. 10/943,072, filed Sep. 14, 2004.
Office Action dated May 12, 2015 for U.S. Appl. No. 14/078,713, filed Nov. 13, 2013.
Notice of Allowance dated Aug. 3, 2015 for U.S. Appl. No. 14/078,713, filed Nov. 13, 2013.
Restriction Requirement dated Dec. 3, 2015 for U.S. Appl. No. 14/184,889, filed Feb. 20, 2014.
Office Action dated May 6, 2016 for U.S. Appl. No. 14/184,889, filed Feb. 20, 2014.
Notice of Allowance dated Oct. 13, 2016 for U.S. Appl. No. 14/184,889, filed Feb. 20, 2014.
Restriction Requirement dated Dec. 2, 2015 for U.S. Appl. No. 14/185,010, filed Feb. 20, 2014.
Office Action dated Sep. 9, 2016 for U.S. Appl. No. 14/185,010, filed Feb. 20, 2014.
Notice of Allowance for U.S. Appl. No. 14/185,010 dated Apr. 4, 2017.
Office Action dated Oct. 14, 2014 for U.S. Appl. No. 14/242,041, filed Apr. 2, 2014.
Office Action dated Jun. 11, 2015 for U.S. Appl. No. 14/242,041, filed Apr. 1, 2014.
Final Office Action dated Oct. 16, 2015 for U.S. Appl. No. 14/242,041, filed Apr. 1, 2014.
Advisory Action dated Jan. 21, 2016 for U.S. Appl. No. 14/242,041, filed Apr. 1, 2014.
Office Action dated May 26, 2016 for U.S. Appl. No. 14/242,041, filed Apr. 2, 2014.
Notice of Allowance dated Jul. 19, 2016 for U.S. Appl. No. 14/242,041, filed Apr. 1, 2014.
Office Action dated Oct. 4, 2017 for U.S. Appl. No. 14/546,440, filed Nov. 18, 2014.
Notice of Allowance dated May 3, 2018 for U.S. Appl. No. 14/546,440, filed Nov. 18, 2014.
Office Action dated Jun. 13, 2018 for U.S. Appl. No. 15/056,522, filed Feb. 29, 2016.
Office Action dated Jun. 11, 2018 for U.S. Appl. No. 14/903,149, filed Jan. 6, 2016.
Office Action dated Dec. 29, 2017 for U.S. Appl. No. 15/357,818, filed Nov. 21, 2016.
Office Action dated Apr. 20, 2018 for U.S. Appl. No. 15/357,818, filed Nov. 21, 2016.
Notice of Allowance dated Jul. 3, 2018 for U.S. Appl. No. 15/357,818, filed Nov. 21, 2016.
Estrada-Ortiz, Natalia, et al. "Artificial Macrocycles as Potent p53-MDM2 Inhibitors," ACS Med. Chem. Lett. 2017, 8, 1025-1030, 6 pages.
Surmiak, Ewa, et al. "Rational design and synthesis of 1,5-disubstituted tetrazoles as potent inhibitors of the MDM2-p53 interaction," European Journal of Medicinal Chemistry, 126, (2017) 384-407, 24 pages.
Suryakiran, N., et al. "Facile N-tert-butoxycarbonylation of amines using La(NO3)3•6H2O as a mil and efficient catalyst under solvent-free conditions," Tetrahedron Letters, 47 (2006), 8039-8042; 4 pages.
Audus et al., "Bovine Brain Microvessel Endothelial Cell Monolayers as a Model System for the Blood-Brain Barrier'" in Biological Approaches to the Controlled Delivery of Drugs, Ann. N.Y. Acad. Sci., 507:9-18 (1987) 11 pages.
Bergstrom et al., "Reduction of fibrinogen absorption on PEG-coated polystyrene surfaces", J. Biomed. Mat. Res., 26:779-790 (1992) 12 pages.
Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.
Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.
Nehls et al., "A Novel Micorcarrier-Based in Vitro Assay for Rapid and Reliable Quantification of Three-Dimensional Cell Migration and Angiogenesis", Microvasc. Res., 50(3):311-322 (1995) 12 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.
Oshaghi, Ebrahim Abbasi, et al., "Role of resveratrol in the management of insulin resistance and related conditions: Mechanism of action," Critical Reviews in Clinical Laboratory Sciences, 2017. vol. 54, No. 4, pp. 27-293.
Mayo Clinic, "Multiple sclerosis—Diagnosis and treatment," URL: https://www.mayoclinic.org/diseases-conditions/multiple-sclerosis/diagnosis-treatment/drc-20350274 accessed Dec. 21, 217, 12 printed pages. (Year: 2017).
Susman, E., "Beware of Non-Aspirin NSAIDs for Kidney Cancer Patients." Genitourinary Cancers Symposium, oncology-times.com, 2016, p. 21. (Year: 2016).
Application No. PCT/US04/030583, International Preliminary Report on Patentability dated Mar. 16, 2006, 9 pages.
Lane, N.E., et al., "Osteoarthritis year in review 2016: clinical," Osteoarthritis and Cartilage, vol. 25, 2017, pp. 209-215 (Year: 2017).
*Kennecott Corporation*, Plaintiff-Appellant v. *Kyocera International, Inc., and Kyoto Ceramic Co., Ltd.*, Defendant-Appellee. Case Decided Dec. 22, 1987. (https://law.resource.org/pub/us/case/reporterF2/835/835.F2d.1419.871151.html), accessed Jan. 15, 2016, 5 printed pages.
Application No. PCT/US11/043837, International Preliminary Report on Patentability dated Jan. 15, 2013. 5 pages.
Tetraiodothyroacetic Acid-Tagged Liposomes for Enhanced Delivery of Anticancer Drug to Tumor Tissue Via Integrin Receptor http://www.sciencedirect.com/sciencearticle/pii/S0168365912004567.
64Cu-Labeled Tetraiodothyroacetic Acid-Conjugated Liposomes for PET Imaging of Tumor Angiogenesis http://www.sciencedirect.con/science/article/pii/S969805113001704.

(56) References Cited

OTHER PUBLICATIONS

European Patent Application No. 10 790 068.0, Office Action dated Jul. 11, 2018. 4 pages.
Office Action dated Jul. 21, 2010 for U.S. Appl. No. 12/004,979, filed Dec. 21, 2007.
Office Action dated Jun. 21, 2011 for U.S. Appl. No. 12/947,389, filed Nov. 16, 2010.
Office Action dated Apr. 4, 2012 for U.S. Appl. No. 12/947,389, filed Nov. 16, 2010.
Office Action dated Oct. 17, 2012 for U.S. Appl. No. 12/947,389, filed Nov. 16, 2010.
Office Action dated Mar. 12, 2014 for U.S. Appl. No. 12/947,389, filed Nov. 16, 2010.
Office Action dated Sep. 4, 2014 for U.S. Appl. No. 12/947,389, filed Nov. 16, 2010.
Notice of Allowance dated Nov. 16, 2015 for U.S. Appl. No. 12/947,389, filed Nov. 16, 2010.
Office Action dated May 23, 2012 for U.S. Appl. No. 12/816,287, filed Jun. 15, 2010.
Office Action dated Apr. 11, 2013 for U.S. Appl. No. 12/816,287, filed Jun. 15, 2010.
Office Action dated Oct. 24, 2013 for U.S. Appl. No. 12/816,287, filed Jun. 15, 2010.
Office Action dated May 8, 2014 for U.S. Appl. No. 12/816,287, filed Jun. 15, 2010.
Notice of Allowance dated May 12, 2015 for U.S. Appl. No. 12/816,287.
Restriction Requirment dated Sep. 14, 2012 for U.S. Appl. No. 12/626,068, filed Nov. 25, 2009.
Office Action dated Jan. 4, 2013 for U.S. Appl. No. 12/626,068, filed Nov. 25, 2009.
Notice of Allowance dated Apr. 29, 2013 for U.S. Appl. No. 12/626,068, filed Nov. 25, 2009.
Office Action dated Mar. 16, 2011 for U.S. Appl. No. 11/663,047, filed Oct. 9, 2007.
Notice of Allowance dated Aug. 22, 2011 for U.S. Appl. No. 11/663,047, filed Oct. 9, 2007.
Office Action dated Apr. 8, 2013 for U.S. Appl. No. 11/786,723, filed Apr. 11, 2007.
Restriction Requirement dated Oct. 8, 2010 for U.S. Appl. No. 11/992,152, filed Nov. 3, 2009.
Office Action dated Dec. 10, 2010 for U.S. Appl. No. 11/992,152, filed Nov. 3, 2009.
Restriction Requirement dated Feb. 7, 2013 for U.S. Appl. No. 13/345,194, filed Jan. 6, 2012.
Offce Action dated Apr. 29, 2013 for U.S. Appl. No. 13/345,194, filed Jan. 6, 2012.
Office Action dated Oct. 15, 2013 for U.S. Appl. No. 13/345,194, filed Jan. 6, 2012.
Notice of Allowance dated Feb. 6, 2014 for U.S. Appl. No. 13/345,194, filed Jan. 6, 2012.
Restriction Requirement dated Mar. 13, 2012 for U.S. Appl. No. 12/751,375, filed Mar. 31, 2010.
Office Action dated Jul. 13, 2012 for U.S. Appl. No. 12/751,375, filed Mar. 31, 2010.
Office Action dated Apr. 12, 2013 for U.S. Appl. No. 12/751,375, filed Mar. 31, 2010.
Office Action dated Jan. 12, 2015 for U.S. Appl. No. 12/751,375, filed Mar. 31, 2010.
Office Action dated Jun. 3, 2015 for U.S. Appl. No. 12/751,375, filed Mar. 31, 2010.
Notice of Allowance dated Jul. 7, 2015 for U.S. Appl. No. 12/751,375, filed Mar. 31, 2010.
Restriction Requirement dated May 18, 2007 for U.S. Appl. No. 10/943,072, filed Sep. 14, 2004.
Office Action dated Jul. 9, 2007 for U.S. Appl. No. 10/943,072, filed Sep. 14, 2004.

* cited by examiner

NON-CLEAVABLE POLYMER CONJUGATED WITH αVβ3 INTEGRIN THYROID ANTAGONISTS

CROSS REFERENCE TO RELATED APPLICATIONS

This application claims priority and benefit of U.S. Application No. 62/346,659 entitled "NOVEL COMPOSITIONS AND METHODS OF US OF NON-CLEAVABLE POLYMER CONJUGATED WITH NOVEL ALPHA-V-BETA-3 THYROID ANTAGONISTS, filed Jun. 7, 2016, the content of which is incorporated herein by reference.

TECHNICAL FIELD

The present disclosure relates generally to thyroid hormone receptor antagonists (referred to as "thyrointegrin antagonists") and more specifically to alpha-V-beta-3 (αVβ3) integrin-thyroid hormone receptor antagonists conjugated via a non-cleavable bond of a linker with or without a short chain of PEG to one or more polymers (in embodiments utilizing a polymer other than PEG).

BACKGROUND

Integrins are a super-family of cell surface adhesion receptors, which control the attachment of cells with the solid extracellular environment, both to the extracellular matrix (ECM), and to other cells. Adhesion is of fundamental importance to a cell; it provides anchorage, cues for migration, and signals for growth and differentiation. Integrins are directly involved in numerous normal and pathological conditions, and as such are primary targets for therapeutic intervention. Integrins are integral transmembrane proteins, heterodimers, whose binding specificity depends on which of the 14 α-chains are combined with which of the 8 β-chains. The integrins are classified in four overlapping subfamilies, containing the β1, β2, β3 or αv chains. A cell may express several different integrins from each subfamily. In the last several decades, it has been shown that integrins are major receptors involved in cell adhesion, and so may be a suitable target for therapeutic intervention. Integrin αvβ3 regulates cell growth and survival, since ligation of this receptor can, under some circumstances, induce apoptosis in tumor cells. Disruption of cell adhesion with anti-αvβ3 antibodies, RGD peptides, and other integrin antagonists has been shown to slow tumor growth.

SUMMARY

A first embodiment of this disclosure relates generally to a composition comprising a general formula:

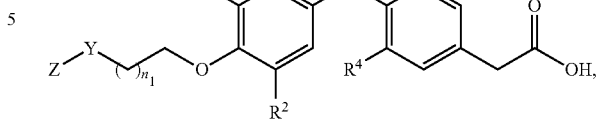

wherein R1, R2, R3 and R4 are each independently selected from the group consisting of hydrogen, iodine, linear alkanes and branched alkanes; X is oxygen (O) or sulfur (S); $n1 \geq 0$; Y is a non-cleavable covalent bond; and Z is a non-biodegradable polymer. Y=

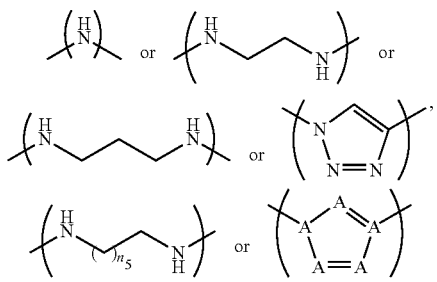

Wherein $n_5=1\text{-}5$, and A=CH or N, with at least one A=N

A second embodiment of the present disclosure relates generally to a composition comprising a general formula:

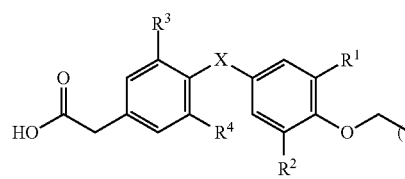

wherein $R^1$, $R^2$, $R^3$ and $R^4$ are each independently selected from the group consisting of hydrogen, iodine, linear alkanes and branched alkanes; X is oxygen (O) or sulfur (S); $n_1 \geq 0$; $n_2 \geq 1$; and Y=

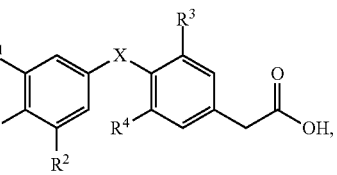

A third embodiment of the present disclosure relates generally to a composition comprising a thyroid antagonist, a non-biodegradable polymer; and a linker covalently bound to the thyroid antagonist and the non-biodegradable polymer via a non-cleavable covalent bond. Wherein, even under some circumstances that one or more of the listed polymers may be cleaved through the use of harsh environmental conditions, a residual polymer chain may still be covalently bonded to the linker and MAT, DAT or TAT, capable of still restricting the cellular nucleus uptake of the conjugated thyroid antagonist.

BRIEF DESCRIPTION OF THE DRAWINGS

Some of the embodiments will be described in detail with references made to the following figures, wherein like designations denote like members, wherein:

FIG. 2d depicts an alternative embodiment of the tetrac derivative of FIG. 2a.

DETAILED DESCRIPTION

Figure 1:
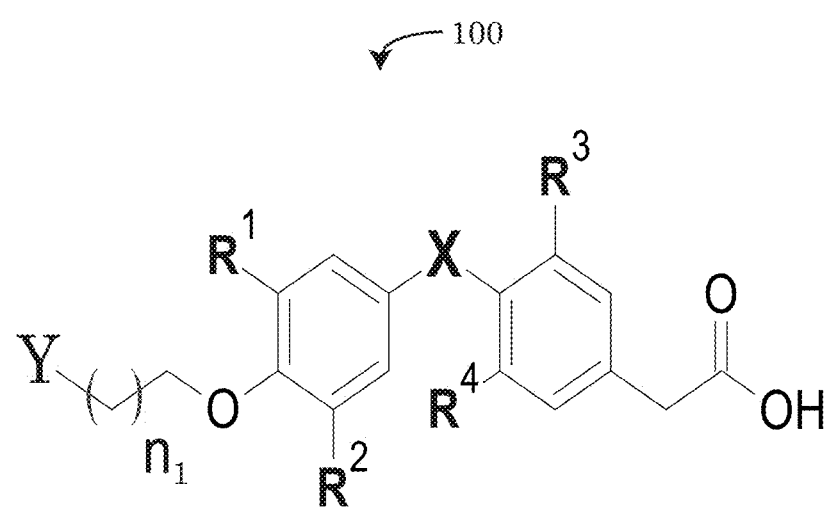
FIG. 1 depicts an embodiment of a general chemical formula describing a thyroid antagonist and derivatives thereof.

A detailed description of the hereinafter-described embodiments of the disclosed apparatus and method are presented herein by way of exemplification and not limitation with reference made to the Figures. Although certain embodiments are shown and described in detail, it should be understood that various changes and modifications might be made without departing from the scope of the appended claims. The scope of the present disclosure will in no way be limited to the number of constituting components, the materials thereof, the shapes thereof, colors thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Overview

Embodiments of the present disclosure describe new chemical compositions, and methods of synthesis thereof. The compositions disclosed and described herein may be directed toward and classified as anti-angiogenic agents, which may be capable of reacting with one or more cell surface receptors of the integrin $\alpha v\beta 3$ receptor family. The compositions described herein may include an anti-angiogenic thyroid hormone or derivative thereof conjugated via a non-cleavable linker to a polymer, forming a single chemical entity which may considered a micro molecule or macromolecule (depending on the size of the polymer covalently bound to the thyroid hormone or derivative thereof). The size of the single chemical entity and the strength of the non-cleavable covalent bond may be advantageous for preventing the thyroid hormone or derivative thereof from entering cells comprising a cell surface receptor of the integrin $\alpha v\beta 3$ variety. Due to the size of the attached polymer, and the inability of the surrounding environment of the cell to cleave the strong, uncleavable covalent bonds of the thyroid hormone from the polymer, the thyroid hormone portion of the described chemical entities may be unable to be internalized within the nucleus of the cells which the thyroid hormone or derivative thereof may interact. Accordingly, the thyroid hormone portion of the described chemical entities may interact with the cells non-genomically and avoid genomic interactions that may be caused by thyroid hormones or derivatives thereof entering a cell and interacting with the nuclear receptors of the cellular nucleus.

Embodiments of the compositions disclosed herein may be synthesized to include, but are not limited to entities comprising non-biodegradable polymers such as polyethylene glycol (PEG) (1,000-15,000 Daltons, for example between 4,000-8,000 Daltons), $\alpha$, $\beta$, or $\gamma$cyclodextrins, chitosan, alginic acid or hyaluronic acid, conjugated via non-cleavable linker comprising an amine or triazole bond, without short chain of PEG (100-800 M.W.) to an $\alpha v\beta 3$ thyroid antagonist. Embodiments of the thyroid antagonists conjugated to the polymers may include tetraiodothyroacetic acid (tetrac), triiodothyroacetic acid (triac), derivatives thereof and variations thereof. Examples of one or more variations of the thyroid hormone antagonists comprising tetrac and triac may include, in some embodiments Diaminotetrac (DAT) or Diamnotriac (DATri) (hereinafter may be referred to interchangeably as "DAT"), Monoaminotetrac (MAT) or Monoaminotriac (MATri) (hereinafter referred to interchangeable as "MAT"), Triazoletetrac (TAT) or Triazoletriac (TATri) (hereinafter referred to interchangeable as "TAT"), derivatives thereof or other thyroid antagonist known by those skilled in the art.

Embodiments of the compositions described herein have been further synthesized and characterized as DAT, MAT or TAT conjugated to different molecular weights of Polyethylene Glycol (1,000 to 15,000 Dalton). We have scaled up embodiments of the relatively most soluble, PEG-DAT (P-Mono-DAT, P-bi-DAT) and PEG-TAT (P-Mono-TAT, P-bi-TAT), for biological characterization in various in vitro and in vivo biological systems. Chemical labelling of DAT or TAT and PEG-DAT or PEG-TAT as well as C-DAT and C-TAT for imaging and cellular kinetics. Data revealed that polymer conjugation to DAT or TAT resulted in the restriction of cell nuclear uptake of those polymers conjugated DAT or TAT versus intense cell nuclear uptake of DAT or TAT. The result of this unique cellular distribution lead to the lack of genomic action of the polymer conjugated DAT, MAT or TAT versus the non-conjugated ones. Other Polymers such as Hyaluronic, Alginic acid, Chitosan conjugated to DAT, MAT or TAT with or without short chain short chain PEG (100-1,000 Dalton) are described. Additional Polymer conjugation to DAT, MAT or TAT were synthesized using bi-functional or tetra-function PEG may include, but it could also include other branched PEG up to 8 chains.

Embodiments of each of the compounds described in the current application may multiple types of utility for treating a plurality of different diseases modulated by angiogenesis or the inhibition thereof. Each of the compositions described in the present disclosure, in view of presence of the thyroid antagonist present in the described compositions, may each have an affinity for targeting the integrin receptor $\alpha v\beta 3$ located on numerous types of cells found throughout the human body and various animal bodies.

For example, the utility of the compositions disclosed herein may be useful for treating angiogenesis-mediated disorders such as Cancer (Solid tumors and Liquid tumors) in humans or mammals. Cancers may include Glioblastoma, pancreatic, ovarian, breast, prostate, bladder, lung and liver cancer. Liquid tumors may also acute myeloid leukemia, multiple myeloma, Lymphoma and chronic lymphocytic leukemia. The compositions described herein may further treat ocular disorders (Diabetic Retinopathy and Age-related Macular Degeneration), inflammatory disorders (arthritis, osteoarthritis), atherosclerosis lesions, and dermatology (Rosacea, Psoriasis, skin cancer) which may each be mediated or dependent upon the generation of new blood cells via angiogenesis to persist and the treatment thereof may be dependent antagonizing the formation of new blood vessel to slow or eliminate the angiogenic pathways.

While embodiments and examples of the present disclosure described herein, for purposes of illustration, modifications and changes will become apparent to those skilled in the art based on the examples illustrated. Accordingly, the appended examples intended to encompass all variations and such modifications and changes that fall within the true spirit and scope of this disclosure.

Thyrointegrin Antagonist Compositions

Referring to the drawings, FIG. 1 depicts an embodiment of a general formula 100 describing a thyroid hormone antagonist attached to a linker comprising a repeating linkage of carbon atoms which may be defined by $n_1$ carbon subunits and "Y" which may define a non-cleavable covalent bond attached to the linker of the thyroid hormone antagonist and derivatives thereof of the general formula 100. The term "thyroid hormone antagonist" may describe the ability of a molecule of general formula 100 to inhibit or antagonize one or more thyroid hormone receptors known by a person skilled in the art, for example the integrin family of thyroid hormone receptors, such as the thyroid hormone cell surface receptor αvβ3. Due to the functionality of the thyroid hormone antagonist and derivatives thereof to inhibit integrin receptors, the molecule defined by the general formula 100 may further be described herein as a thyrointegrin antagonist.

As shown by the chemical structure of the general formula 100 of FIG. 1, embodiments of the chemical structure may include one or more variables defining the additional features of the thyrointegrin antagonist of FIG. 1. For example, in some embodiments of the thyrointegrin antagonist, the variables depicted as $R^1$, $R^2$, $R^3$ and $R^4$ may be each independently be substituted for molecules of hydrogen, iodine, linear alkanes, branched alkanes and cyclic alkanes. In some embodiments, the variable "X" may be defined as an oxygen atom (O) or a sulfur atom (S).

Embodiments of the carbon linker connected to the thyroid antagonist of the general formula 100 may be variable in the length of the carbon chain. The length of the carbon chain may be as small as one carbon atom between oxygen molecule and the non-cleavable covalent bond "Y". In alternative embodiments of the thyrointegrin antagonist, the linker may comprise repeating links of carbon atoms, which may be defined by $n_1$ repeats. $n_1$ may be $\geq 0$ in some embodiments, while in alternative embodiments of the general formula 100, the repeating number of carbon atoms in the linker of $n_1$ may be $\geq 0$, $\geq 1$, $\geq 2$ or $\geq 3$.

Embodiments of the non-cleavable covalent bond, depicted by the variable "Y", may in some instances be may be an amine bond. For example, the variable Y of the general formula may be a monoamine having one amine group or a diamine having two amine groups in the non-cleavable covalent bond as shown by the examples of thyrointegrin antagonists 210, 215, 220, 225, 310, 320, 410, 420 of FIGS. 2a-2b, 2d-2e, 3a-3b, 4a-4b. In alternative embodiments, the substituted variable Y may include a propargyl group as shown in shown in FIGS. 2c, 2f, 3c and 4c.

As demonstrated by the embodiments of FIG. 2a-4c, there is a wide range of derivative compositions that may be formed from the general formula 100. For example, in FIG. 2a, the composition 210 may comprise a substitution of iodine for $R^1$-$R^4$, resulting in the formation of a tetraiodothyroacetic acid (tetrac) derivative having a three-carbon linker and a monoamine as the non-cleavable covalent bond. Composition 210 may be referred to as monoamine-tetrac (MAT). Likewise, in FIG. 2b, the tetrac molecule further comprises a diamino covalent bond connected to the linker. Likewise, this composition 220 may be referred to a diamino tetrac (DAT). In the alternative embodiment of FIG. 2c, the composition 230 may comprise a propargyl group attached to a one-carbon linkage between the tetrac molecule and propargyl group as shown. This derivative composition 230 may be referred to as propargyl tetrac (PGT).

Synthesis of Propargylated Tetrac (PGT) from Tetrac

Figure 19:
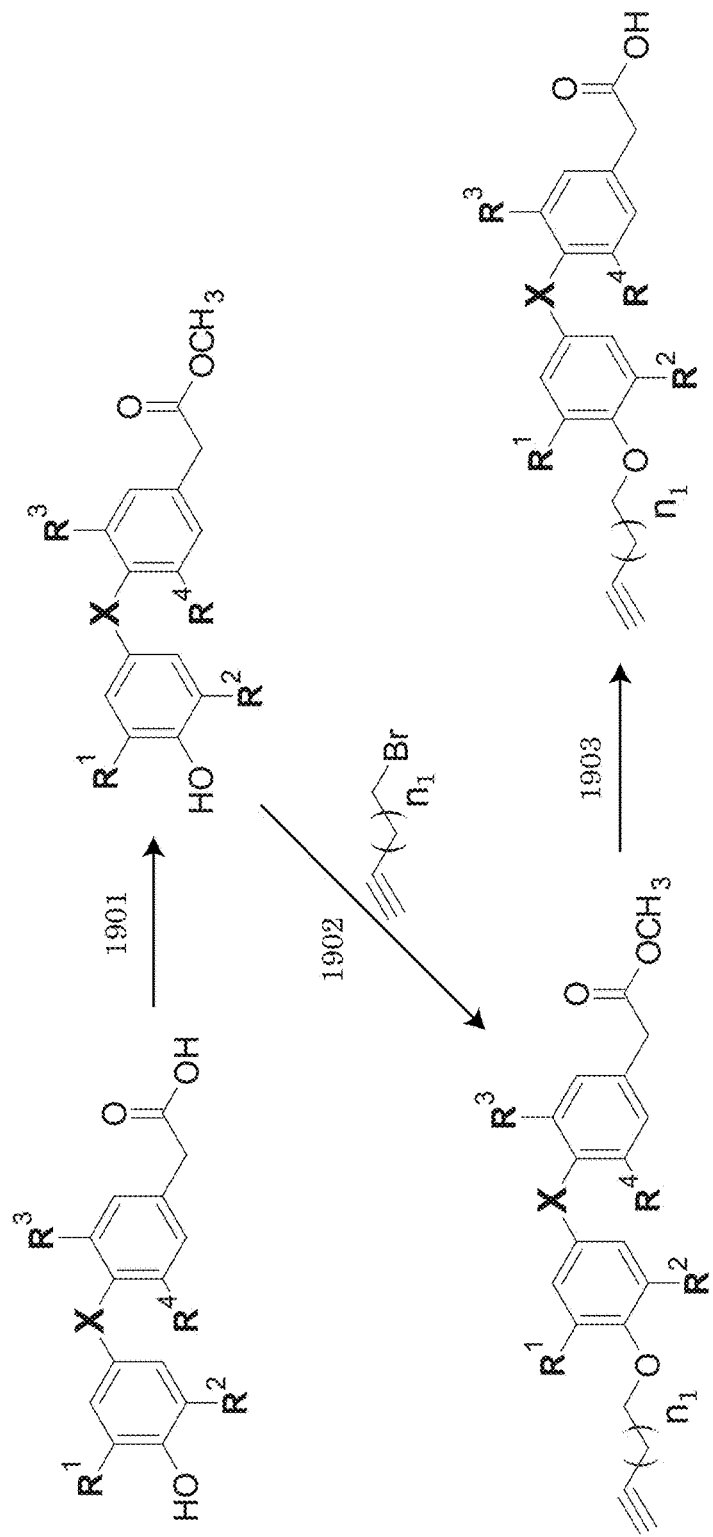
FIG. 19 depicts an embodiment of a method for synthesizing a thyrointegrin antagonist having a linker comprising a propargyl group.
Figure 20:
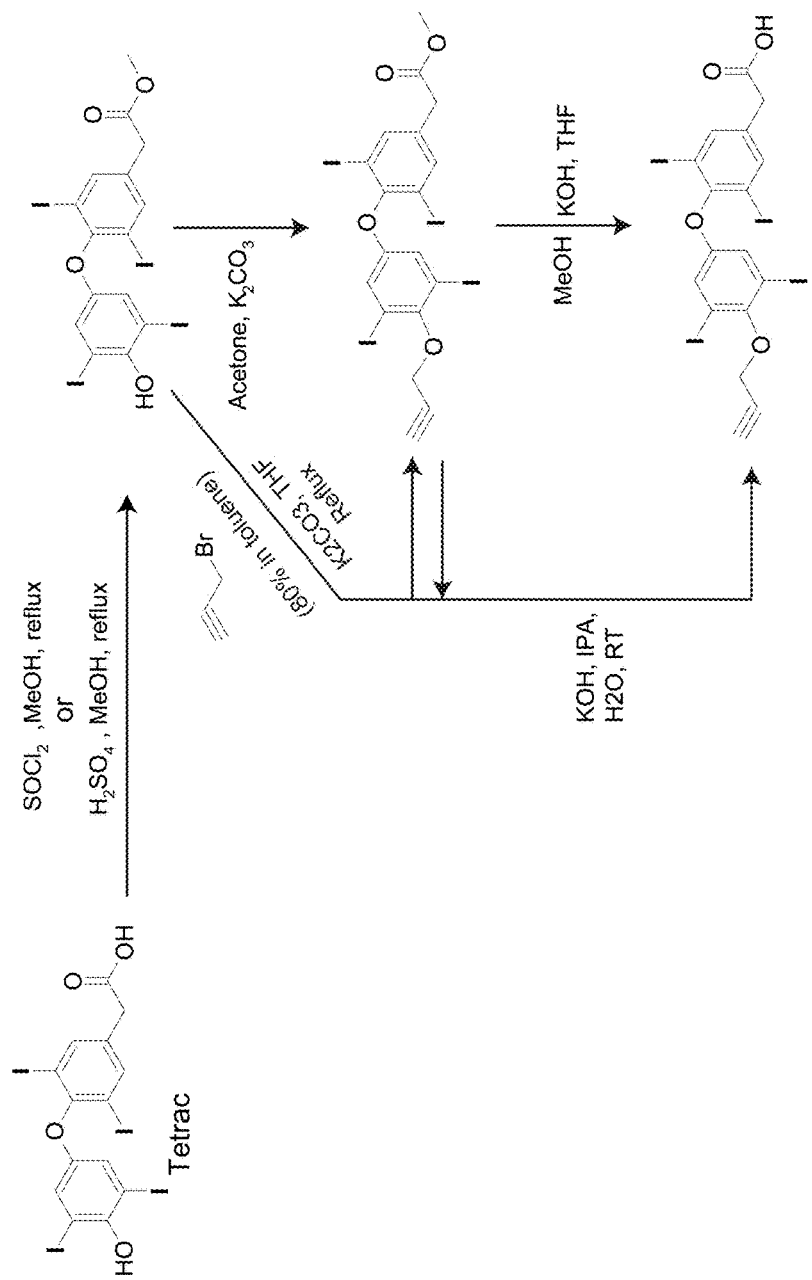
FIG. 20 depicts an embodiment of a method for synthesizing propargylated tetrac (PGT).

The following example provides a sample method for preparing propargyl tetrac or a derivative thereof from tetrac in accordance with the general chemical formula described in FIG. 19 and more specifically as applied to tetrac as shown in the synthesis diagram of FIG. 20.

Step 1: Esterification

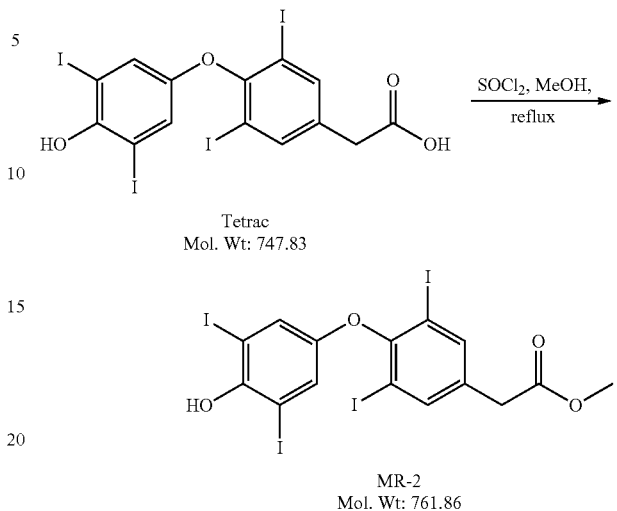

Table 1a provides the synthesis conditions for esterifying tetrac into O-methyl tetrac (MR-2) (methyl-2-(4-(4-hydroxy-3, 5-diiodophenoxy)-3, 5-diiodophenyl) acetate):

| Batch No. | Input (g) | Output (g) | Reagents | Yield (%) | Purity by HPLC (% a/a) |
|---|---|---|---|---|---|
| 01 | 10 | 9.3 | SOCl$_2$ (2.5 eq.), MeOH (37.5 vol.) | 92 | 98.67 |
| 02 | 10 | 9.5 | SOCl$_2$ (2.5 eq.), MeOH (25 vol.) | 94 | $^1$H NMR recorded and compared |
| 03 | 200 | 194 | SOCl$_2$ (2.5 eq.), MeOH (25 vol.) | 95 | 99.15 |

In one embodiment for synthesizing MR-2, the composition is synthesized according to the protecting method previously published. A solution of tetraiodothyroacetic acid (1 g, 1.33 mmol, 1 equiv.) and boron tri-fluoride diethyl ether (BF$_3$·Et$_2$O) (0.1 mL) in methanol (10 mL) stirred under nitrogen at ambient temperature for 24 hours. Reaction quenched by adding 15 ml saturated aqueous NaHCO$_3$ solution and mixture stirred for 10 minutes, and the aqueous phase extracted with ethyl acetate (3×20 mL). The combined organic phases were dried with sodium sulfate, filtered, and concentrated under vacuum to afford 950 mg crude methyl-2-(4-(4-hydroxy-3,5-diiodophenoxy)-3,5-diiodophenyl)acetate 2, which was then recrystallized by ethanol to give pure compound (630 mg, 0.82 mmol) with 62% yield. Recrystallization solvent: EtOH; R$_f$: 0.62 with TLC solvent (n-Hexane: EtOAc/8:2); mp=162-4° C.; FTIR (υ cm$^{-1}$): 3371, 3082, 2943, 1719 cm$^{-1}$ (C═O), 1586, 1556, 1539, 1455, 1430, 1397, 1283, 1240, 1220, 1160, 1238, 912, 847, 823, 782, 700, 597, 527. $^1$H NMR (CDCl$_3$) δ (ppm): 7.78 (s, 2H, ArH), 7.12 (s, 2H, ArH), 5.53 (br, 1H, OH), 3.75 (s, 3H, —COOCH$_3$), 3.58 (s, 2H, —CH$_2$—COO); $^{13}$C NMR (CDCl$_3$) δ (ppm): 171.0 (—COOMe), 152.8, 150.2, 149.6, 141.3, 135.2, 126.1, 90.9, 81.8, 52.7 (—COOCH$_3$), 39.8 (—CH$_2$—COO). MS (ESI$^+$) m/z: 785 [M+Na]$^+$; (ESI$^-$) m/z: 761 [M-H$^-$].

Step 2: Alkylation

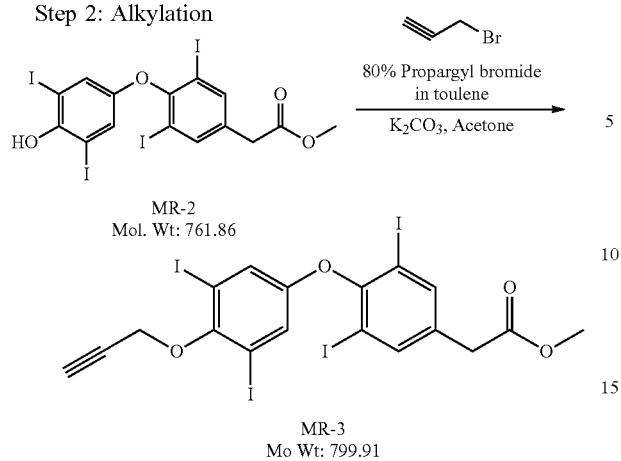

MR-2
Mol. Wt: 761.86

MR-3
Mo Wt: 799.91

TABLE 1B

Synthesis Conditions for MR-3 (methyl {4-[3,5-diiodo-4-(prop-2-yn-1-yloxy) phenoxy]-3,5-diiodophenyl} acetate)

| Batch. No. (NNA-P-16-01-II-XX) | Input (g) | Output (g) | Reagents | Temp °C./Time h | Yield (%) | Purity by HPLC (% a/a) | Impurity 1.02 RRT |
|---|---|---|---|---|---|---|---|
| 04 | 10.0 | 8.6 g | 80% Propargyl bromide (3.0 eq.), $K_2CO_3$ (5.0 eq.) | 55-60/24 | 82.7 | 71.12 | 27.41 |
| 08 | 10.0 | 9.4 | 80% Propargyl bromide (3.0 eq.), $K_2CO_3$ (5.0 eq.) | 55-60/1 | 89.5 | 97.7 | 1.12 |
| 09 | 1.0 | 0.94 | 80% Propargyl bromide (3.0 eq.), $K_2CO_3$ (5.0 eq.) | 25-35/1.5 | 90 | 94.72 | 4.19 |
| 12 | 1.0 | 0.94 | 80% Propargyl bromide (1.0 eq.), $K_2CO_3$ (5.0 eq.) | 25-35/1.5 | 90.38 | 96.61 | 0.8 |
| 13 | 1.0 | 0.71 | 80% Propargyl bromide (1.0 eq.), $K_2CO_3$ (5.0 eq.) | 0-5/1.5 | 68.12 | 98.53 | 0.28 |
| 14 | 30 | 25 | 80% Propargyl bromide (1.0 eq.), $K_2CO_3$ (5.0 eq.) | 0-5/12 | 79.13 | 96.97 | N/A |
| 15 | 70 | 67 | 80% Propargyl bromide (1.0 eq.), $K_2CO_3$ (5.0 eq.) | 0-5/72 | 91.1 | 97.32 | 0.31 |
| 16 | 70 | 67 | 80% Propargyl bromide (1.0 eq.), $K_2CO_3$ (5.0 eq.) | 0-5/120 | 91.1 | 98.96 | N/A |

In one embodiment, the step of alkylation may be performed A mixture of methyl-protected tetrac (1 eq) and propargyl bromide (3 eq) and potassium carbonate (5 eq) in 25 ml acetone was heated at reflux for 24 hours. The reaction was filtered, concentrated, and then crude purified with flash column chromatography over silica gel using n-hexane and ethyl acetate (9:1 to 7:3) to give methyl {4-[3,5-diiodo-4-(prop-2-yn-1-yloxy)phenoxy]-3,5-diiodophenyl}acetate with 78-85% yield. $^1$H NMR (CDCl$_3$) δ (ppm): 7.76 (s, 2H, ArH), 7.16 (s, 2H, ArH), 4.6 (br, 1H, OH), 3.75 (s, 3H, —COOCH$_3$), 3.56 (s, 2H, —CH$_2$—COO); 2.54 (s, 2H, —O—CH$_2$—C—CH).

Step 3: Hydrolysis

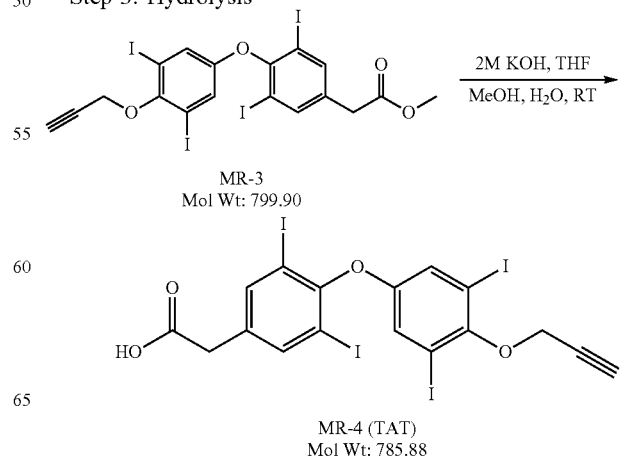

MR-3
Mol Wt: 799.90

MR-4 (TAT)
Mol Wt: 785.88

TABLE 1C

Synthesis Conditions for MR-4 {4-[3,5-diiodo-4-(prop-2-yn-1-yloxy)phenoxy]-3,5-diiodophenyl} acetic acid

| NNB- | Input (g) | Output (g) | Reagents | Yield (%) | Purity by HPLC (% a/a) | Comments |
|---|---|---|---|---|---|---|
| 07 | 1.0 | 0.76 | 2M KOH (60 vol.), 1:1 Methanol:THF (60 vol.), | 77 | 72.47 | familiarization |
| 10 | 1.0 | 0.71 | | 74 | 95.66 | SM ester and ether of tetrac |
| 17 | 65 | 62.1 | | 97 | 97.9 | Input material (MR-3) purity 97.3% |
| 18 | 65 | 61.8 | 1M HCl. (83 vol.), Water (15.4 vol.) | 97 | 97.94 | Input material(MR-3) purity 98.6% |

The compound PGT 230 may be obtained by de-protection of compound MR-3 using KOH. Briefly, 100 mg of compound MR-3 was dissolved in 6 ml of THF/methanol (1:1). The mixture was stirred for 15 min and then 6 ml of KOH 2M was added and the reaction was allowed to stir for 18 hours at room temperature. Organic solvent was evaporated completely and neutralized by HCl 1M. The precipitate was collected by vacuum filtration, washed with water several times, and dried overnight to give 83% of white powder of PGT 230 Dichloromethane/methanol (9:1) used as solvent for TLC. 1H NMR (CDCl$_3$) δ (ppm): 7.85 (s, 2H, ArH), 7.16 (s, 2H, ArH), 4.6 (br, 1H), 3.56 (s, 2H, —CH2-COO); 2.96 (s, 2H, —O—CH2-C—CH).

Figure 2A:
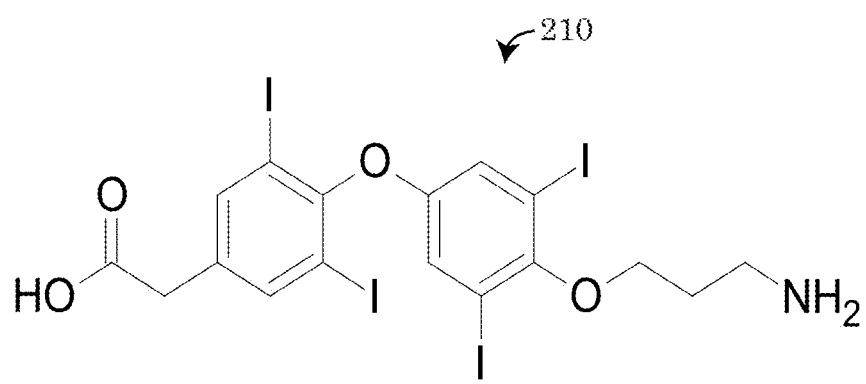
FIG. 2a depicts an embodiment of a tetraiodothyroacetic acid (tetrac) derivative, monamino propyl tetrac (MAT).
Figure 2B:
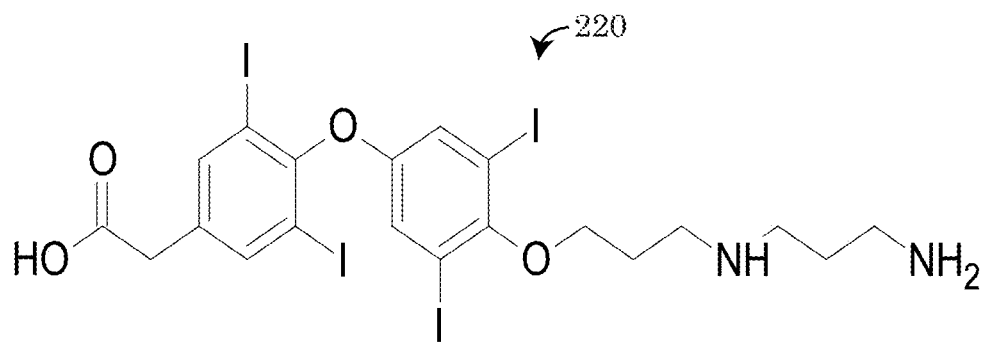
FIG. 2b depicts an embodiment of a tetrac derivative, diamino propyl tetrac (DAT).
Figure 2C:
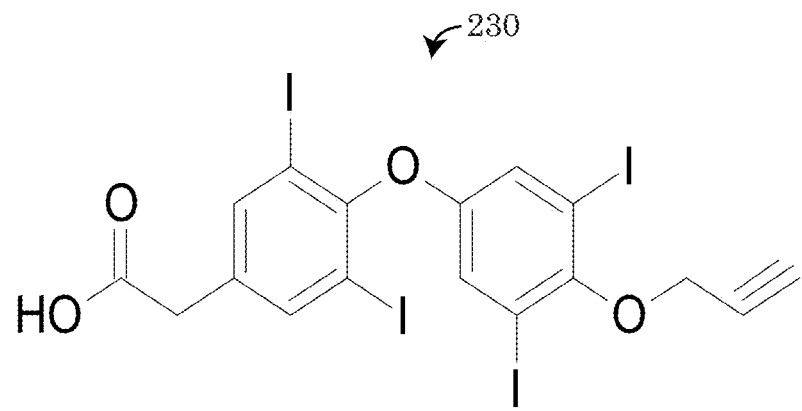
FIG. 2c depicts an embodiment of a tetrac derivative, propargyl tetrac (PGT).
Figure 2D:
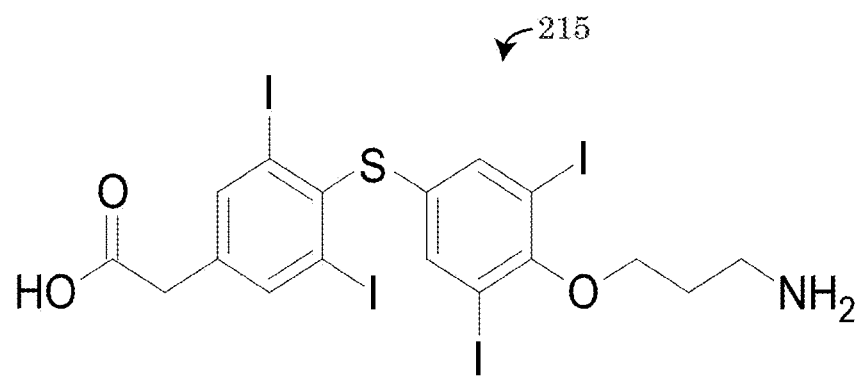
Figure 2E:
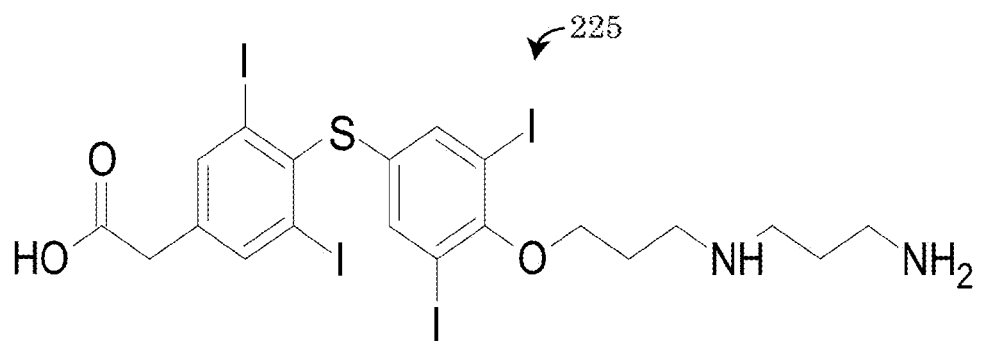
FIG. 2e depicts an alternative embodiment of the tetrac derivative of FIG. 2b.
Figure 2F:
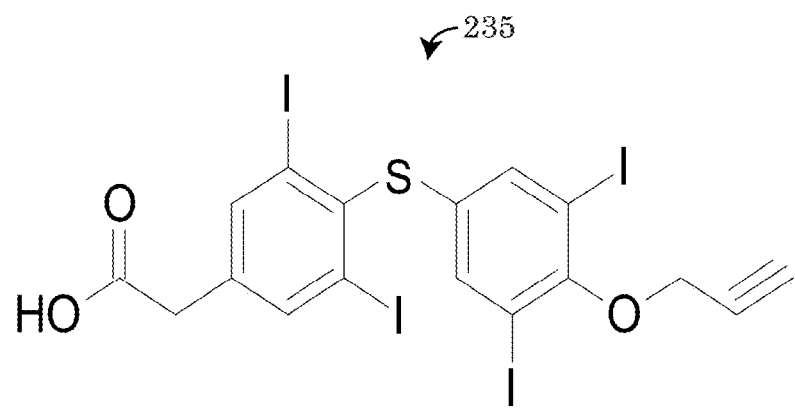
FIG. 2f depicts an alternative embodiment of the tetrac derivative of FIG. 2c.
Figure 3A:
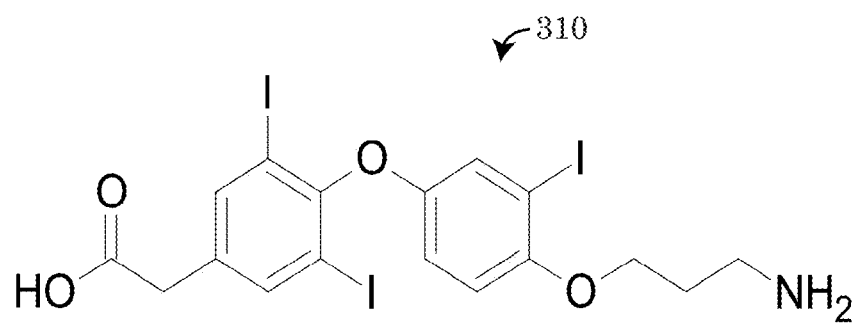
FIG. 3a depicts an embodiment of a triiodothyroacetic acid (triac) derivative, monoamino propyl triac (MATri).
Figure 3B:
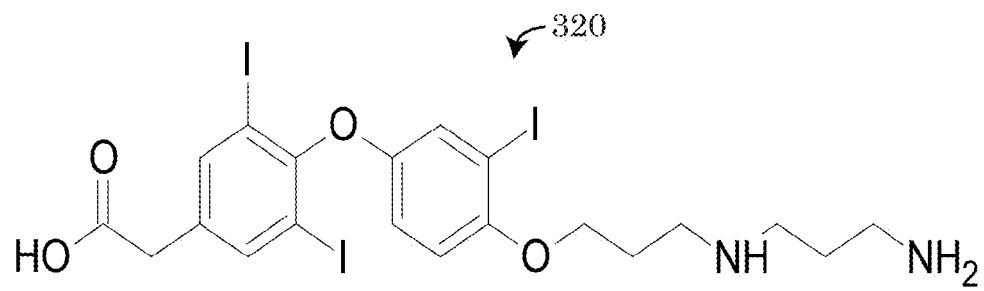
FIG. 3b depicts an embodiment of a triac derivative, diamino propyl triac (DATri).
Figure 3C:
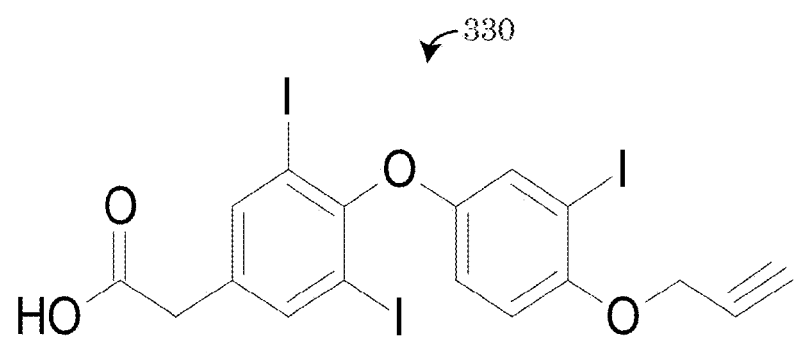
FIG. 3c depicts an embodiment of a triac derivative, propargyl triac (PGTri).
Figure 4A:
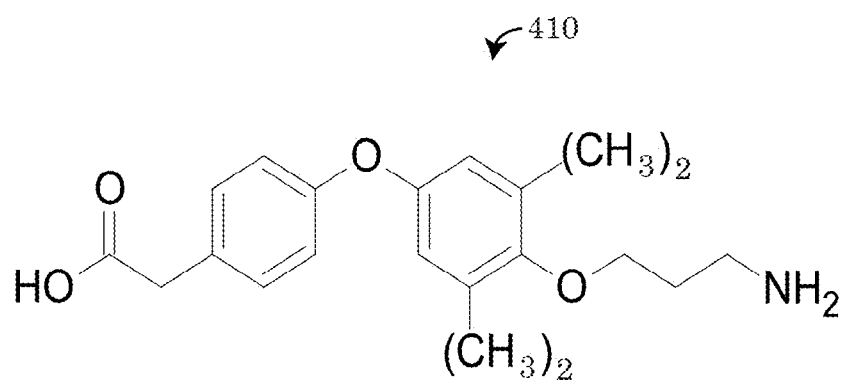
FIG. 4a depicts an embodiment of a thyrointegrin antagonist derivative.
Figure 4B:
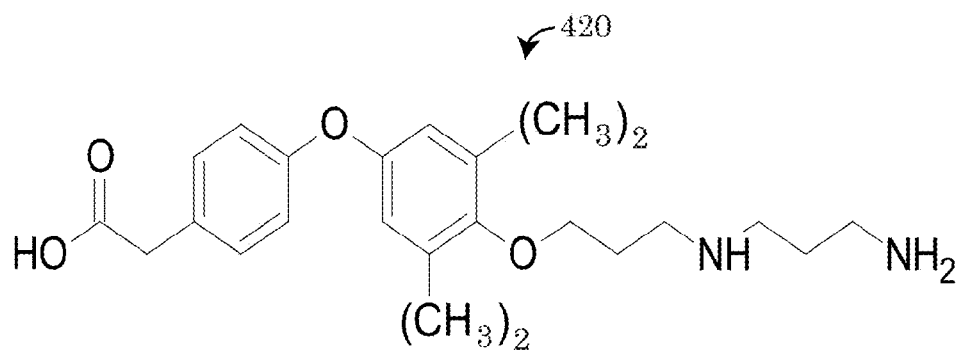
FIG. 4b depicts an alternative embodiment of a thyrointegrin receptor antagonist derivative.
Figure 4C:
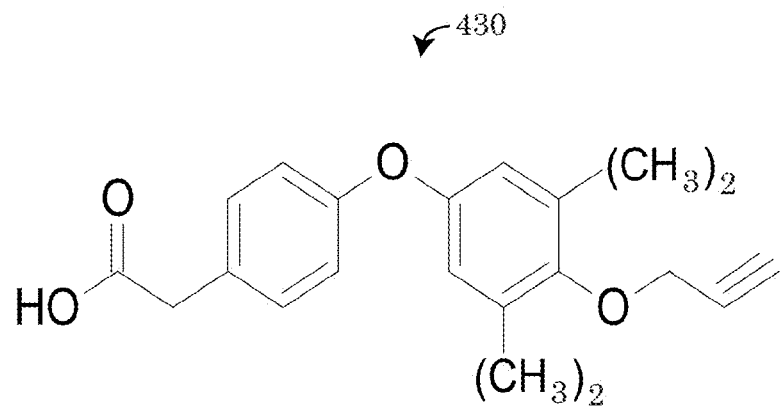
FIG. 4c depicts another alternative embodiment of thyrointegrin antagonist derivative.

Referring to the drawings, the embodiments of FIG. 2d-2f demonstrate chemical formulas of the tetrac derivatives of FIG. 2a-2c. However instead of the variable X comprising oxygen, the derivative compositions 215, 225 and 235 each comprise a sulfur substituted for variable X. Similar to the compositions 215, 225, 235 depicted in FIGS. 2d-2f, the derivatives 310, 320 and 330 describe another variation of the general formula 100. In the embodiments of FIG. 3a-3c, the thyrointegrin antagonist depicted substitutes R$^4$ with a hydrogen, while R$^1$-R$^3$ are substituted with iodine. Accordingly, because of the substitution of three iodine and a hydrogen, the thyroid antagonist shown in FIG. 3a-3c may be triiodothyroacetic acid (triac) rather than tetrac. The compositions 310, 320 and 330 may summarily be identified as the derivatives monoamino-triac 310, diamino triac 320 and propargyl triac 330. In embodiments of the thyrointegrin antagonists, the derivatives of the thyroid antagonist use may not include an iodine, as opposed to the examples provided in FIGS. 2a-3c. The embodiments of FIG. 4a-4c demonstrate a thyrointegrin antagonist 410, 420, 430, wherein R$^1$-R$^2$ are each substituted with a hydrogen and R$^3$-R$^4$ are each substituted with an isopropyl group.

Table 2 provided below describes a plurality of different substitutions that may be made into the variables of the general formula 100:

TABLE 2

Substitutions of the general formula for a thyrointegrin antagonists, wherein $n_1 \geq 0$

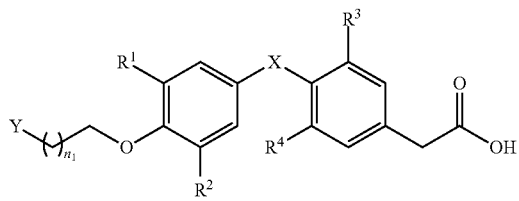

| Y | X | R$^1$ | R$^2$ | R$^3$ | R$^4$ |
|---|---|---|---|---|---|
| Amine, diamine or propargyl | O or S | H | H | H | H |
| Amine, diamine or propargyl | O or S | I | H | H | H |
| Amine, diamine or propargyl | O or S | H | I | H | H |
| Amine, diamine or propargyl | O or S | H | H | I | H |
| Amine, diamine or propargyl | O or S | H | H | H | I |

TABLE 2-continued

Substitutions of the general formula for a thyrointegrin antagonists, wherein $n_1 \geq 0$

| Y | X | R$^1$ | R$^2$ | R$^3$ | R$^4$ |
|---|---|---|---|---|---|
| Amine, diamine or propargyl | O or S | I | I | H | H |
| Amine, diamine or propargyl | O or S | I | H | I | H |
| Amine, diamine or propargyl | O or S | H | H | I | I |
| Amine, diamine or propargyl | O or S | I | I | I | H |
| Amine, diamine or propargyl | O or S | H | I | I | I |
| Amine, diamine or propargyl | O or S | I | I | I | I |
| Amine, diamine or propargyl | O or S | H | H | H | H |
| Amine, diamine or propargyl | O or S | isopropyl | H | H | H |
| Amine, diamine or propargyl | O or S | H | isopropyl | H | H |
| Amine, diamine or propargyl | O or S | H | H | isopropyl | H |
| Amine, diamine or propargyl | O or S | H | H | H | isopropyl |
| Amine, diamine or propargyl | O or S | isopropyl | isopropyl | H | H |
| Amine, diamine or propargyl | O or S | isopropyl | H | isopropyl | H |

TABLE 2-continued

Substitutions of the general formula for a thyrointegrin antagonists, wherein $n_1 \geq 0$

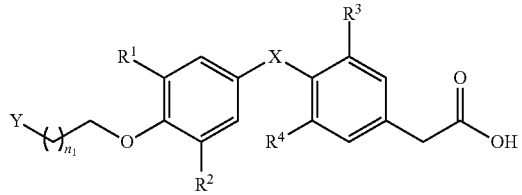

| Y | X | $R^1$ | $R^2$ | $R^3$ | $R^4$ |
|---|---|---|---|---|---|
| Amine, diamine or propargyl | O or S | H | H | isopropyl | isopropyl |
| Amine, diamine or propargyl | O or S | isopropyl | isopropyl | isopropyl | H |
| Amine, diamine or propargyl | O or S | H | isopropyl | isopropyl | isopropyl |
| Amine, diamine or propargyl | O or S | isopropyl | isopropyl | isopropyl | isopropyl |
| Amine, diamine or propargyl | O or S | tert-butyl | H | H | H |
| Amine, diamine or propargyl | O or S | H | tert-butyl | H | H |
| Amine, diamine or propargyl | O or S | H | H | tert-butyl | H |
| Amine, diamine or propargyl | O or S | H | H | H | tert-butyl |
| Amine, diamine or propargyl | O or S | tert-butyl | tert-butyl | H | H |
| Amine, diamine or propargyl | O or S | tert-butyl | H | tert-butyl | H |
| Amine, diamine or propargyl | O or S | H | H | tert-butyl | tert-butyl |

TABLE 2-continued

Substitutions of the general formula for a thyrointegrin antagonists, wherein $n_1 \geq 0$

[Structure shown: aromatic compound with substituents $R^1$, $R^2$, $R^3$, $R^4$, linker $X$, and Y-(CH$_2$)$_{n_1}$-O- group, terminating in -CH$_2$-C(=O)-OH]

| Y | X | $R^1$ | $R^2$ | $R^3$ | $R^4$ |
|---|---|---|---|---|---|
| Amine, diamine or propargyl | O or S | C(CH$_3$)$_3$ | C(CH$_3$)$_3$ | C(CH$_3$)$_3$ | H |
| Amine, diamine or propargyl | O or S | H | C(CH$_3$)$_3$ | C(CH$_3$)$_3$ | C(CH$_3$)$_3$ |
| Amine, diamine or propargyl | O or S | C(CH$_3$)$_3$ | C(CH$_3$)$_3$ | C(CH$_3$)$_3$ | C(CH$_3$)$_3$ |

Figure 5:
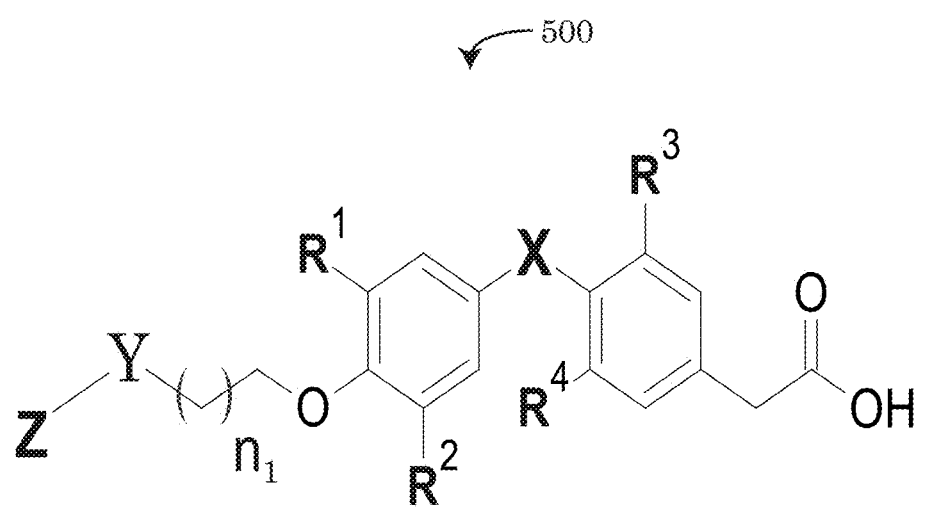
FIG. 5 depicts an embodiment of general chemical formula describing a thyroid hormone antagonist derivative conjugated to a polymer via a non-cleavable bond.
Figure 6:
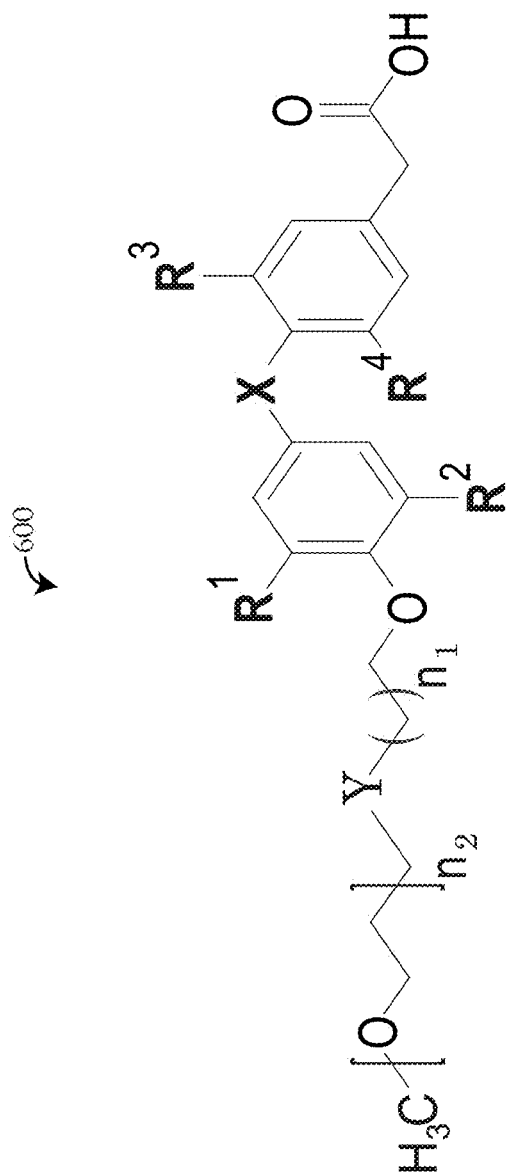
FIG. 6 depicts an embodiment of a general formula of a thyroid hormone antagonist derivative conjugated via a non-cleavable bond to a polyethylene glycol (PEG) polymer.

In some embodiments of the thyrointegrin antagonists of the current disclosure, the thyrointegrin antagonist of the general formula 100 may be conjugated, via the non-cleavable covalent bond of variable Y, to a non-biodegradable polymer (variable Z) as depicted by the general formula disclosed by embodiment 500 of FIG. 5. Suitable polymers that may be substituted for variable Z may include but are not limited to polyethylene glycol (PEG), α-cyclodextrin, β-cyclodextrin, γ-cyclodextrin, chitosan, alginic acid and hyaluronic acid, a combination of polymers thereof or any other non-cleavable polymer known or used by a person skilled in the art. The derivative 600 of the thyrointegrin antagonist depicts an example of a substitution of a PEG polymer for variable Z into the general embodiment of embodiment 500, wherein the PEG polymer has one or more repeating monomeric subunits as defined by the variable $n_2$. For instance, the variable $n_2$ may be any number of repeating monomer≥1. The size of the PEG may vary depending on the number of repeating number of monomers in the PEG's chain. For example, in some embodiments, the size of the PEG may be 1,000-15,000 Daltons in some embodiments, whereas in alternative embodiments, the PEG may be 1000-4,000 Daltons or 4,000 to 6,000 Daltons or more.

Figure 7A:
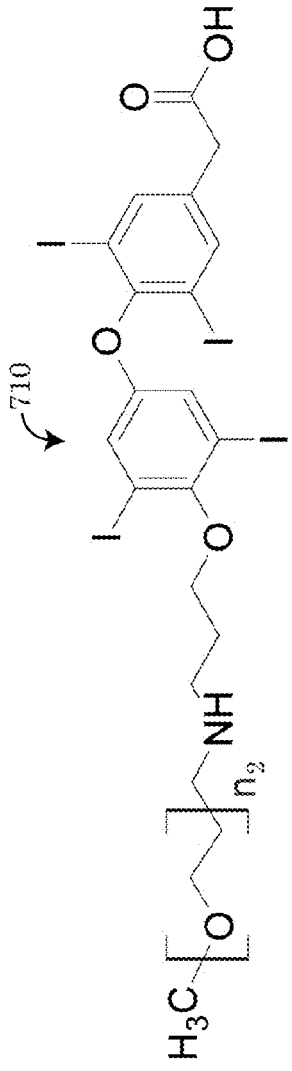
FIG. 7a depicts an embodiment of a thyroid hormone antagonist conjugated to a PEG polymer via a non-cleavable monoamino bond forming PEG-monoamino propyl tetrac (P-MAT).
Figure 7B:
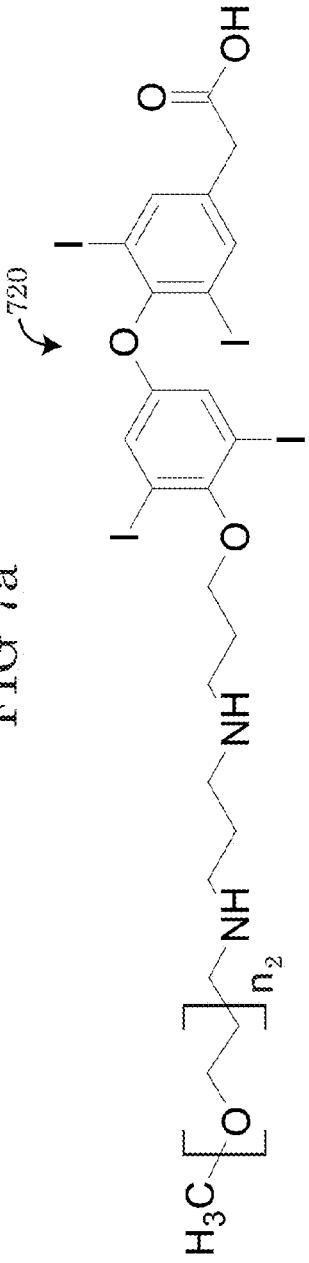
FIG. 7b depict an embodiment of a thyroid hormone antagonist conjugated to a PEG polymer via a non-cleavable diamino bond forming PEG-diamino propyl tetrac (P-DAT).
Figure 7C:
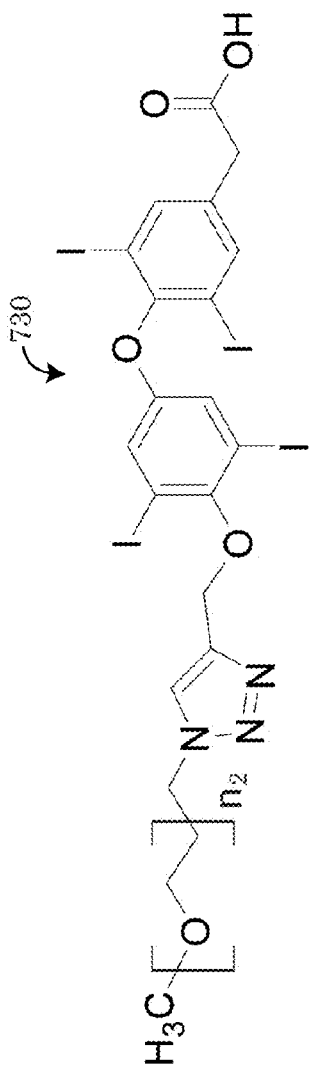
FIG. 7c depict an embodiment of a thyroid hormone antagonist conjugated to a PEG polymer via a non-cleavable N—C bond forming PEG-triazole tetrac (P-TAT).

In the exemplary embodiments of the current application, the thyroid hormone conjugated to the polymer may be tetrac, triac or a derivative thereof as shown in Table 1 above. FIG. 7a-7c depicts the chemical formulas of exemplary embodiments of tetrac conjugated via a non-cleavable covalent bond to the polymer PEG. For example, in FIG. 7a, the drawings depict a thyrointegrin antagonist 710 comprising a tetrac molecule covalently bound via a linker to a PEG polymer via a non-cleavable monoamine bond (N—C Bond). The resulting composition may be described as PEG-monoamino propyl tetrac (P-MAT). In the alternative embodiment 720 of FIG. 7b, the exemplary composition is a tetrac molecule bound via a linker to the PEG polymer via a non-cleavable diamine bond, resulting in a composition, which may be described as PEG-diamino propyl tetrac (P-DAT). In yet a third exemplary embodiment 730, the tetrac may be covalently bound to the PEG polymer via a non-cleavable triazole bond. The resulting composition 730 may be described as PEG-triazole tetrac (P-TAT).

Figure 8:
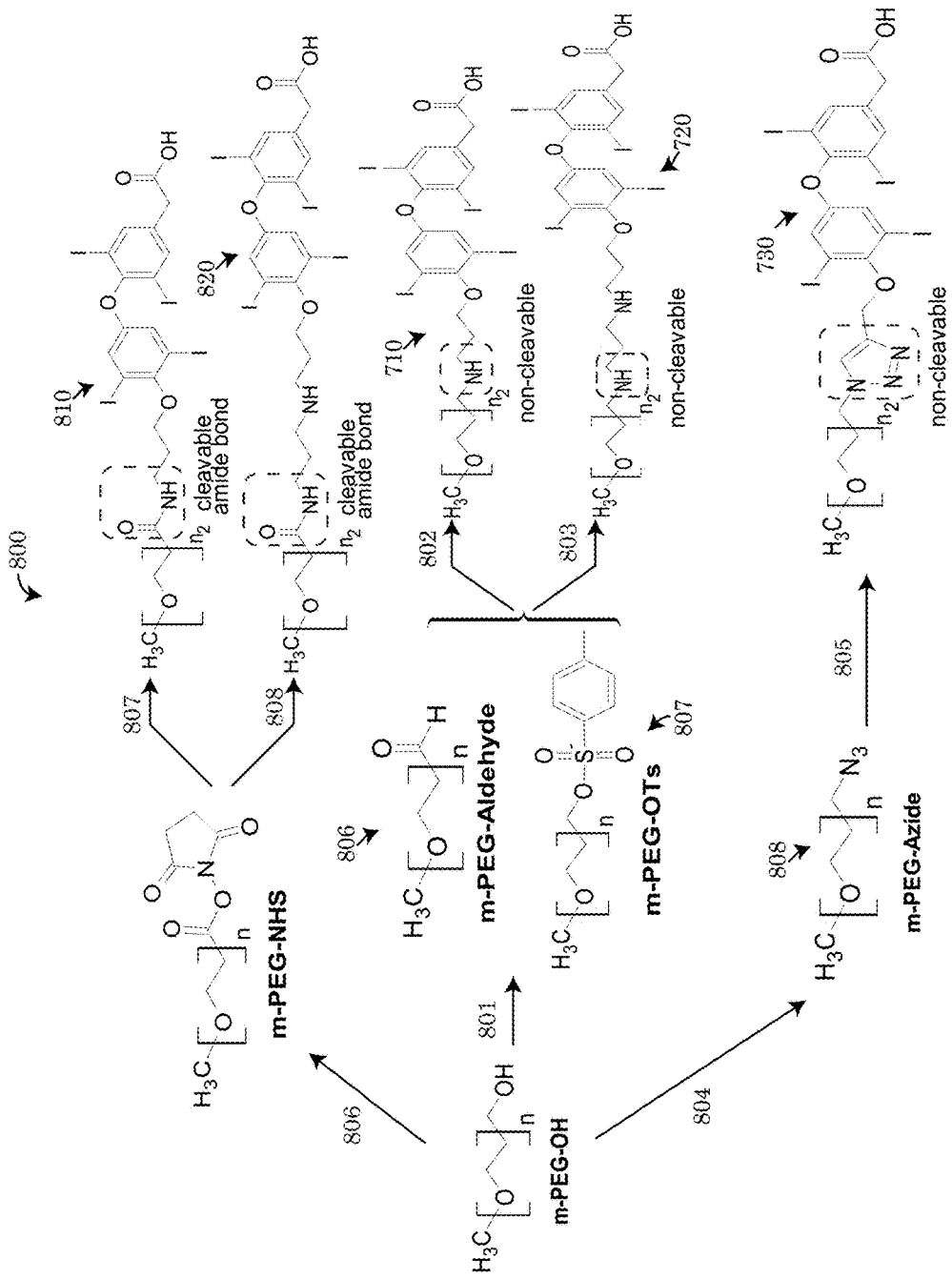
FIG. 8 depicts embodiments of conjugation routes for synthesizing αvβ3 thyroid hormone antagonists via cleavable and non-cleavable linkers using methoxy-polyethylene glycol (mPEG).

FIG. 8 depicts a flow diagram 800 illustrating the one or more steps for conjugating PEG polymers to various active αvβ3 integrin thyroid antagonists via a non-cleavable linker bonded to PEG (1,000-15,000 Daltons), resulting in the formation of P-MAT, P-DAT and P-TAT. In the example methods provided, each composition of the present disclosure depicted using a Monomethoxy PEG as the polymer, a linker and multiple variations of the thyroid antagonist Tetrac, Triac and derivatives, provided during the conjugation steps such as DAT, MAT and TAT.

FIG. 8 depicts steps for creating P-MAT and P-DAT starting with a monomethoxy PEG (m-PEG-OH). Under step 801, the m-PEG-OH may be tosylated forming a mono-tosylated PEG 807 (m-PEG-OTS) and an m-PEG aldehyde 806. In step 802, the mono-tosylated PEG may be introduced to MAT 210 or a derivative thereof in step 802 to form P-MAT 710 through the click chemistry. Similarly, instead of introducing the mono-toslylated PEG 807 to an MAT 310, in step 803 the mono-tosylated PEG 807 may be introduced to a DAT 220 forming P-DAT 720 through the click chemistry as shown.

In order to form P-TAT from the starting monomethoxy-PEG, the mPEG-OH may via step 804 be converted into m-PEG-azide by tosylating the m-PEG-OH to mono-tosylated PEG 807 and converting the mon-tosylated PEG 807 into m-PEG-azide 808 by combining the mono-tosylated PEG 807 with NaN$_3$. The m-PEG-azide 808 may in step 805 combine with a propargyl tetrac 230, creating a triazole bond resulting in P-TAT 730.

It should be noted that for each of the examples provided in the drawings and as described throughout this application, were prepared using commercially available chemicals that have been used without further purification. All solvents were dried and anhydrous solvents were obtained using activated molecular sieves (0.3 or 0.4 nm depending on the type of solvent). All reactions (if not specifically containing water as reactant, solvent or co-solvent) are performed under Ar or $N_2$ atmosphere, in oven-dried glassware. All new compounds gave satisfactory 1H NMR and mass spectrometry results. Melting points were determined on an Electro thermal MEL-TEMP® melting point apparatus and then on a Thomas HOOVER Uni-mel capillary melting point apparatus. Infrared spectra recorded on a Thermo Electron Nicolet Avatar 330 FT-IR apparatus. UV spectra obtained from a SHIMADZU UV-1650PC UV-vis spectrophotometer. The solution-state NMR experiments were all performed a Bruker Advance II 800 MHz spectrometer equipped with a cryogenically cooled probe (TCI) with z-axis gradients (Bruker BioSpin, Billerica, Mass.) at the Center for Biotechnology and Interdisciplinary Studies, Rensselaer Polytechnic Institute (RPI, Troy, N.Y.). All tubes used were 5 mm outside diameter. NMR data were referenced to chloroform (CDCl3; 7.27 ppm 1H, 77.20 ppm 13C) or DMSO-d6 (δ=2.50 ppm, 38.92 ppm 13C) as internal reference. Chemical shifts δ are given in ppm; multiplicities are indicated as s (singlet), d (doublet), t (triplet), q (quartet), m (multiplet) and br (broad); coupling constants, J, are reported in Hz. Thin layer chromatography was performed on silica gel plates with fluorescent indicator. Visualization was accomplished by UV light (254 and/or 365 nm) and/or by staining in ceric ammonium molybdate or sulfuric acid solution. Flash column chromatography performed following the procedure indicated in J. Org. Chem. 43, 14, 1978, 2923-2925, with 230-400 mesh silica gel. High-resolution Mass Spectral analysis performed on either an Applied Biosystems API4000 LC/MS/MS or Applied Biosystems QSTAR XL mass spectrometers.

Figure 9:
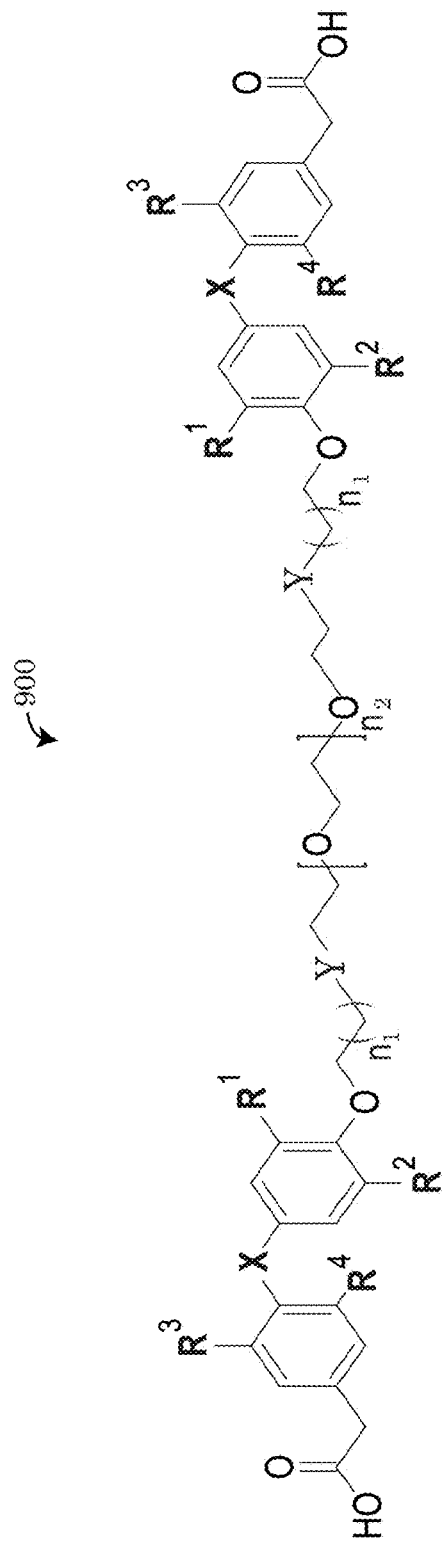
FIG. 9 depicts an embodiment of a general formula of a bifunctional thyrointegrin antagonist derivative comprising two conjugations via a non-cleavable bond to a PEG polymer.
Figure 10A:
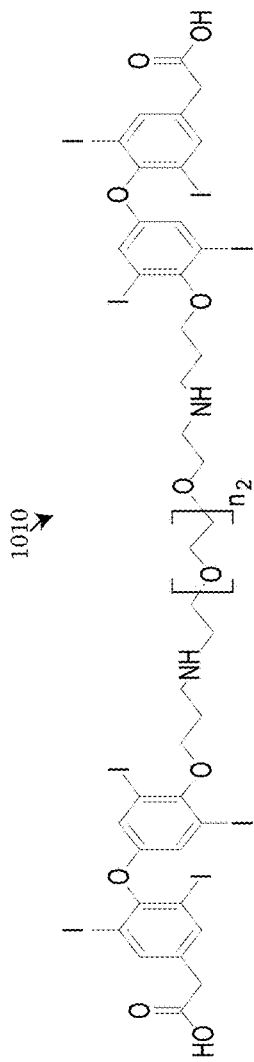
FIG. 10a depicts an embodiment of a bifunctional thyrointegrin antagonist derivative, polyethylene glycol bi-monoamino propyl tetrac (P-bi-MAT).
Figure 10B:
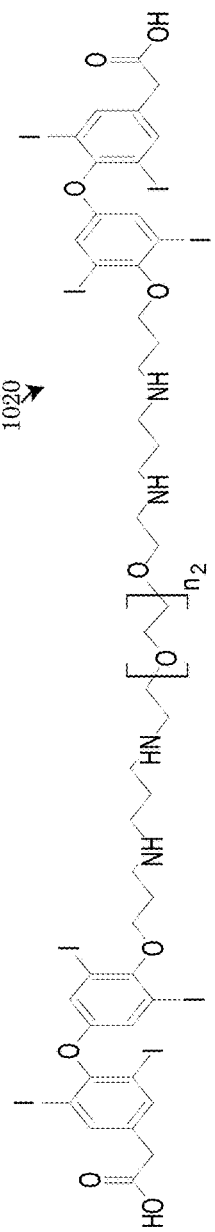
FIG. 10b depicts an embodiment of a bifunctional thyrointegrin antagonist derivative, polyethylene glycol bi-diamino propyl tetrac (P-bi-DAT).
Figure 10C:
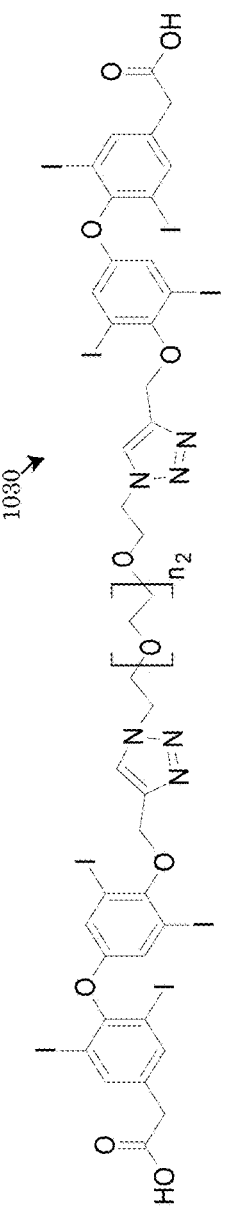
FIG. 10c depicts an embodiment of a bifunctional thyrointegrin antagonist derivative, polyethylene glycol bi-triazole tetrac (P-bi-TAT).

In some embodiments, the polymer-conjugated thyrointegrin antagonists described throughout this disclosure may be bi-functional or tetra-functional compositions. The term "bi-functional" may refer to a polymer conjugated thyroid antagonist having a two thyroid antagonists or derivatives thereof conjugated via a non-cleavable covalent bond to the same polymer (Z) of the general formula 500. One of a bifunctional composition can be seen in FIG. 9, wherein the thyrointegrin antagonist 900 comprises a PEG polymer conjugated on two sides of the embodiment 900 via a carbon atom linker and a non-cleavable bond represented by variable Y to a thyroid hormone antagonist. FIG. 10a-10c provides examples of one or more specific substitutions of the variables depicted in the embodiments 900 of FIG. 9.

For instance, in FIG. 10a, the PEG polymer having one or more repeating subunits denoted by variable $n_2$, may be conjugated using two different amino bonds and a carbon linker attaching to a thyroid hormone antagonist comprising tetrac or a tetrac derivative. As shown in FIG. 10a, the thyrointegrin receptor antagonist may comprise two MAT molecules, wherein each MAT molecule may be conjugated to the outermost PEG molecule of the PEG polymer via the non-cleavable amino linkage. The composition 1010 may therefore be referred to as polyethylene glycol-bi-monoamine propyl tetrac (P-bi-MAT) 1010.

Similar to the composition 1010 of FIG. 10a, the composition of FIG. 10b may replacement each of the MAT's in the bifunctional P-bi-MAT with a non-cleavable diamino bond forming the conjugation forming the linkage between the PEG polymer and the thyroid hormone antagonist. Accordingly, the composition 1020 comprising diamino bonds may be summarily described as polyethylene glycol-bi-diamino propyl tetrac (P-bi-DAT) 1020. In one or more alternative embodiments, instead of using a MAT 210 or a DAT 220, the thyrointegrin antagonist being conjugated via the non-cleavable bond the PEG polymer may be a plurality of PGT 230 molecules. As shown in FIG. 7c, the PGT molecule and derivatives thereof may form a non-cleavable triazole bond between the polymer (PEG) and PGT, resulting in the formation of a P-TAT 730. Similar to the P-bi-MAT 1010 and P-bi-DAT 1020, P-TAT may form the bifunctional variation thereof shown in FIG. 10c comprising a triazole bond conjugating each thyroid hormone antagonist or derivative thereof to the PEG polymer. The bi-functional molecule may be referred to as polyethylene glycol-bi-triazole-tetrac (P-bi-TAT).

Figure 11:
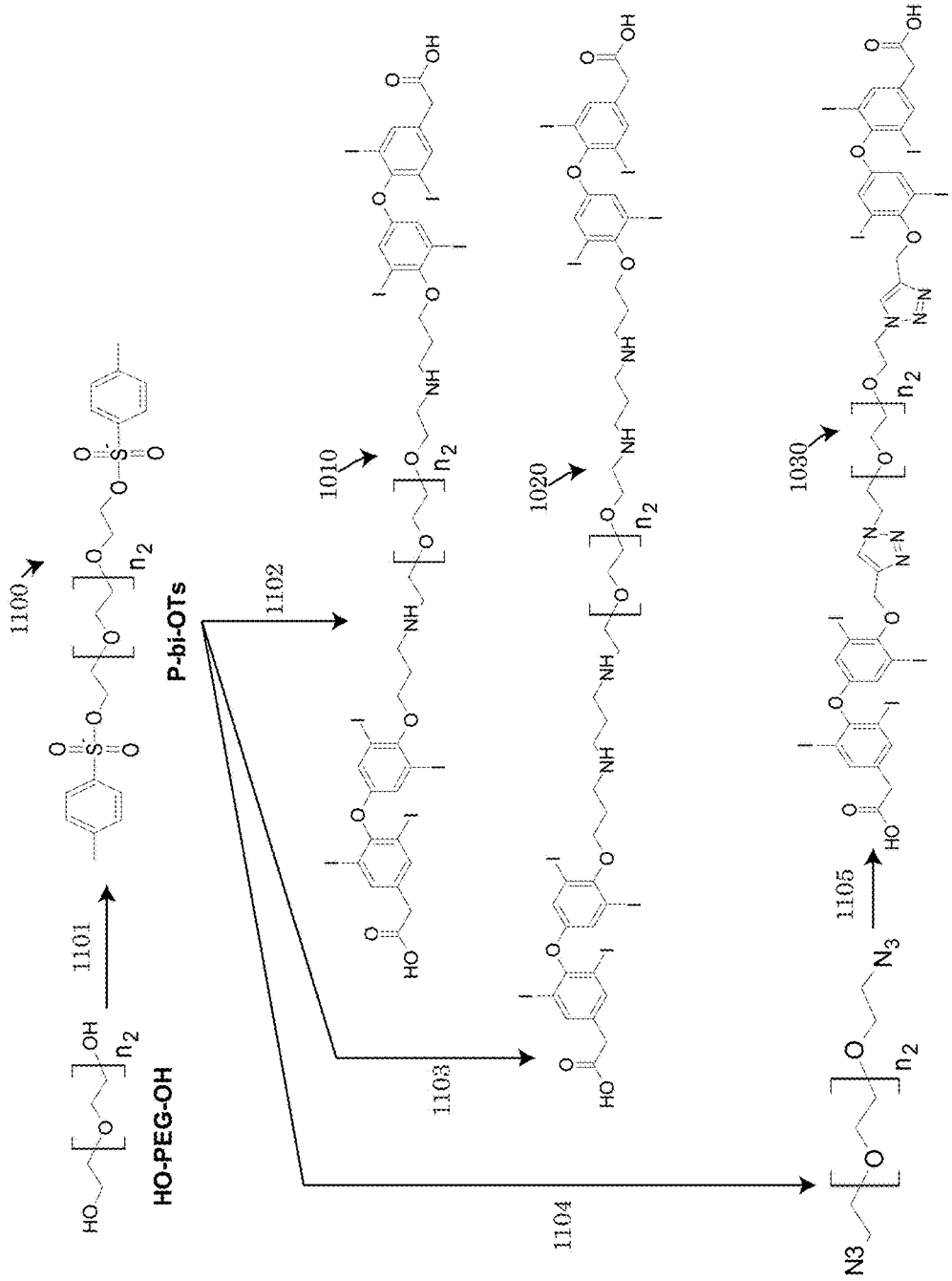
FIG. 11 depicts an embodiment of methods for synthesizing P-bi-MAT, P-bi-DAT and P-bi-TAT.

FIG. 11 describes one or methods for synthesizing the bi-functional thyrointegrin antagonists P-bi-MAT 1010, P-bi-DAT and P-bi-TAT using a PEG (depicted as OH-PEG-OH in embodiment 1100. In the first step of method 1100, the PEG may in step 1101 be tosylated to form bi-tosylated PEG. In one example described below, steps for toslylating the PEG may be performed as described in the following example:

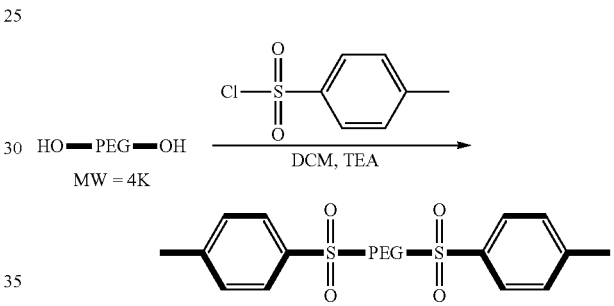

HO-PEG-OH (1.5 g, 0.25 mmol, eq=1) dissolved in 50 ml DCM and stirred in for 15 minutes. 4-toluenesulfonyl chloride (0.38 g, 2.02 mmol, eq=8) and 1 ml TEA was added to mixture. Reaction stirred in room temperature for overnight. Reaction diluted in DCM and washed by HCl 1N, (2×), brine 1×. Mixture concentered and DCM removed completely and result re-crystallized by ethyl acetate overnight. White powder collected after filtration and residue 1.4 g obtained.

The second step of the method 1100 may vary depending on the desired final product looking to be achieved. If the desired final thyrointegrin antagonist is P-bi-MAT 1010, the bi-tosylated PEG may be introduced via step 1102 to the presence of MAT 210 resulting in the replacement of the tosyl groups in the bi-tosylated PEG with a MAT 210 covalently bound via amino bonds to each side of the PEG polymer creating P-bi-MAT. Similarly, the tosyl groups of the bi-tosyl-PEG may be replaced with DAT 220 groups in step 1103. As the bi-tosyl PEG is introduced in the presence of the DAT, the DAT may bind to the PEG via one or more covalent diamino bonds resulting in the formation of P-bi-DAT 1020.

If, however, the desired goal is to obtain a P-bi-TAT 1030, one or more additional steps may be performed. Firstly, in step 1104, a bi-Azido-PEG may be formed from the bi-tosylated-PEG of step 1101. One example of an embodiment of the steps for synthesizing bi-Azido-PEG may be described as follows:

Synthesis of bi-Azido-PEG (MW=4000)

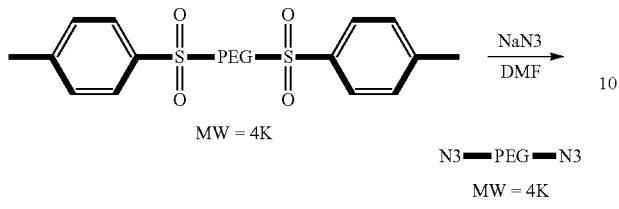

sTO-PEG-OTs (2500 mg, ~0.5 mmol, eq.=1) dissolved in 20 ml DMF and then 3000 mg NaN₃ is added to solution and the reaction is set to 80° C. for overnight. 200 ml water is added to the solution and extracted by DCM three times. The organic phases combined and washed by brine and dried over MgSO₄. The solvent is removed and recrystallized by ethyl acetate at −20 C and filtered, producing 1750 mg of bi-azido modified PEG obtained.

Once the bi-Azido modified PEG is obtained in step 1104, the bi-Azido-PEG may be reacted in step 1105 the presence TAT 730 in order to form P-bi-TAT 1030 as shown in FIG. 11. The following example demonstrates in further detail the synthesis of the reaction from bi-Azido-PEG to P-bi-TAT 1030;

Synthesis of P-bi-TAT (MW=4000)

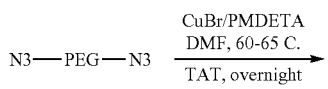

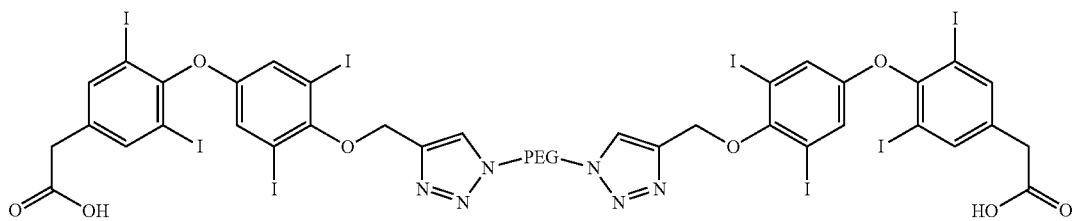

Bi-Azido-PEG (N3-PEG-N3) (2000 mg, 0.5 mmol, eq=1) dissolved in 8 ml DMF and then 1570 mg of TAT (2 mmol, eq=4) added to reaction. 286 mg CuBr (2 mmol, eq=4), and 814 μl of N,N,N',N'',N''-Pentamethyldiethylenetriamine (PMDETA) (4 mmol, eq=8) dissolved in 2 ml DMF and added to solution and set the reaction in 60-65 C for overnight. Reaction cooled down to room temperature and diluted the reaction in 100 ml DCM. Cooper removed by passing through aluminum oxide column which negatively activated by carboxylic acid and wash several times by DCM and then concentrated mixture to 100 ml. Washed the mixture by 200 ml water (3×) and brine (2×). 5) The organic phase dried over MgSO4, removed the DCM and finally re-crystallized the final product by adding 200 ml of ethyl acetate. Repeated the recrystallization two more times and yellowish powder obtained by filtration.

The phenolic hydroxyl group (—OH) of the thyroid analogs is an important site for their modification and as a target site for converting tetrac to an integrin antagonist without any changes to the carboxylic acid moiety of tetrac. The molecular structure tetraiodothyroacetic acid (tetrac) is synthetically modified with propargyl bromide to prepare an alkyne modified tetrac, Propargyl Tetrac (PGT), {4-[3, 5-di-iodo-4-(prop-2-yn-1-yloxy) phenoxy]-3, 5-diiodophenyl} acetic acid; molecular weight, 785 Daltons). PGT conjugated to O, O'-Bis (azide) polyethylene glycol (molecular weight, 4,050 Daltons) via click chemistry to yield p-bi-TAT with a molecular weight of 5,620 Daltons, as shown in FIG. 11 and in the scheme for P-bi-TAT synthesis demonstrated below:

P-bi-TAT Synthesis:

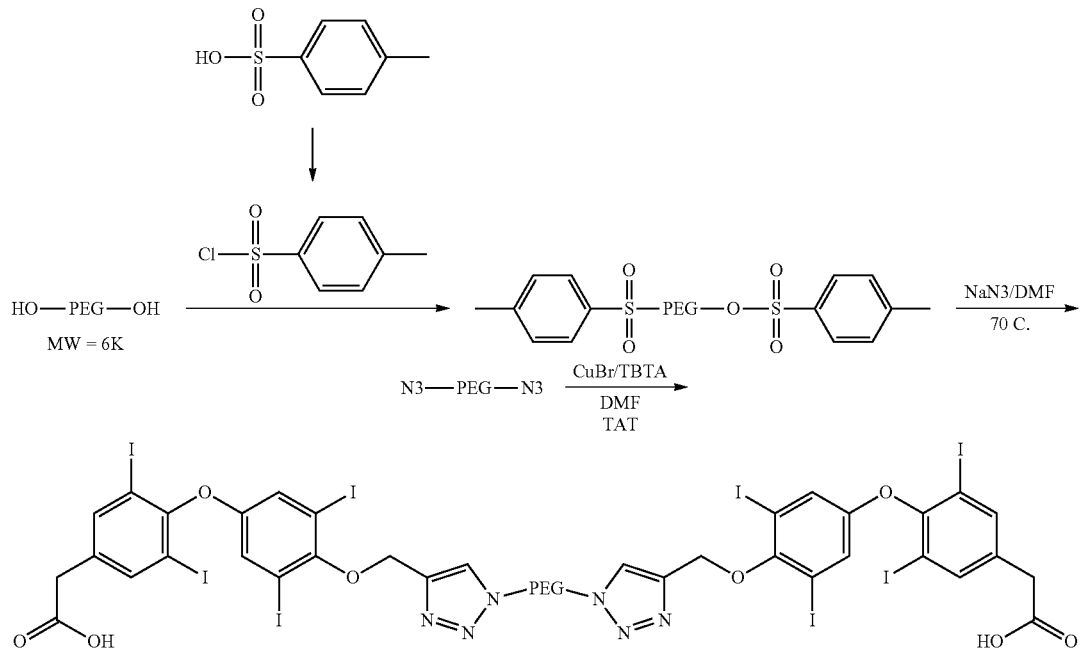

Chemical Name: O,O'-Bis({4-[3,5-diiodo-4-(1-methylen-1,2,3-triazol-4-ylmethoxy)phenoxy]-3,5-diiodophenyl} acetic acid) polyethylene glycol.

Physical Appearance: Yellowish brown powder Solubility: Soluble in water at 50 mg/ml; in Phosphate buffer, pH 8.0 at 100 mg/ml; in 10% Ethanol at 150 mg/ml, and in 50% propylene glycol at 200-300 mg/ml.

Figure 12:
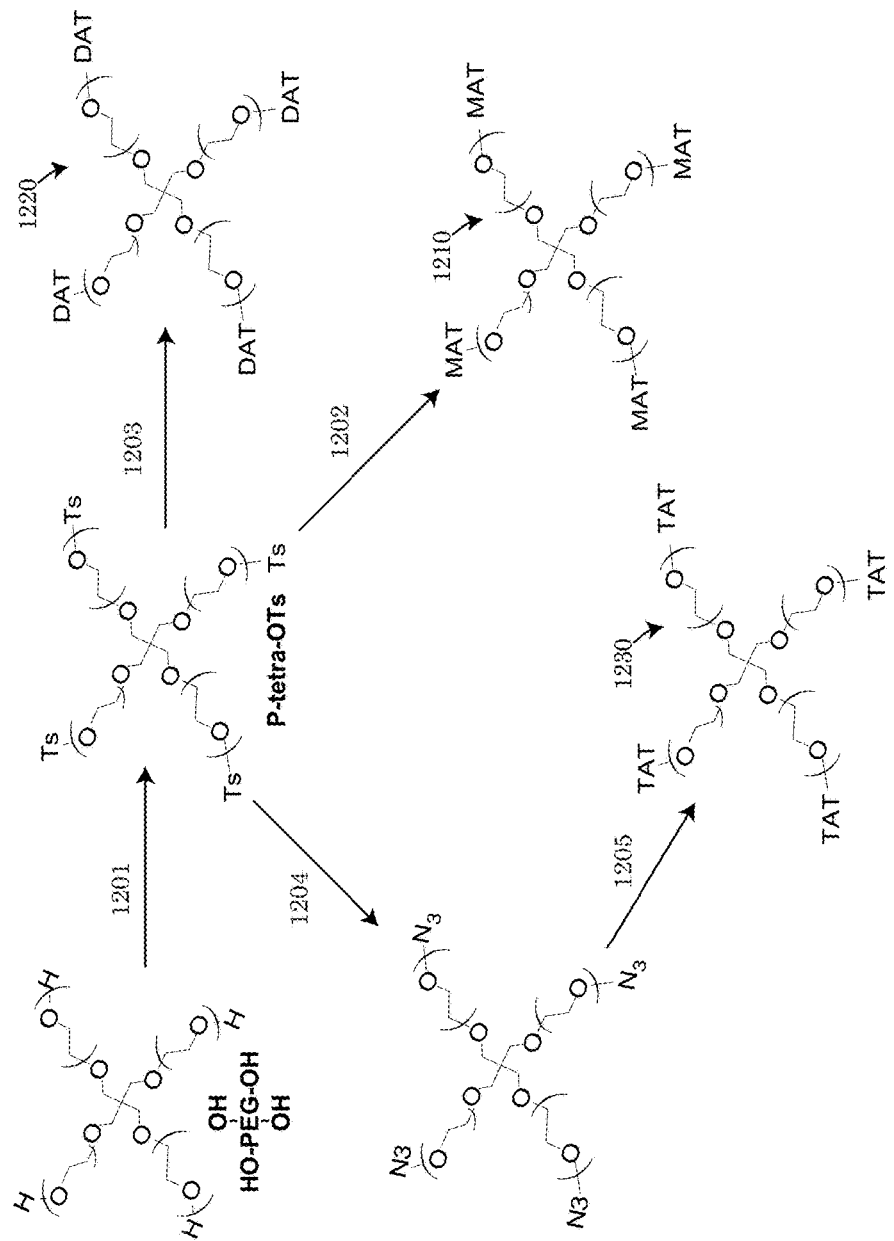
FIG. 12 depicts an embodiment of methods for synthesizing tetra functional derivatives of thyrointegrin antagonists, polyethylene glycol tetra-monoamino propyl tetrac (P-tetra-MAT (P-tetra-MAT), polyethylene glycol tetra-diamino propyl tetrac (P-tetra-DAT) and polyethylene glycol tetra-triazole tetrac (P-tetra-TAT) using tetra polyethylene glycol.

In some embodiments of the polymer conjugated thyrointegrin antagonists, the compositions may not only be mono-functional as shown by the general formula 600 or bi-functional as shown by the composition having the general formula 900, but may further be tetra-functional as demonstrated by the examples of FIG. 12. For example, similar to the methods for preparing P-bi-MAT 1010, P-bi-DAT 1020 and P-bi-TAT as shown in FIG. 11 and described above, tetra functional derivatives of P-tetra-MAT 1210, P-tetra-DAT and P-tetra-TAT may be synthesized. The synthetization steps for preparing the tetra functional thyrointegrin antagonists shown in FIG. 12 may be analogous to the steps for preparing mono-conjugated and bi-conjugated derivatives shown in the example methods of FIGS. 8 and 11.

For example, instead of using m-PEG or PEG as the starting material, a tetra-PEG may be used. In step 1201, the tetra-PEG may be tosylated into P-tetra-OTS and subsequently reacted in the presence of P-MAT 710 or P-DAT 720 to form P-tetra-MAT 1210 and P-tetra-DAT 1220 respectively. Likewise, similar to synthesis of P-TAT 730 and p-bi-TAT 1030, p-tetra-TAT 1230 may be synthesized by first converting toslylated P-tetra-OTS into P-tetra-azido as shown in step 1204. Subsequently, in step 1205, the p-tetra-azido composition may be reacted in the presence of p-TAT 730 to create the p-tetra-TAT 1230.

Figure 13A:
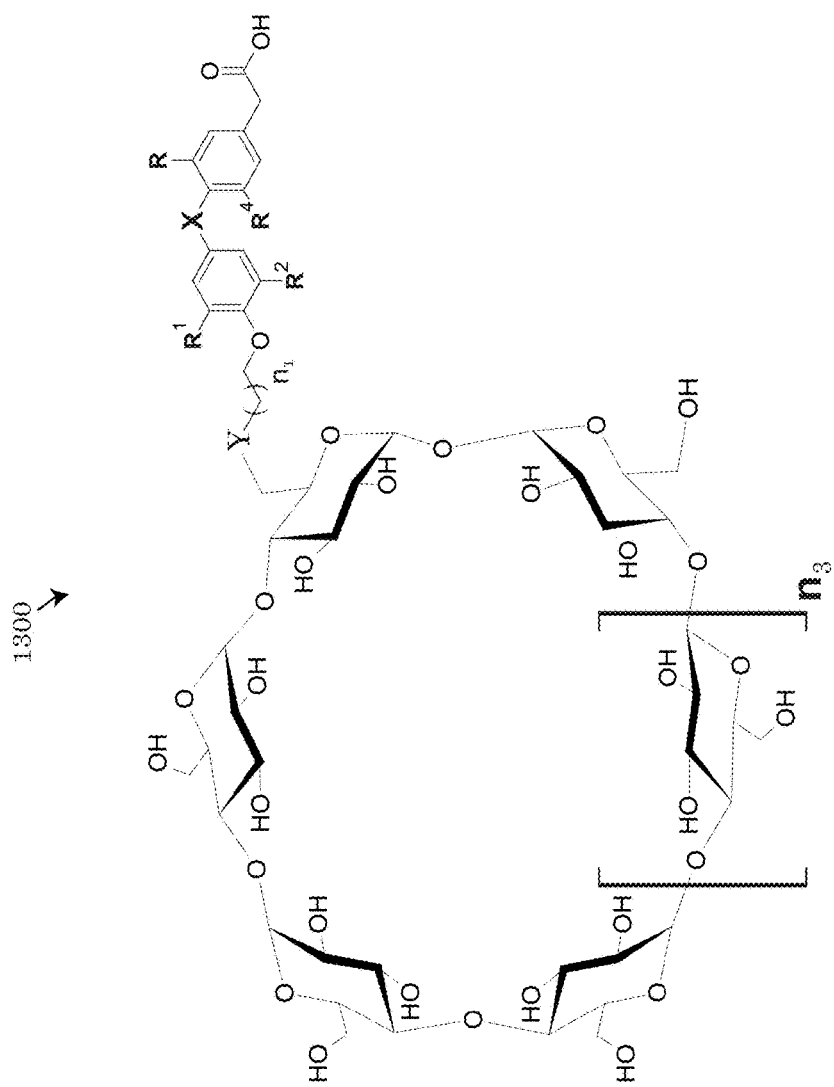
FIG. 13a depicts an embodiment of a general formula of a thyrointegrin antagonist derivative conjugated to a cyclodextrin.
Figure 13B:
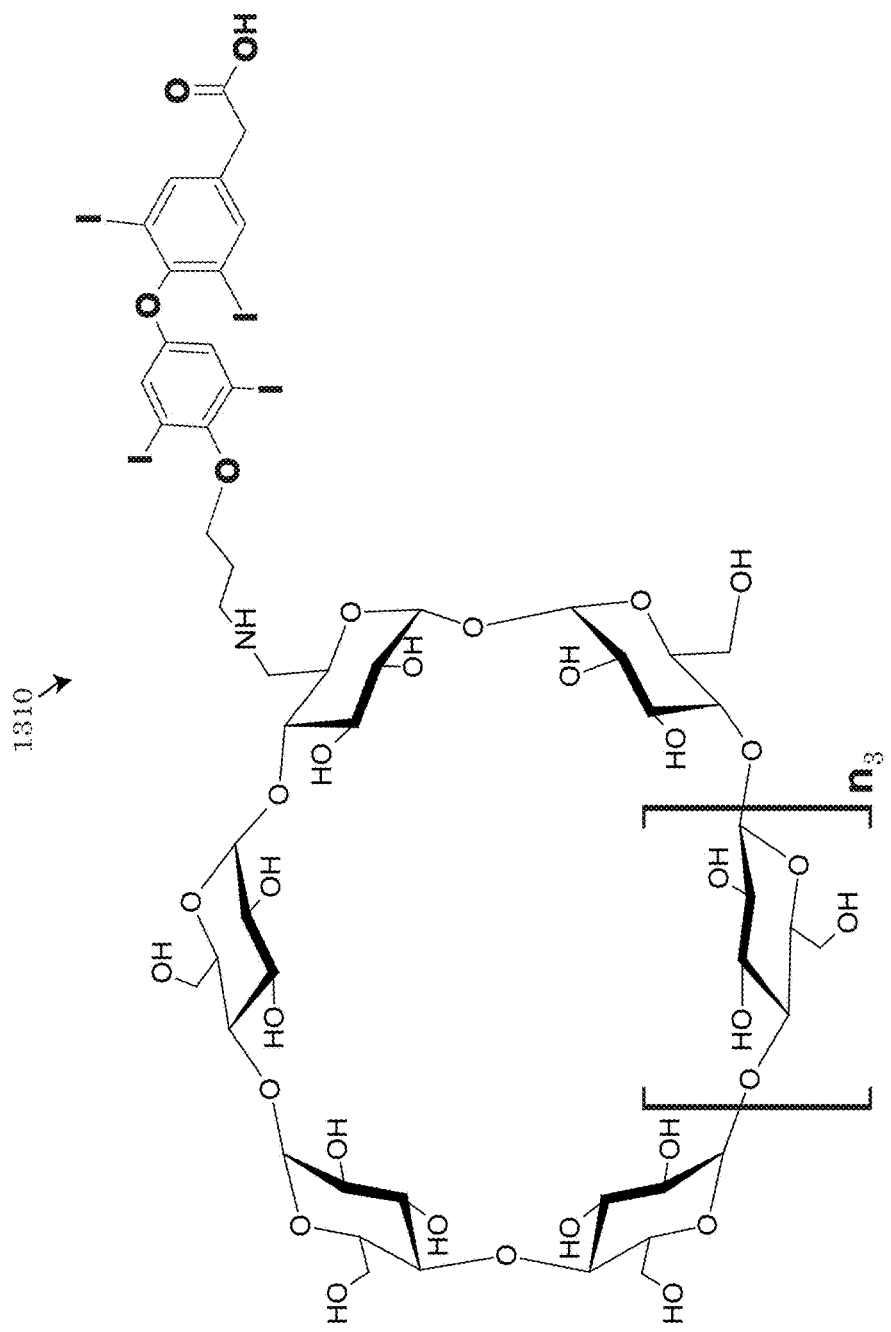
FIG. 13b depicts an embodiment of a chemical structure for cyclodextrin monoamino propyl tetrac (C-MAT).
Figure 13C:
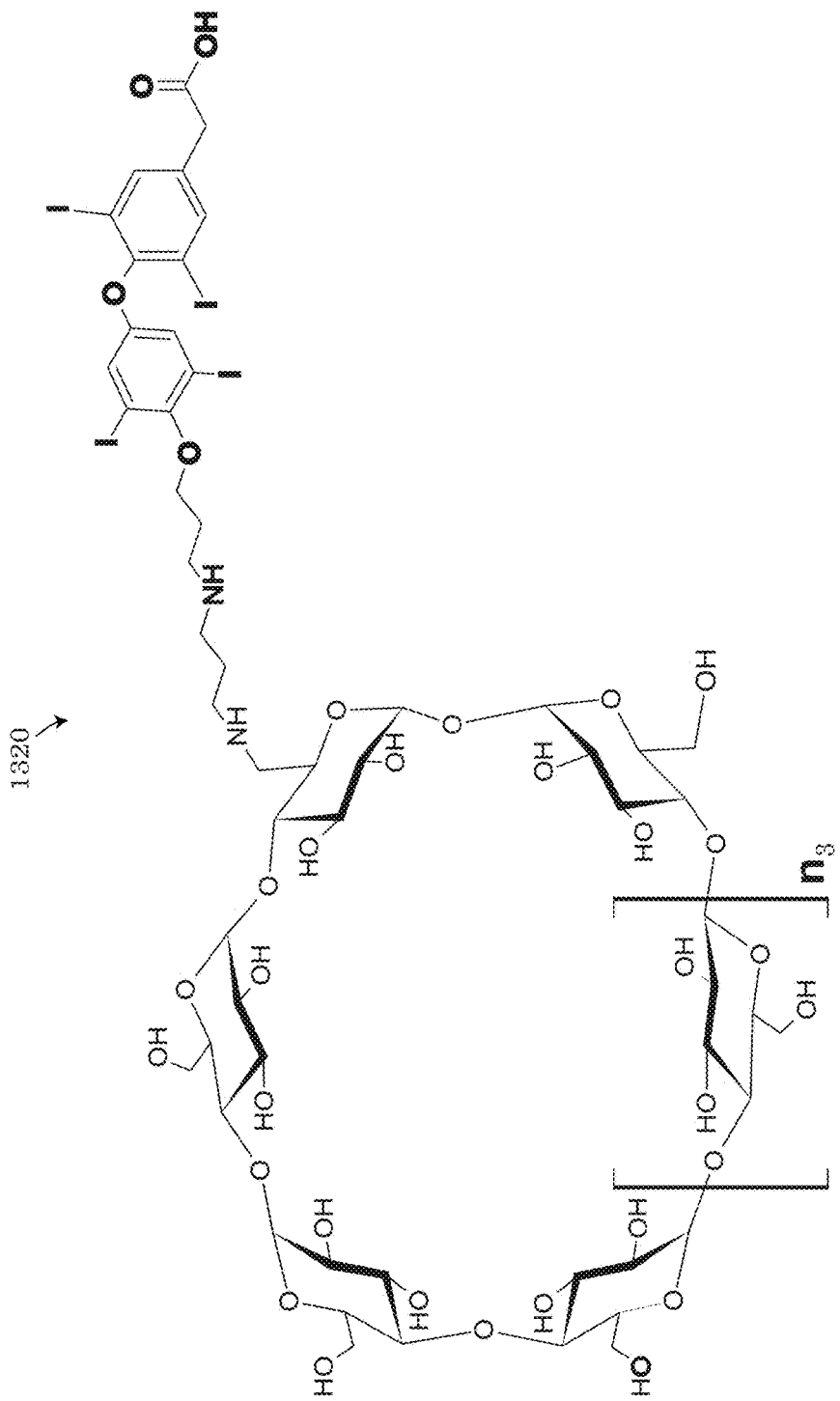
FIG. 13c depicts an embodiment of a chemical structure for cyclodextrin diamino propyl tetrac (C-DAT).
Figure 13D:
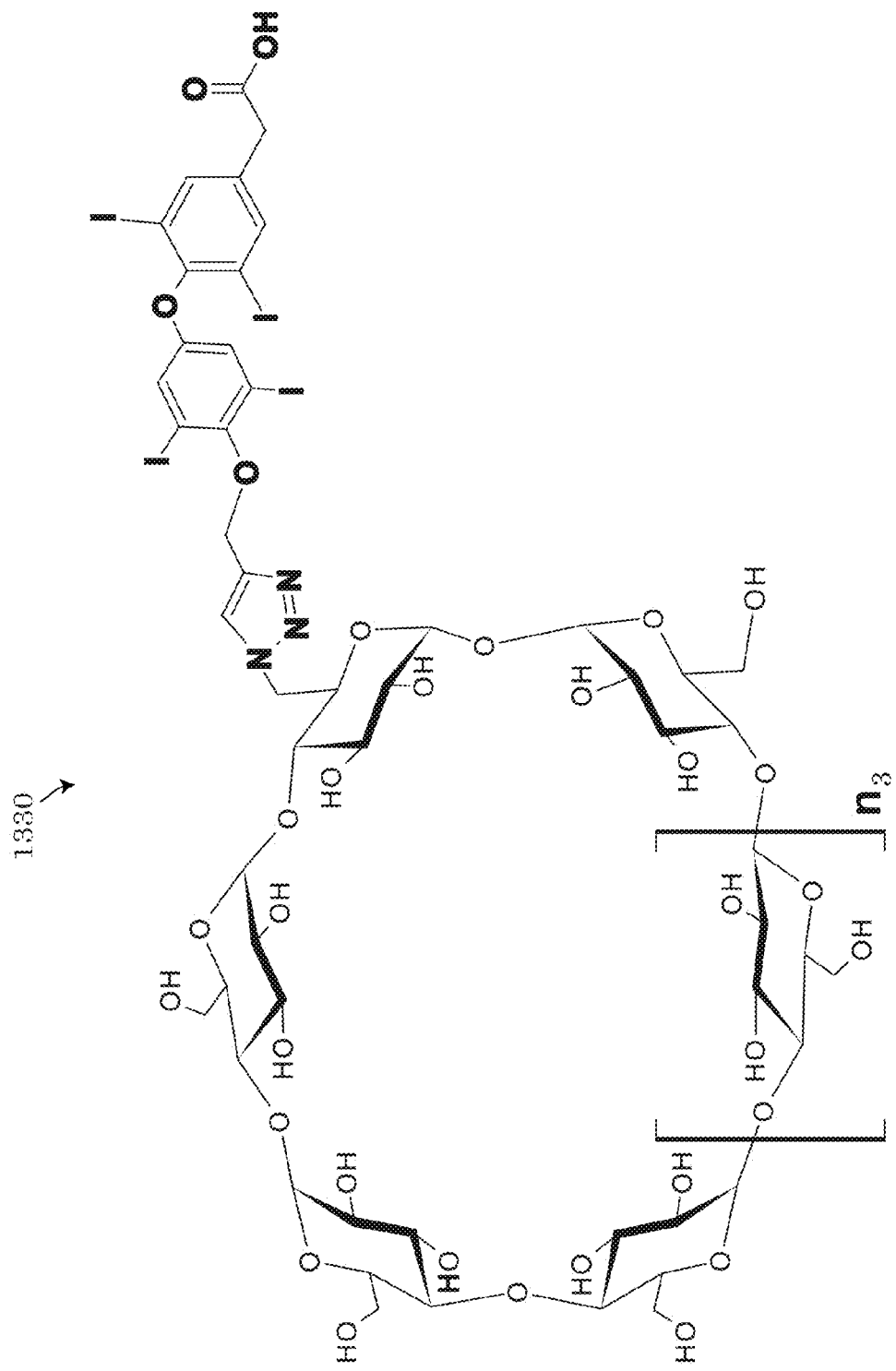
FIG. 13d depicts an embodiment of chemical structure for cyclodextrin triazole tetrac (C-TAT).

In alternative embodiments of the thyrointegrin antagonists, the polymer, Z of the general formula 500, may be substituted for an α, β, or γcyclodextrin, as shown by the general formula 1300 of FIG. 13a. In the formula 1300, the variable $n_3$=1, 2 or 3 repeated monomeric subunits of the cyclodextrin, wherein the number of repeated subunits may identify the cyclodextrin used as the polymer in the conjugated thyrointegrin antagonist. For example, when $n_3$=1, the cyclodextrin is α-cyclodextrin, $n_3$=2 the cyclodextrin is β-cyclodextrin and when or $n_3$=3, the cyclodextrin may be γ-cyclodextrin. Similar to the other thyrointegrin antagonist derivatives described by the general formula 100 and 500 above, the substitutions for $R^1$, $R^2$, $R^3$, $R^4$, X, Y and $n_1$ may occur in a similar manner in formula 1300. FIGS. 13b-13d provide examples of cyclodextrin conjugated thyrointegrin antagonists. Specifically, in FIG. 13b, a cyclodextrin-mono-amino-propyl tetrac (C-MAT) 1310 is provided, whereas in FIG. 13c a cyclodextrin-diamino-propyl tetrac (C-DAT) 1320 is exemplified. Moreover, FIG. 13d depicts an example of the chemical structure of cyclodextrin-triazole tetrac (C-TAT) 1330.

Figure 14A:
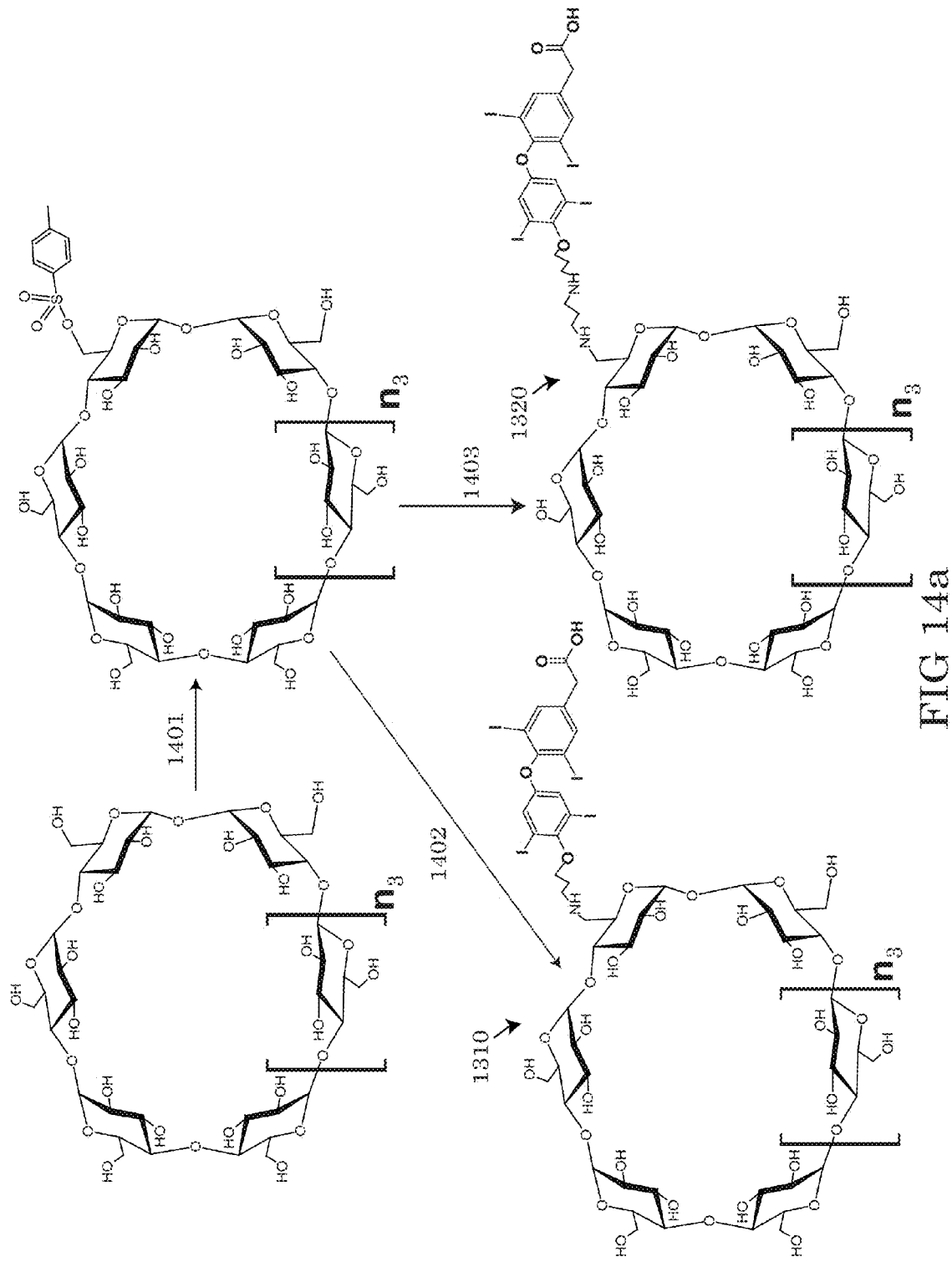
FIG. 14a depicts an embodiment of a method for synthesizing C-MAT and C-DAT using an alpha (α), beta (β) or gamma (γ) cyclodextrin.
Figure 14B:
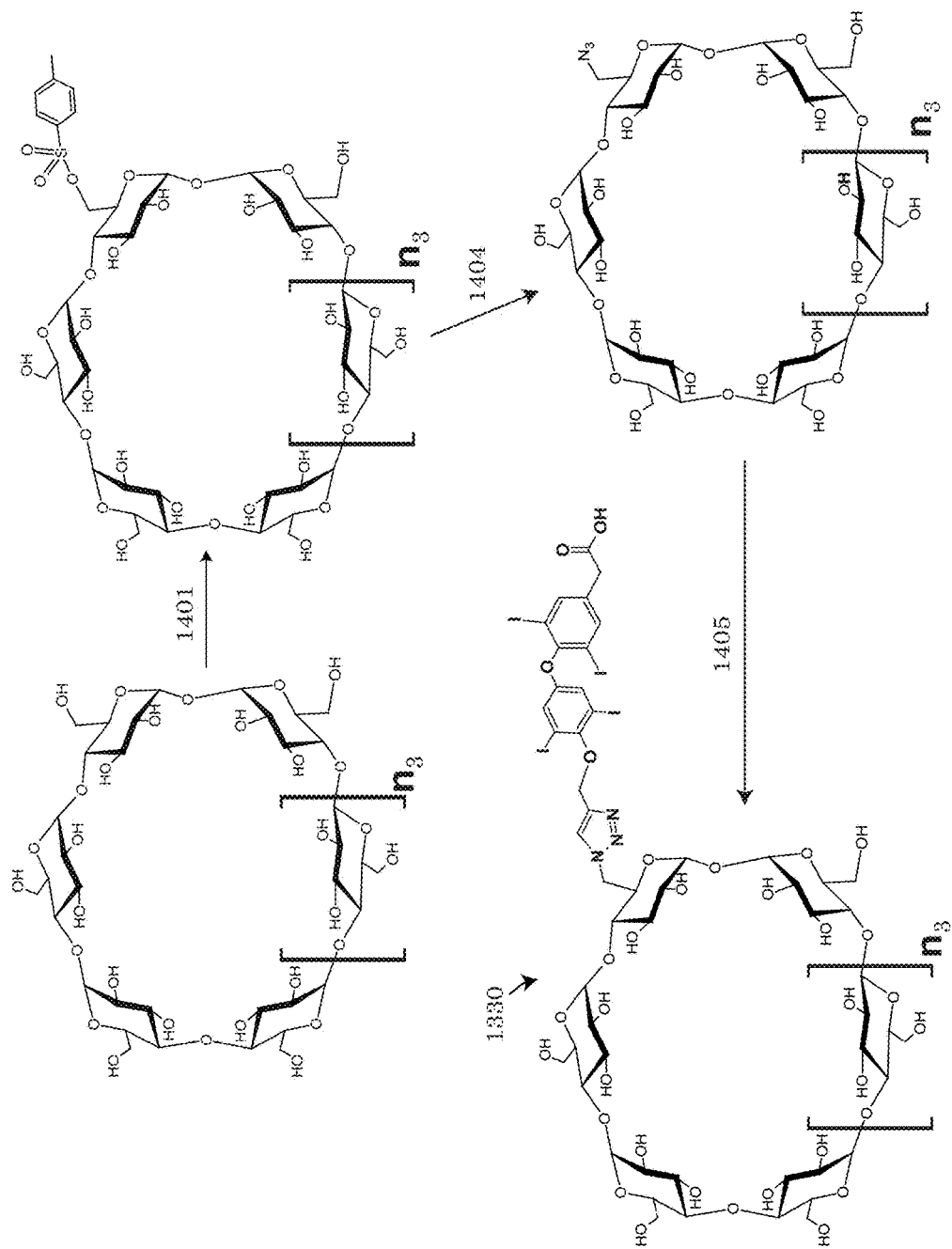
FIG. 14b depicts an embodiment of a method for synthesizing C-TAT using an alpha (α), beta (β) or gamma (γ) cyclodextrin.

The methods of synthesizing the C-MAT 1310, C-DAT 1320 and C-TAT 1330 follow similar synthetization steps as alternatively conjugated variations of the P-MAT 710, P-DAT 720 and P-TAT 730 described previously. As shown in FIG. 14a and FIG. 14b, synthesizing may begin at step 1401 by tosylating the cyclodextrin polymer to a tosylated-cyclodextrin. In order to create C-MAT 1310 or C-DAT 1320, the MAT 210 or DAT 220 may be reacted in the presence of the tosylated-cyclodextrin in steps 1402 or 1403 respectively. In order to synthesize C-TAT 1330, the tosylated-cyclodextrin resulting from step 1401 may be further reacted in step 1404 to create cyclodextrin-azido composition, which may be further reacted in the presence of PGT 230 in step 1405, resulting in the synthetization of C-TAT 1330.

Figure 45:
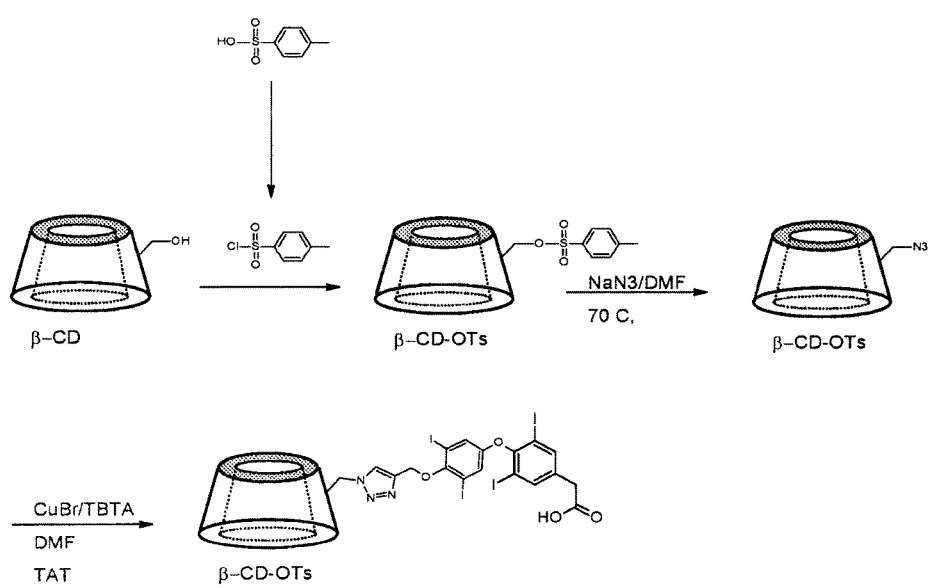
FIG. 45 depicts an embodiment of a method for synthesizing a cyclodextrin conjugated thyrointegrin antagonist C-TAT.

The following examples describe the synthetization of cyclodextrin conjugated thyrointegrin antagonists in more detail with reference to the method of synthesizing depicted in FIG. 45:

Synthesis of C-TAT—Synopsis on the Synthesis:

The phenolic hydroxyl group (—OH) of thyroid analogs is an important site for their modification and as a target site for converting tetrac to an integrin antagonist without any changes to the carboxylic acid moiety of tetrac. The molecular structure tetraiodothyroacetic acid (tetrac) is synthetically modified with propargyl bromide to prepare an alkyne modified tetrac, Propargyl Tetrac (PGT), {4-[3, 5-diiodo-4-(prop-2-yn-1-yloxy) phenoxy]-3, 5-diiodophenyl} acetic acid; molecular weight, 785 Daltons). PGT conjugated to mono-6-azide-deoxy-6-β-cyclodextrin via click chemistry to yield β-C-TAT.

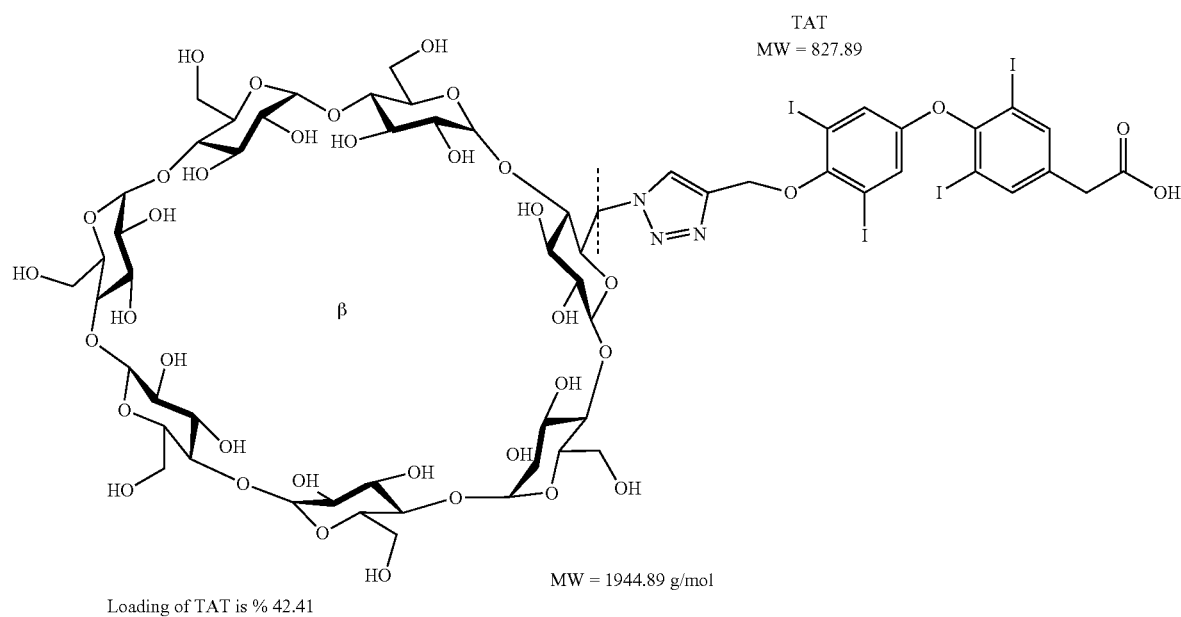

Loading of TAT is % 42.41

Beta C-TAT: Mol. Wt.: 1,944.89 Daltons

Chemical Name: 6-({4-[3,5-diiodo-4-(1-methylen-1,2,3-triazol-4-ylmethoxy)phenoxy]-3,5-diiodophenyl}acetic acid)-6-deoxy-β-cyclodextrin Synthesis of γ-C-TAT—Synopsis on the Synthesis:

The phenolic hydroxyl group (—OH) of thyroid analogs is an important site for their modification and as a target site for converting tetrac to an integrin antagonist without any changes to the carboxylic acid moiety of tetrac. The molecular structure tetraiodothyroacetic acid (tetrac) is synthetically modified with propargyl bromide to prepare an alkyne modified tetrac, Propargyl Tetrac (PGT), {4-[3, 5-diiodo-4-(prop-2-yn-1-yloxy) phenoxy]-3, 5-diiodophenyl} acetic acid; molecular weight, 785 Daltons). PGT conjugated to mono-6-azide-deoxy-6-γ-cyclodextrin via click chemistry to yield γ-C-TAT with a molecular weight of 2,108 Daltons. Detailed Schematic for the synthesis of C-TAT is as shown below.

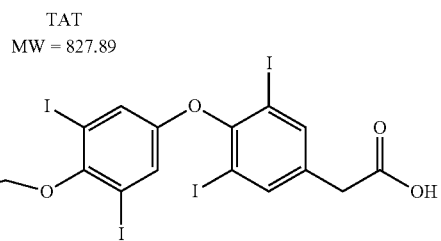
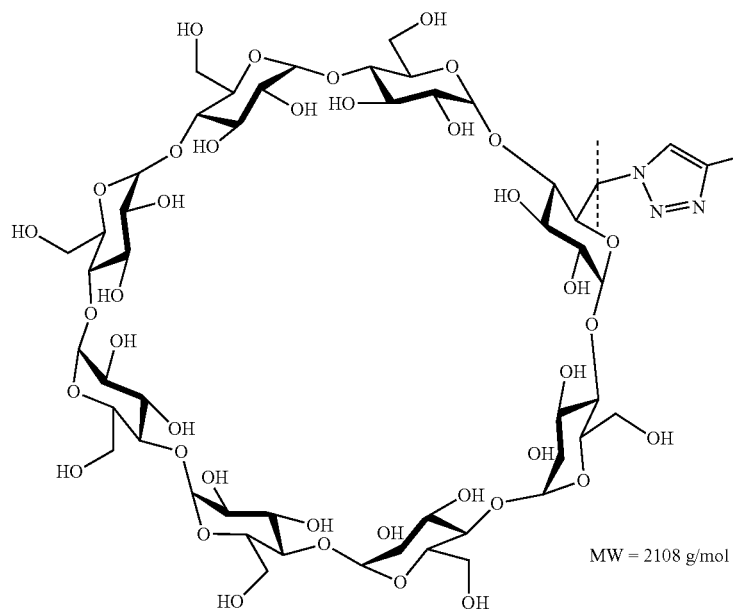

Loading of TAT is % 39.27

Figure 15A:
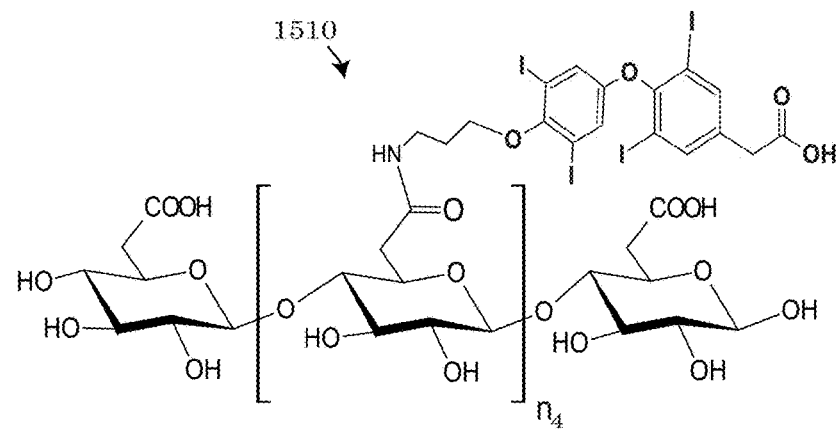
FIG. 15a depicts an embodiment of a thyrointegrin antagonist derivative conjugated to an alginic acid polymer forming alginic acid monoamino propyl tetrac (A-MAT).
Figure 15B:
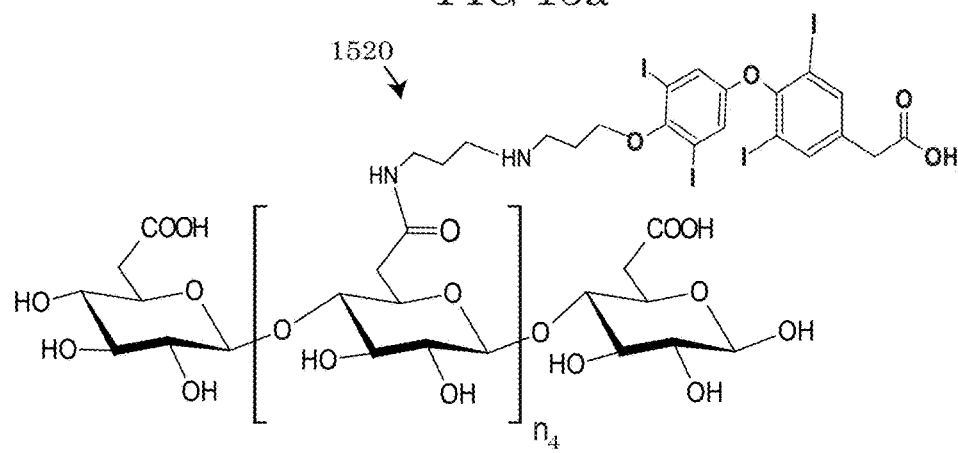
FIG. 15b depicts an embodiment of a thyrointegrin antagonist derivative conjugated to an alginic acid polymer forming alginic acid diamino propyl tetrac (A-DAT).
Figure 15C:
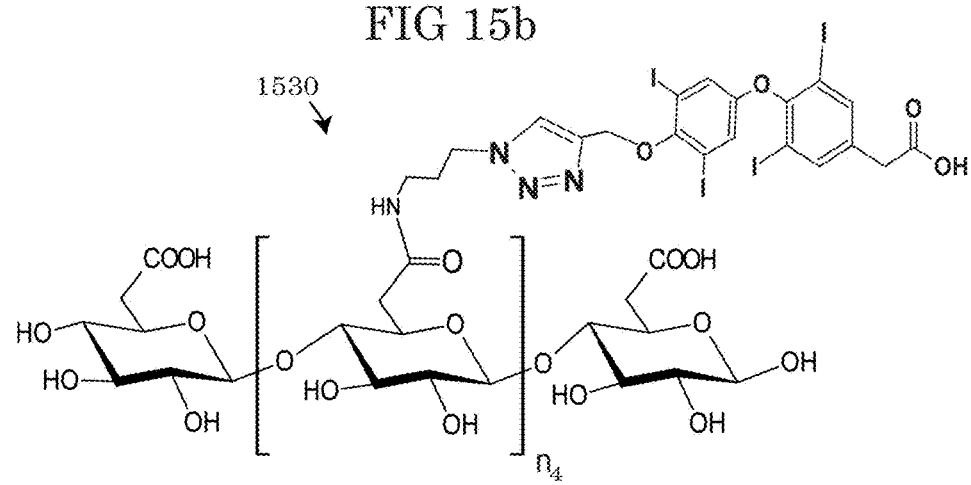
FIG. 15c depicts an embodiment of a thyrointegrin antagonist derivative conjugated to an alginic acid polymer forming alginic acid triazole tetrac (A-TAT).

Structure of C-TAT
Chemical Name: 6-({4-[3,5-diiodo-4-(1-methylen-1,2,3-triazol-4-ylmethoxy)phenoxy]-3,5-diiodophenyl}acetic acid)-6-deoxy-γ-cyclodextrin.
Mol. Wt.: 2,108 Daltons In some alternative embodiments of the polymer conjugated thyrointegrin antagonists having the general formula 500, the polymer described by the variable Z may be substituted with an alginic acid polymer as shown by the examples depicted in FIG. 15a-15c. For instance, in FIG. 15a, alginic acid polymer may be conjugated to a P-MAT 710 resulting in the formation of alginic acid-monoamino-propyl tetrac (A-MAT) 1510 or a derivative thereof, wherein the variable $n_4$ defines a number of repeating monomer subunits of the alginic acid. The variable $n_4$ may be any number of repeating subunits≥1. In FIG. 15b, an alternative conjugation using a DAT 720 to the alginic acid polymer may be used or a derivative thereof. The resulting conjugation of the alginic acid polymer with a DAT 720 may be referred to as Alginic acid-diamino-propyl tetrac (A-DAT) 1520, whereas the conjugation between TAT 730 and alginic acid results in the formations of alginic acid-triazole tetrac (A-TAT) 1530 or a derivative thereof.

Figure 16A:
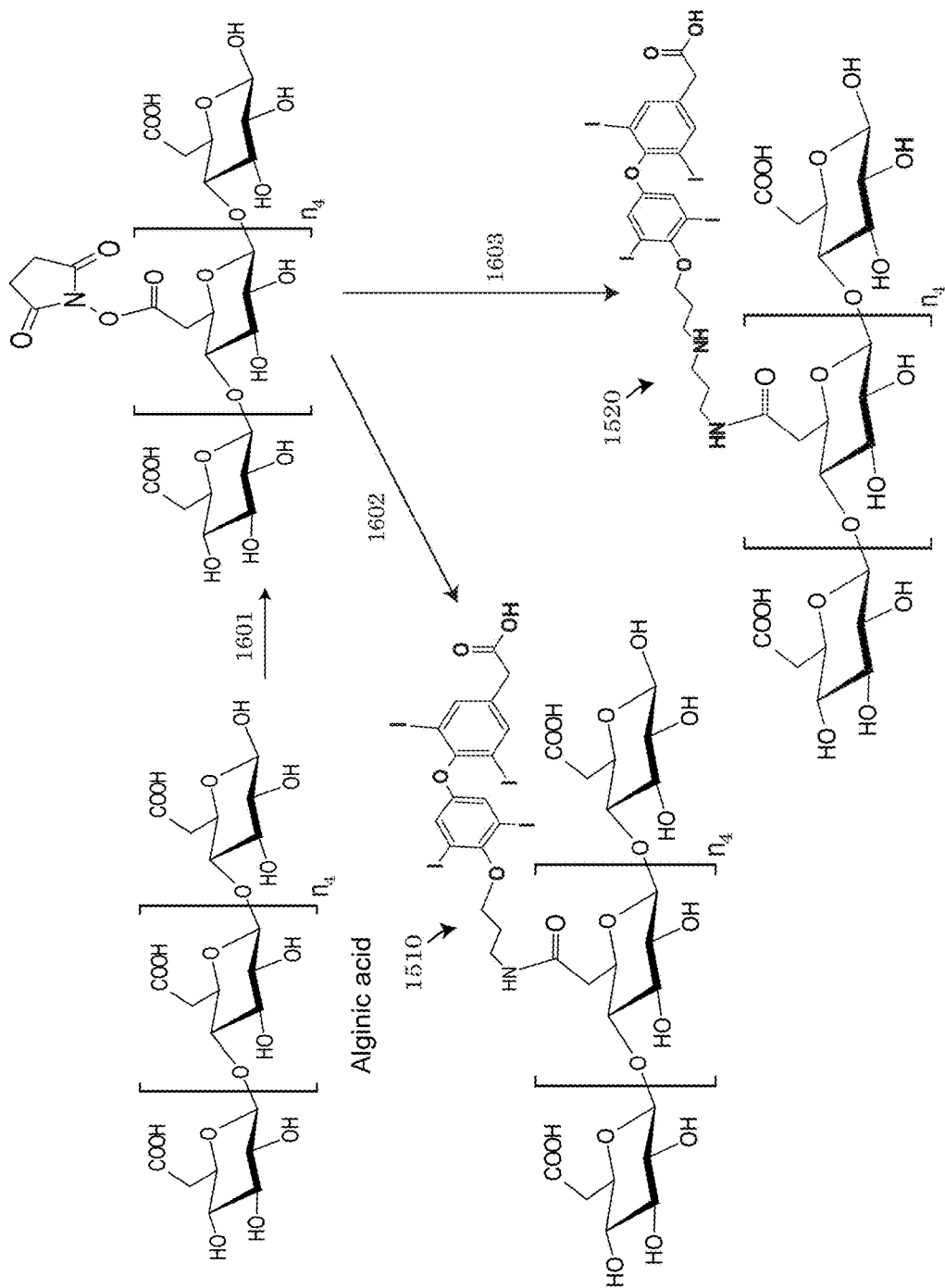
FIG. 16a depicts an embodiment of a method for synthesizing A-MAT and A-DAT from alginic acid.

The synthetization of A-MAT 1510, A-DAT 1520 and A-TAT 1530 follows a slightly altered set of steps compared with the synthetization of the previous polymer conjugations of PEG and cyclodextrin above. As shown in FIG. 16a, synthesizing method starts with the alginic acid polymer. Instead of tosylating the polymer, step 1601 reacts the alginic acid with N-hydroxy-succinimide, attaching the N-hydroxy-succinimide (NHS) to the carboxyl group of the alginic acid. In steps 1602 and 1603, the NHS may be removed in a substitution reaction by introducing MAT 210 (step 1602) or DAT 220 (step 1603) to replace the NHS of the alginic acid with either MAT 210, forming A-MAT 1510 or DAT 220 forming A-DAT 1520.

Figure 16B:
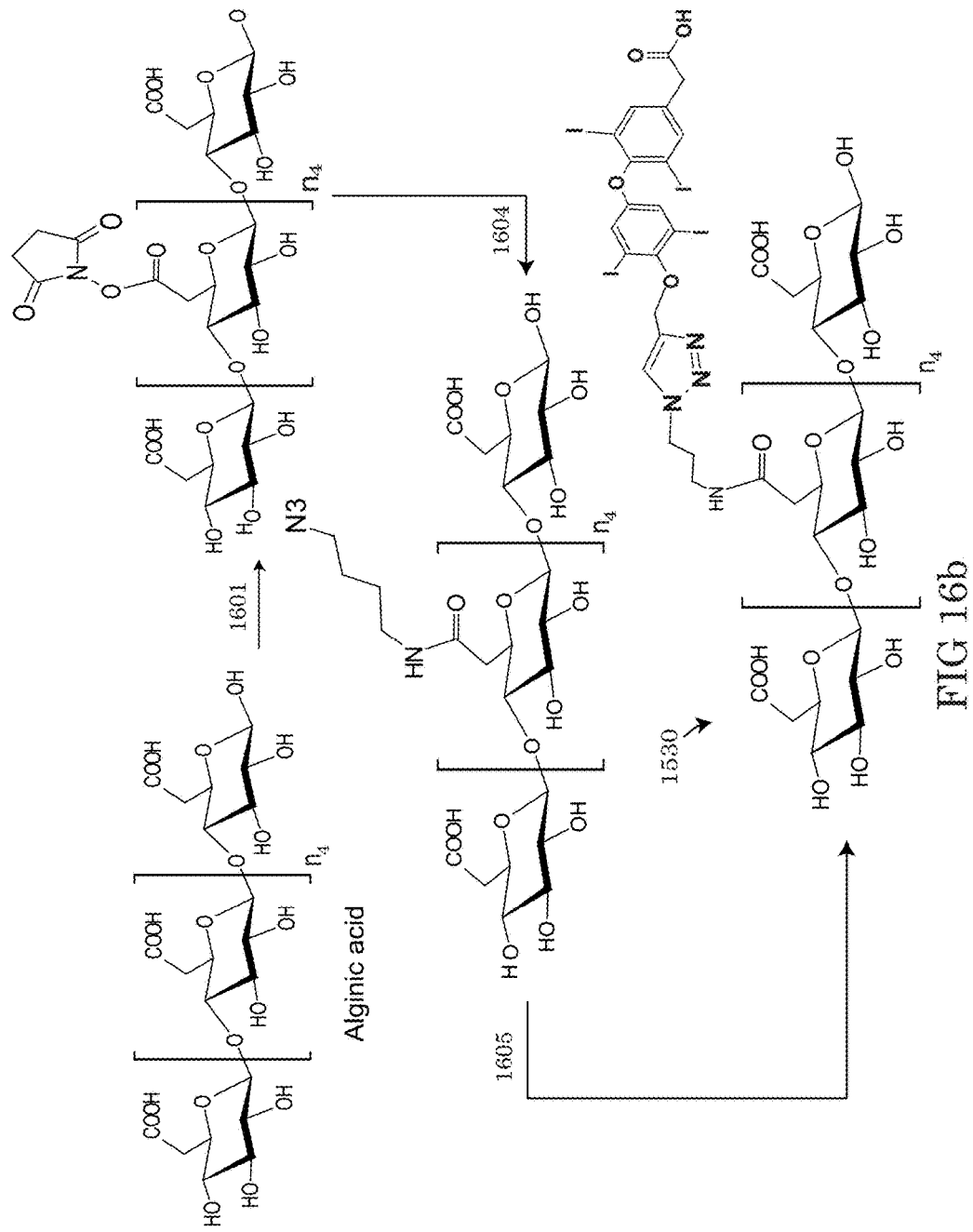
FIG. 16b depicts an embodiment of a method for synthesizing A-TAT from Alginic acid.

FIG. 16b depicts the method steps for preparing A-TAT 1530 from an alginic acid starting material. The alginic acid is reacted with the NHS to form NHS-alginic acid in step 1601. In step 1604, the NHS-alginic acid undergoes a reaction with an azido compound, replacing the NHS attached to the carboxyl group of the alginic acid with the azido compound resulting in a alginic acid-azido compound as shown in FIG. 16b. Lastly, the alginic acid-azido compound formed because of step 1604 may be further reacted in step 1605 in the presence of PGT 230 to form a triazole bond with the N3 of the azido group, generating A-TAT 1530.

Figure 17A:
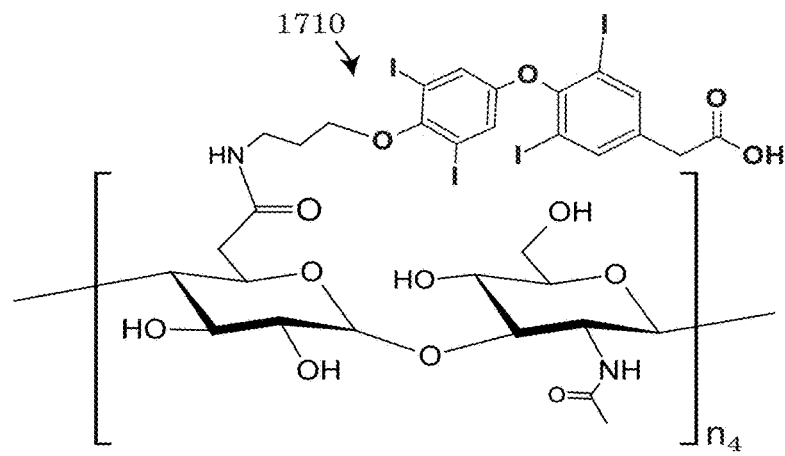
FIG. 17a depicts an embodiment of a thyrointegrin antagonist derivatives conjugated to a hyaluronic acid polymer with a non-cleavable monoamino bond forming hyaluronic acid-monoamino propyl tetrac (H-MAT).
Figure 17B:
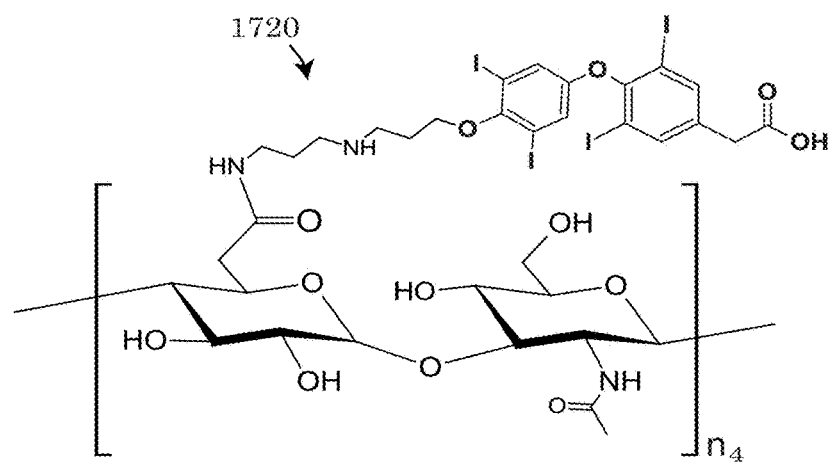
FIG. 17b depicts an embodiment of a thyrointegrin antagonist derivatives conjugated to a hyaluronic acid polymer with a non-cleavable diamino bond forming hyaluronic acid-diamino propyl tetrac (H-DAT).
Figure 17C:
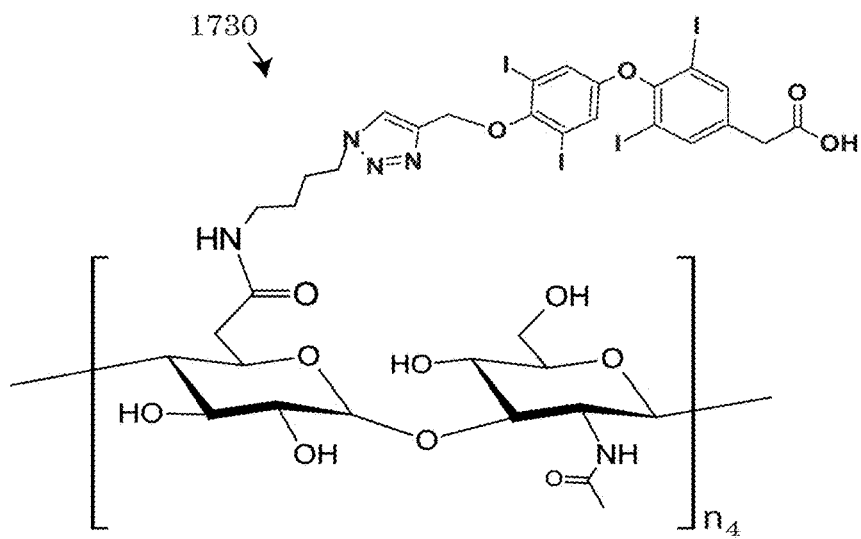
FIG. 17c depicts an embodiment of a thyrointegrin antagonist derivatives conjugated to a hyaluronic acid polymer with a non-cleavable triazole bond forming hyaluronic acid-triazole propyl tetrac (H-TAT).

In some alternative embodiments of the polymer conjugated thyrointegrin antagonists having the general formula 500, the polymer described by the variable Z may be substituted with a hyaluronic acid polymer as shown by the examples depicted in FIG. 17a-17c. For instance, in FIG. 17a, the hyaluronic acid polymer may be conjugated to a P-MAT 710 resulting in the formation of hyaluronic acid-monoamino-propyl tetrac (H-MAT) 1710 or a derivative thereof, wherein the variable $n_4$ defines a number of repeating monomer subunits of the hyaluronic acid. The variable $n_4$ may be any number of repeating subunits≥1. In FIG. 17b, an alternative conjugation using a DAT 720 and the hyaluronic acid polymer may be used or a derivative thereof. The resulting conjugation of the hyaluronic acid polymer with a DAT 720 may be referred to as hyaluronic acid-diamino-propyl tetrac (H-DAT) 1720, whereas the conjugation between TAT 730 and hyaluronic acid results in the formations of hyaluronic acid-triazole tetrac (H-TAT) 1730 or a derivative thereof.

Figure 18A:
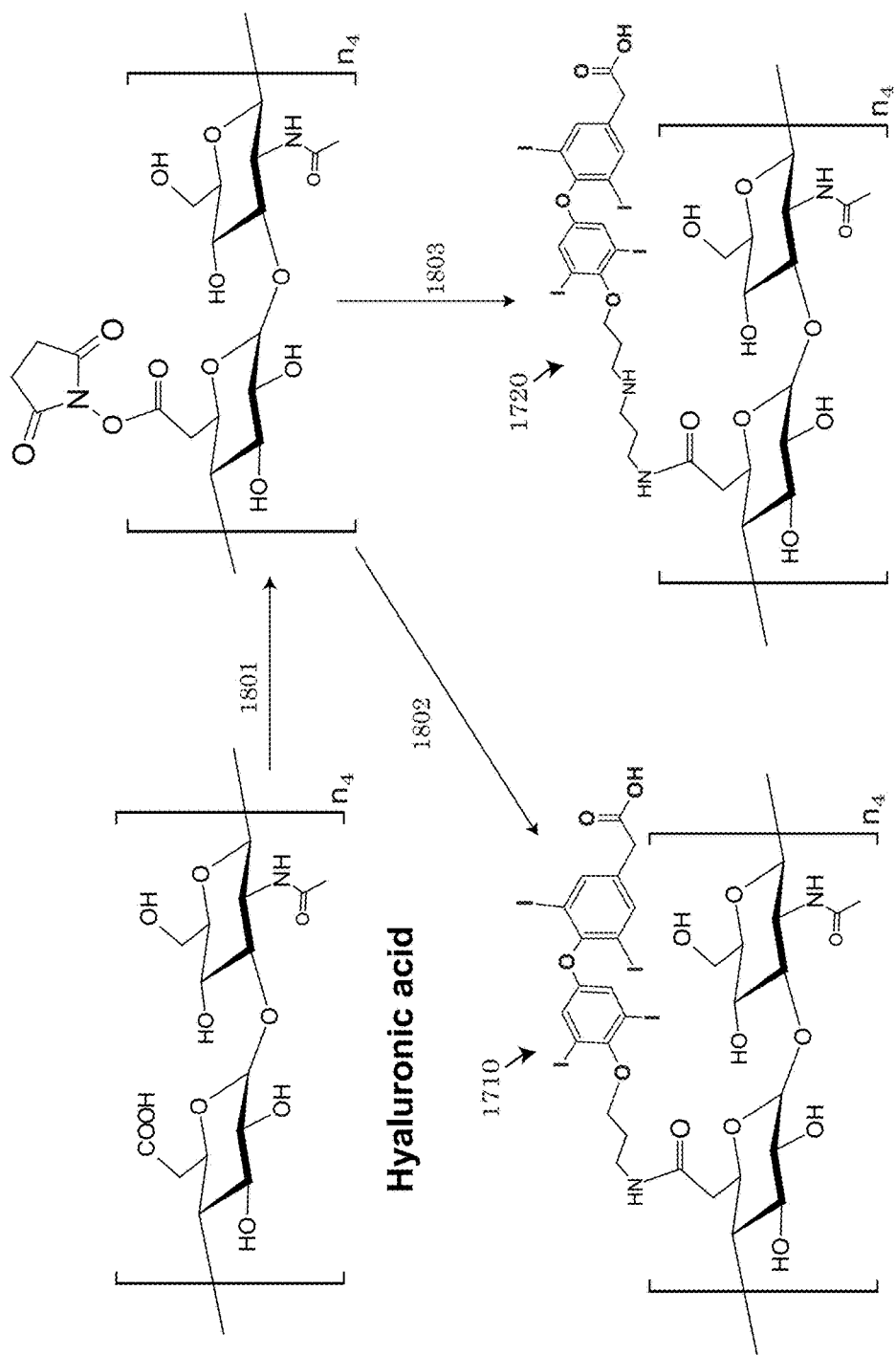
FIG. 18a depicts an embodiment of a method for synthesizing H-MAT and H-DAT from hyaluronic acid.

The synthetization of H-MAT 1710, H-DAT 1720 and H-TAT 1730 follows a similar set of synthetization steps to the polymer conjugated alginic acid methodology of FIG. 16a-16b previously described above. As shown in FIG. 18a, synthesizing method starts with the hyaluronic acid polymer. Instead of tosylating the polymer, step 1801 reacts the hyaluronic acid with NHS to the carboxyl group of the hyaluronic acid polymer. In step 1802 and 1803, the NHS may be removed in a substitution reaction by introducing MAT 210 (step 1802) or DAT 220 (step 1803) to replace the NHS of the hyaluronic acid with either MAT 210, forming H-MAT 1710 or DAT 220 forming H-DAT 1720.

Figure 18B:
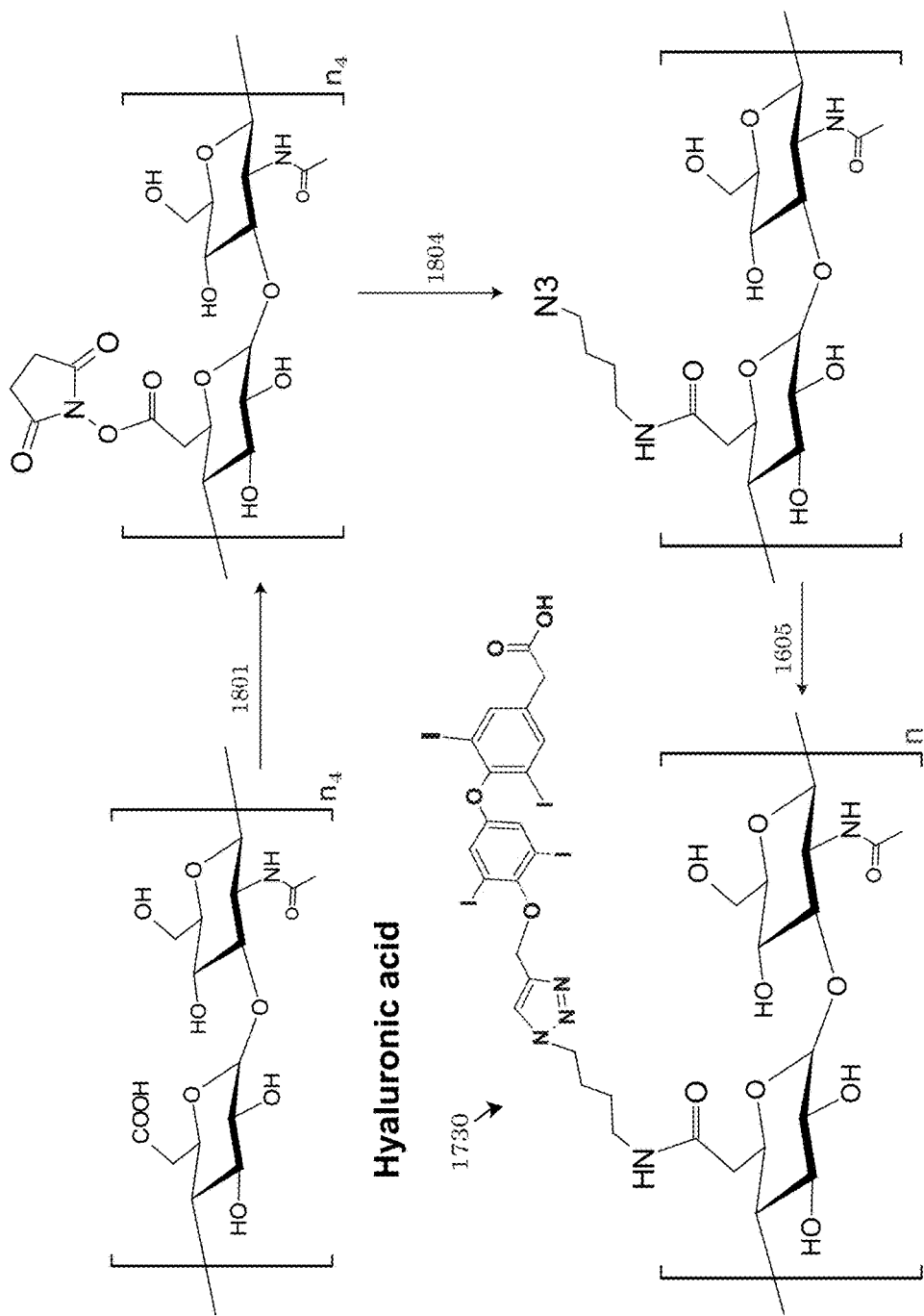
FIG. 18b depicts an embodiment of a method for synthesizing H-TAT from hyaluronic acid.

FIG. 18b depicts the method steps for preparing H-TAT 1730 from a hyaluronic acid starting material. The hyaluronic acid is reacted with the NHS to form NHS-hyaluronic acid in step 1801. In step 1804, the NHS-hyaluronic acid undergoes a reaction with an azido compound, replacing the NHS attached to the carboxyl group of the hyaluronic acid with the azido compound resulting in a hyaluronic acid-azido compound as shown in FIG. 18b. Lastly, the hyaluronic acid-azido compound formed because of step 1804 may be further reacted in step 1805 in the presence of PGT 230 to form a triazole bond with the N3 of the azido group, generating H-TAT 1730.

Polymer-Conjugated Thyrintegrin Antagonist Methods of Use

Example 1 Anti-Angiogenesis Efficacy

Mouse Matrigel-Growth Factors Implant Angiogenesis Model:

The mouse Matrigel model was performed in accordance with institutional guidelines for animal safety and welfare. Female mice C56/BL aged 5-6 weeks and body weights of 20 g were purchased from Taconic Farms (Hudson, N.Y., USA). The animals were maintained under specific pathogen-free conditions and housed 4 animals per cage, under controlled conditions of temperature (20-24° C.) and humidity (60-70%) and a 12 h light/dark cycle. The in vivo study carried out in the animal facility of the Veterans Affairs (VA) Medical Center, Albany, N.Y., and the experimental protocol approved by the VAIACUC. Mice were acclimated for 5 d prior to the start of experiments. Matrigel Matrix High Concentration with growth factors to promote the angiogenesis and the mix was injected four times subcutaneously at 100 µl/animal. Animals in the control group injected just with Matrigel in 100-µl volume.

Figure 21:
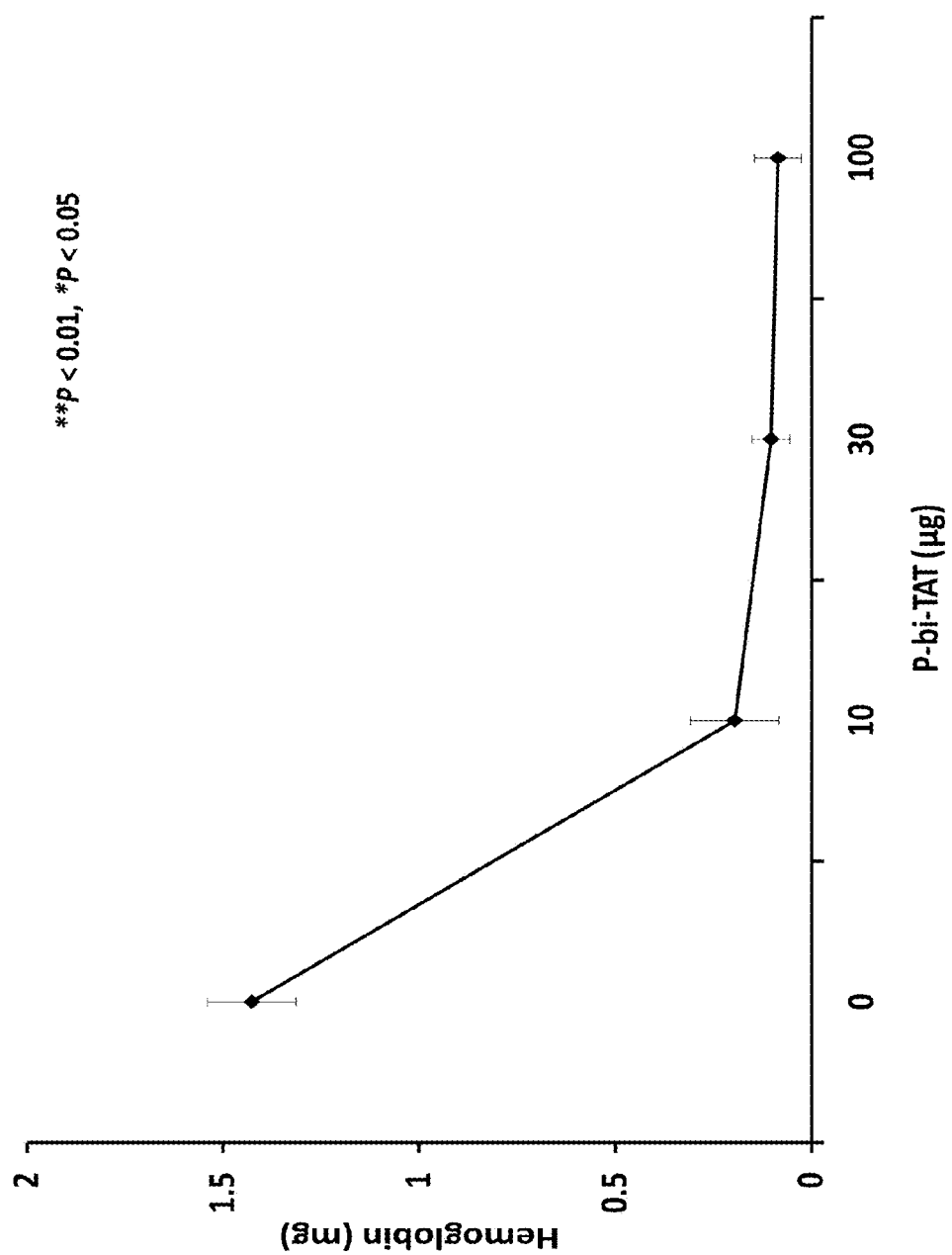
FIG. 21 depicts the effect of P-bi-TAT on Matrigel growth factors implant-mediated angiogenesis in mice and a dose-dependent anti-angiogenesis efficacy for P-bi-TAT in mouse Matrigel growth factor-mediated angiogenesis.

Polymer Conjugated DAT, TAT or MAT derivatives were tested at three different doses (10, 30, 100 µg/10 µl). All groups have three mice per group, with 12 Matrigel subcutaneous injections per group. At day 14-post plug implant, all animals were sacrificed and hemoglobin contents were quantitated using spectrophotometry. FIG. 21 depicts representative data for P-bi-TAT and its effective anti-angiogenesis efficacy against growth factors. As it can be seen in FIG. 21, the anti-angiogenic effects of P-bi-TAT and the other thyrointegrin antagonists measured during this study demonstrated a dose dependent response on angiogenesis, as evident by the measured hemoglobin levels.

Example 2: Determination of Hemoglobin (Hb) Levels (Measure of Angiogenesis Index)

Matrigel plug hemoglobin (Hb) content was indexed as a measure of new vascularity formation. Briefly, Matrigel plugs placed into a 0.5 ml tube containing double distilled water and then homogenized for 5-10 min. The samples were subjected to centrifugation at 4,000 rpm for 10 min and then the supernatants were collected. A volume of 50 µl of supernatant were mixed with 50 µl of Drabkin's reagent and allowed to sit at room temperature for 15-30 min, after which 100 µl was placed in a 96-well plate and absorbance was measured at 540 nm with a Microplate Manager ELISA reader. The Hb concentration was expressed as mg/ml based on comparison with a standard curve.

Example 3: Mousa Subcutaneous Cancer Cell Implant

Figure 22:
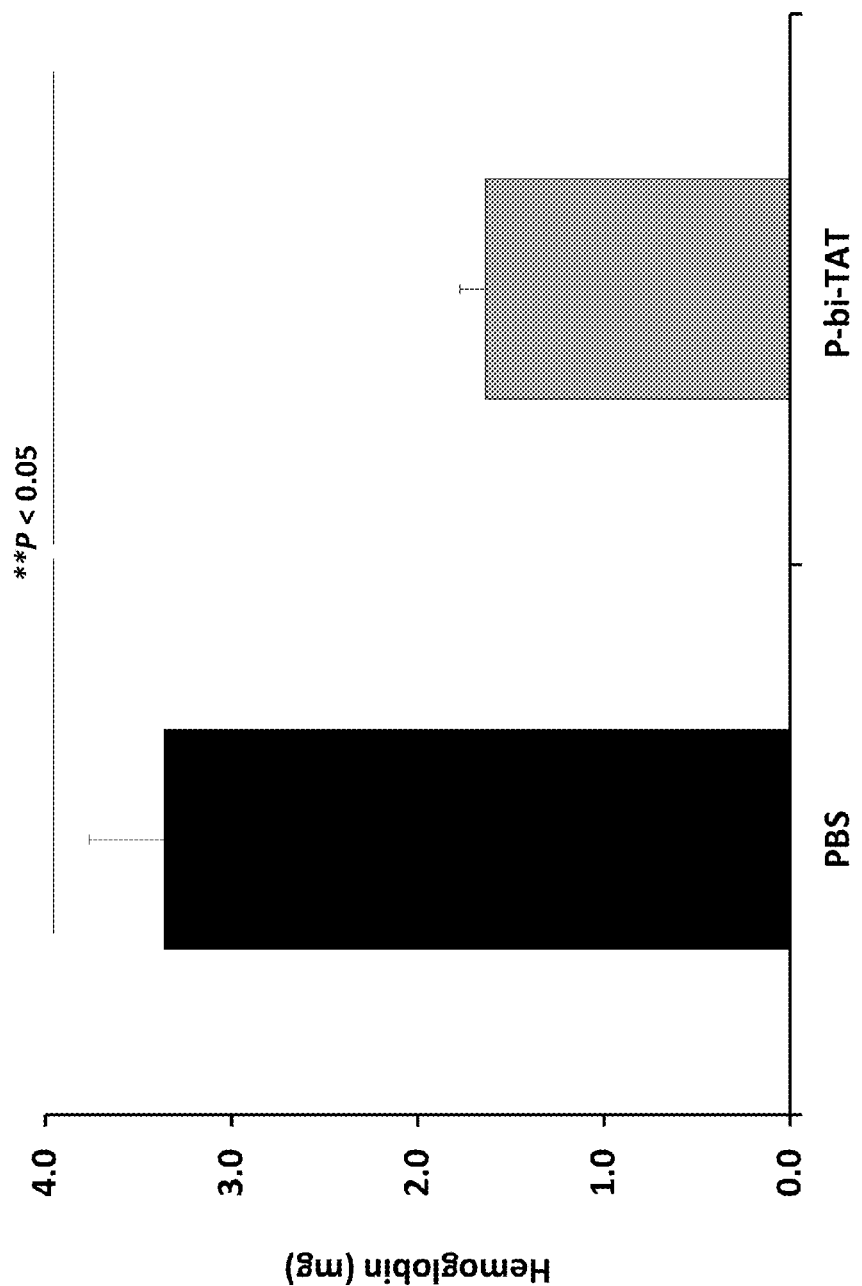
FIG. 22 depicts the effects of P-bi-TAT (1 mg/Kg, SC QD for 14 days) on ovarian (OVCAR3)-tumor angiogenesis in nude mice.

The anti-angiogenesis Efficacy against tumor-angiogenesis was tested using ovarian cancer cell line (OVCAR3) implanted into Matrigel nude female mice. After 14 days of daily treatment (1 mg/kg, SC, QD) with polymer conjugated DAT, MAT and TAT, Matrigel tumor implant removed and analyzed for Hemoglobin. The representative data of the anti-angiogenesis effects against tumor-mediated angiogenesis is depicted as a function the hemoglobin measurement shown by the data of FIG. 22.

Figure 23:
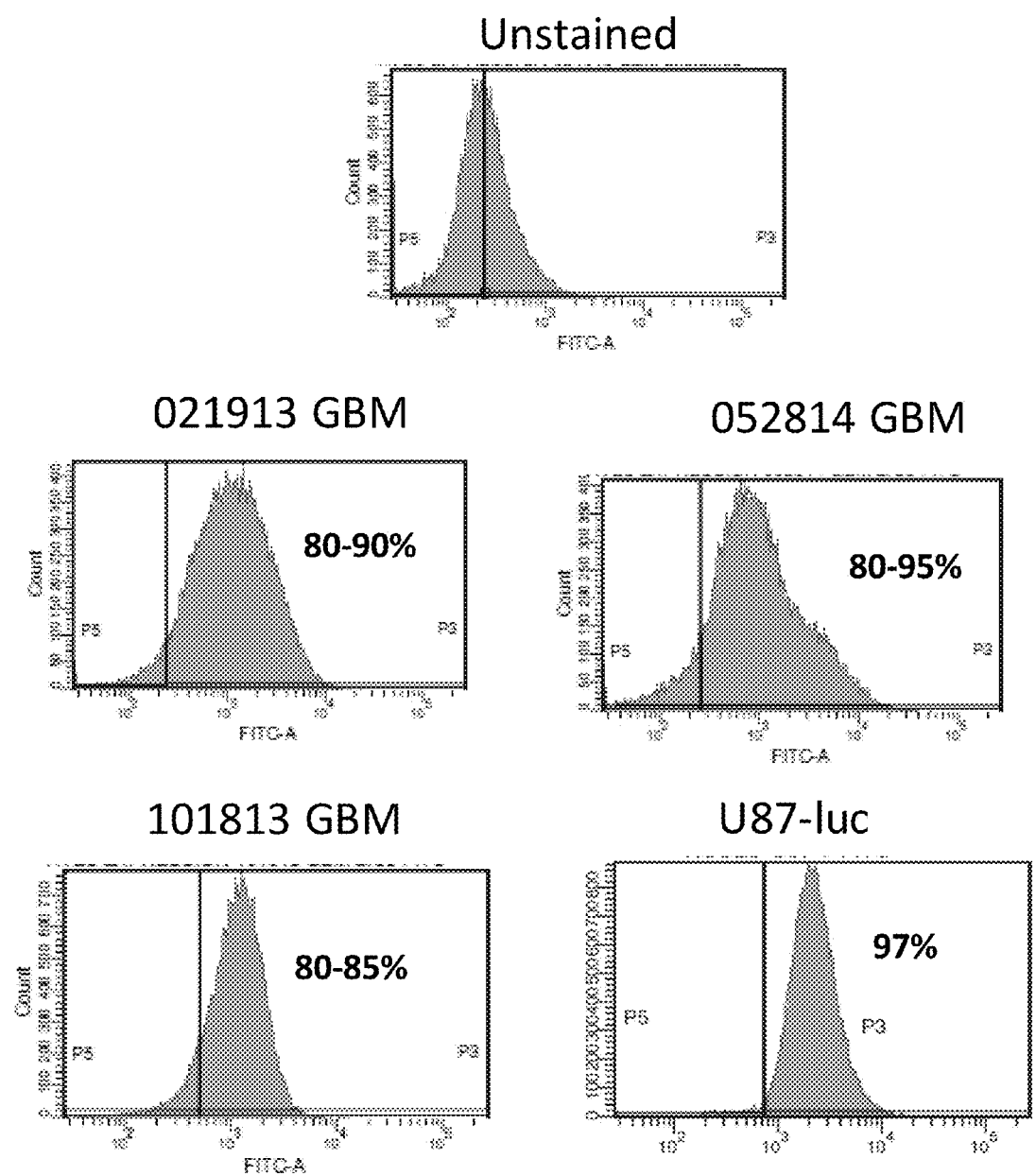
FIG. 23 depicts the expression of αvβ3 protein by flow cytometry.
Figure 24B:
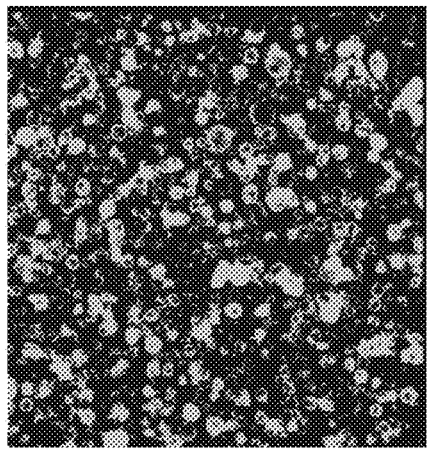
FIG. 24a-24d depicts the expression of αvβ3 protein in GBM cells using confocal microscopy.
Figure 24D:
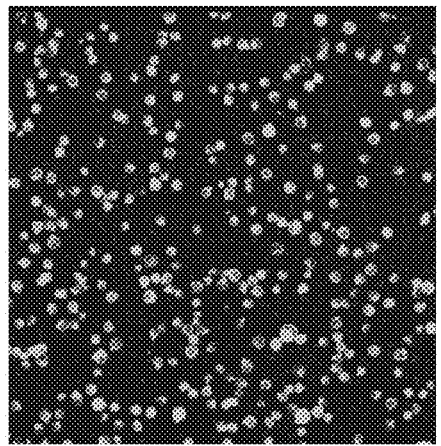
Figure 24A:
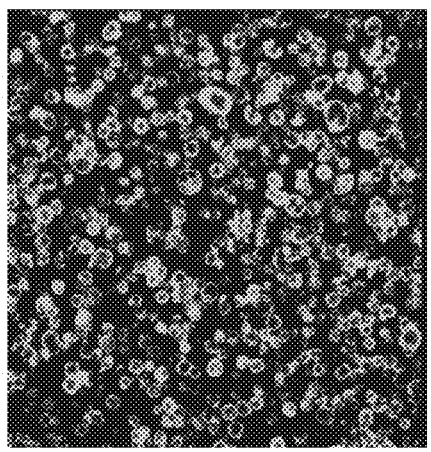
Figure 24C:
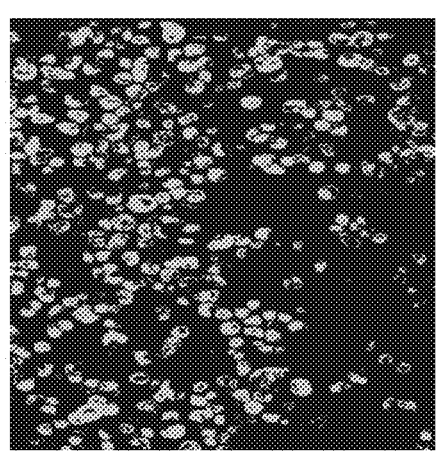

Example 4: Expression of αvβ3 in Different Cancer Cell Lines (Flow Cytometry Analysis)/Confocal Imaging Cells were cultured overnight and cells were collected after a trypsin treatment. Then cells were incubated with FITC conjugated anti αvβ3 for 30 minutes, washed with PBS and the αvβ3 expression studied using flow cytometry as shown in FIG. 23 and Table 3 below. Additionally, the αvβ3 expression levels were observed under a confocal microscope as shown in FIG. 24.

TABLE 3

Expression of αvβ3 for Various Cancer Cells (Flow Cytometry)

| Cancer Cells | Cell Lines | Expression of αvβ3 (%) |
|---|---|---|
| Glioblastoma cell line | U87 | 97 |
| Primary human GBM | 021913 GBM | 90 |
| Primary human GBM | 052814 GBM | 95 |
| Primary human GBM | 101813 GBM | 85 |
| Bladder CANCER | 253JBV | 91 |
| Lung carcinoma | H1299 | 31 |
| Pancreatic cancer | SUIT2 | 32 |
| Pancreatic cancer | MPANC 96 | 22 |
| Breast cancer | MDA MB | 21 |

Figure 25:
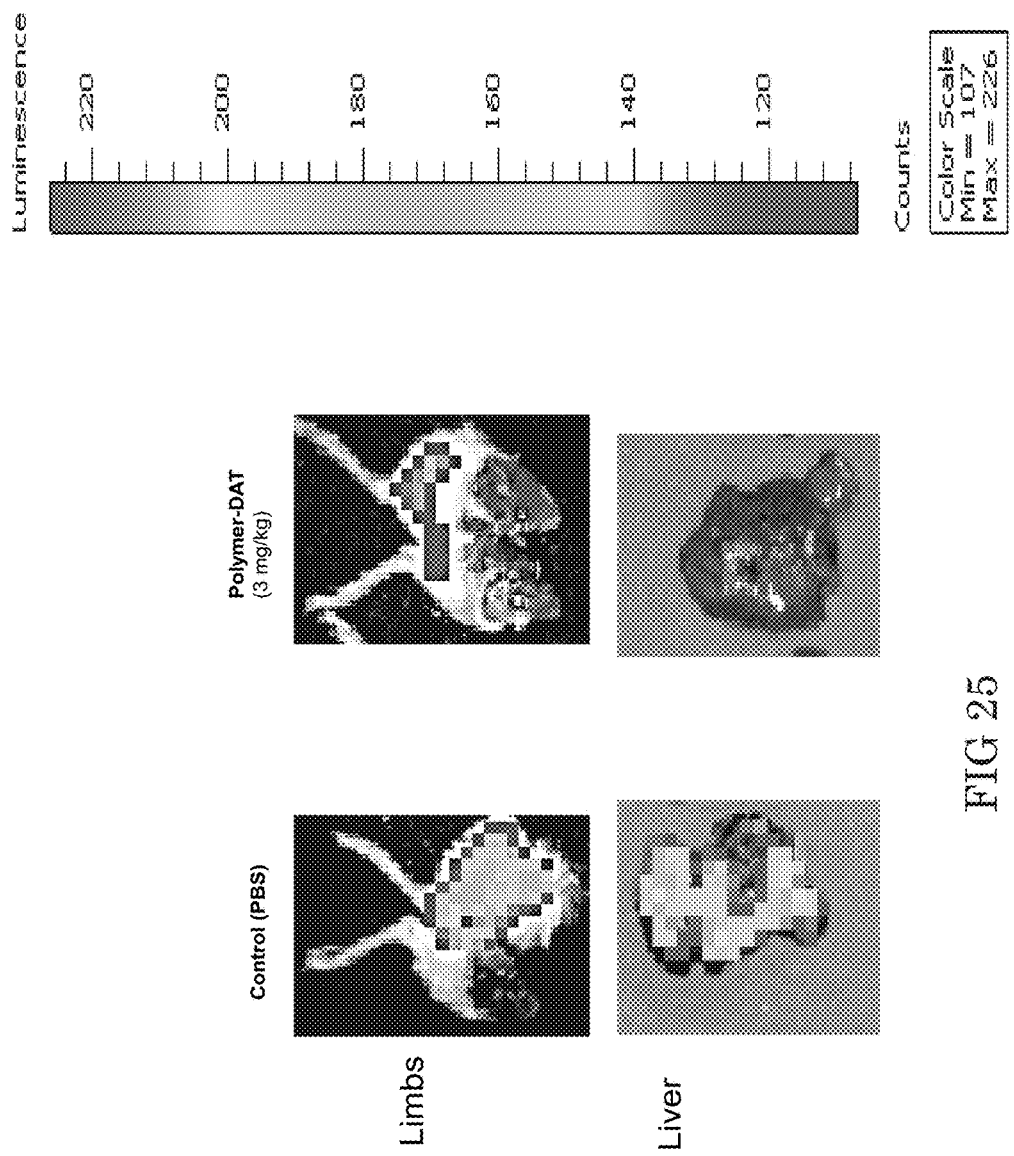
FIG. 25 depicts polymer conjugated DAT decreased bioluminescent signals of THP1-luc cells in the bone marrow and liver metastasis of transgenic mice with Acute Myeloid Leukemia (AML).

Example 5: Acute Myeloid Leukemia Model: Transgenic Mice (NOD.Cg-Prkdcscid) Male THP-1-luc cells were injected intraperitoneally ($5 \times 10^6$ cells in 0.1 ml) into a Control (vehicle) arm and in polymer conjugated diaminotetrac (P-DAT 720) or polymer conjugated triazole tetrac (P-TAT 730) at 3 mg/kg, subcutaneously once a day for 3 weeks. Blood samples were collected before injecting cells, before treatment, and once a week after treatment. Animals terminated after three weeks, carried out via IVIS images of limbs, liver spleen and heart & lungs for luminescent signal intensity of the TPH-1 cells. Additionally, bone marrow smears prepared and Leishman stain was carried out. FIG. 25 describes the representative data of the leukemia model wherein a greater number of blast cells in the control were observed in comparison with the polymer conjugated P-DAT 720 and P-TAT 730.

Figure 26:
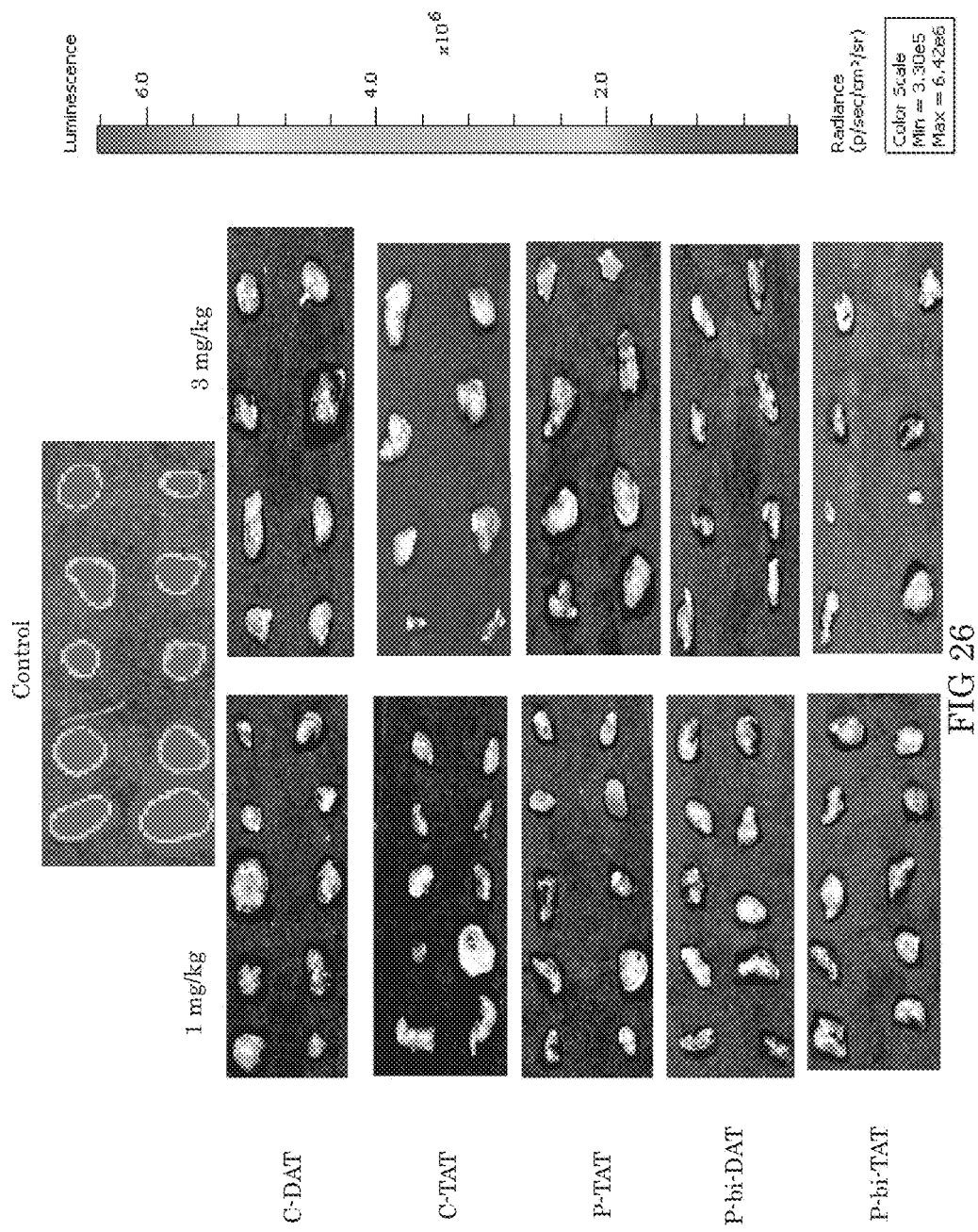
FIG. 26 depicts Bioluminescent signals of the tumors GBM xenografts (21 days on treatment termination), the average bioluminescent signal intensity of the control and void being $2-3\times10^7$ photons/sec and the treated groups (1 mg/kg and 3 mg/kg) having a bioluminescent signal intensity of $<1-2\times10^4$ photons/sec.
Figure 27:
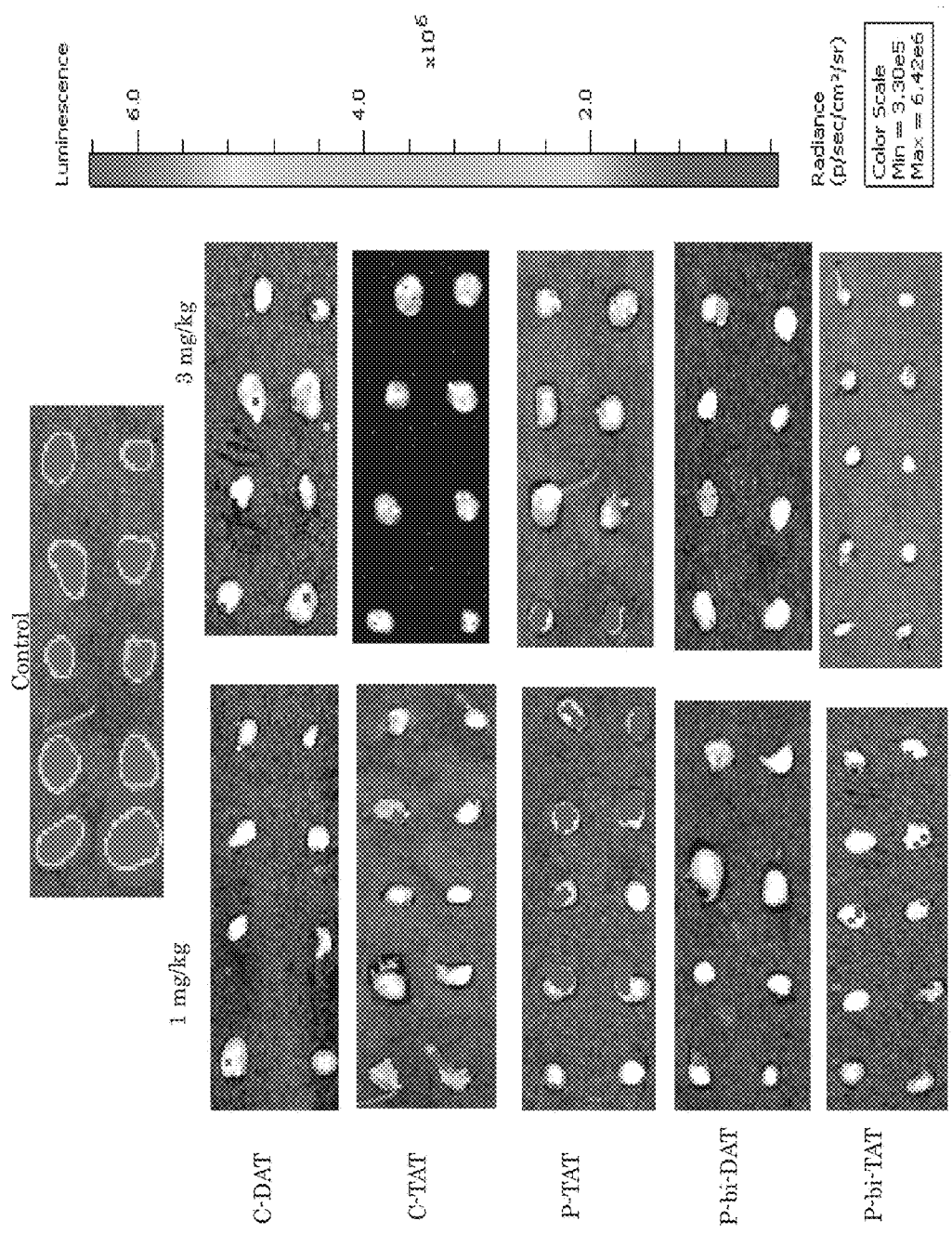
FIG. 27 depicts bioluminescent signals of the tumors GBM xenografts (21 days and 22 days off treatment termination), the average bioluminescent signal intensity of the control and void being $2-3\times10^7$ photons/sec and the treated groups (1 mg/kg and 3 mg/kg) having a bioluminescent signal intensity of $<1-2\times10^4$ photons/sec.

Example 6: Anti-Cancer Efficacy: Effect of Polymer-Conjugated DAT and DAT on U87MG Xenografts in the Nude Mouse The xenograft model of glioblastoma is a standard model for study of GBM. In the current studies, athymic, immunodeficient NCr nude mice aged 5-6 weeks and weighing 18-20 g were used. Animals were provided with ad libitum access to water and food. Animals allowed to acclimatize to the facility for 5 days prior to study. Cultured U87MG-luc cells were harvested and implanted subcutaneously (s.c.) in each flank ($5 \times 10^6$ cells in 100 uL volumes containing 50% Matrigel®). Tumors were grown for 2 days (to an initial volume of 150-250 mm$^3$) before administration of the control, C-DAT 1320, C-TAT 1330, P-TAT 730, P-bi-DAT 1020, P-bi-TAT 1030. Immediately before initiation of treatment at 2 days after implantation, animals were divided into control and treatment groups containing similar distributions of tumor volumes (calipers measurement). Polymer conjugated P-DAT 720 and P-TAT 730 (3 mg or 10 mg/kg body weight) was administered daily s.c. to two groups of animals×21 days, and vehicle (PBS, pH 8.0/0.5% ethanol) was administered daily s.c. to one group of animals as control× 21 days. There were 4 animals and 8 grafts/treatment group. The control group and one group of drug-treated animals humanely sacrificed at 21 days; the second group of drug-treated mice observed off therapy for an additional 22 days to detect any tumor re-growth. The second drug-treated group thus observed for a total of 43 days. Tumors harvested and weighed, then fixed, sliced and subjected to hematoxylin and eosin (H&E) staining. Microscopic slides accommodated the full diameter of the control tumors. See representative FIGS. 25-26 for IVIS imagining of GBM tumors treated with the various polymer-conjugated thyrointegrin antagonists.

Data presented demonstrate that polymer conjugated P-DAT 720 and P-TAT 730 are effective in subcutaneous U87MG glioblastoma xenografts. Administered systemically for 21 days, the drug reduced tumor volumes by fully suppressing angiogenesis, inducing extensive necrosis, and causing apoptosis. While polymer conjugated P-DAT 720 and P-TAT 730 have a single molecular target on βvβ3, the target differentially regulates a network of intracellular signaling pathways and plasma membrane functions that control specific gene transcription and cell surface vascular growth factor receptor functions that are highly relevant to cancer and cancer-relevant angiogenesis. Little αvβ3 is expressed by or activated in non-dividing, non-malignant cells, thus restricting actions of polymer conjugated P-DAT 720 and P-TAT 730 to tumor cells and tumor-associated blood vessel cells. Data in FIGS. 28-30 describe the effects of these various polymer conjugated P-DAT 720 and P-TAT 730 on tumor progression and regression.

Figure 28:
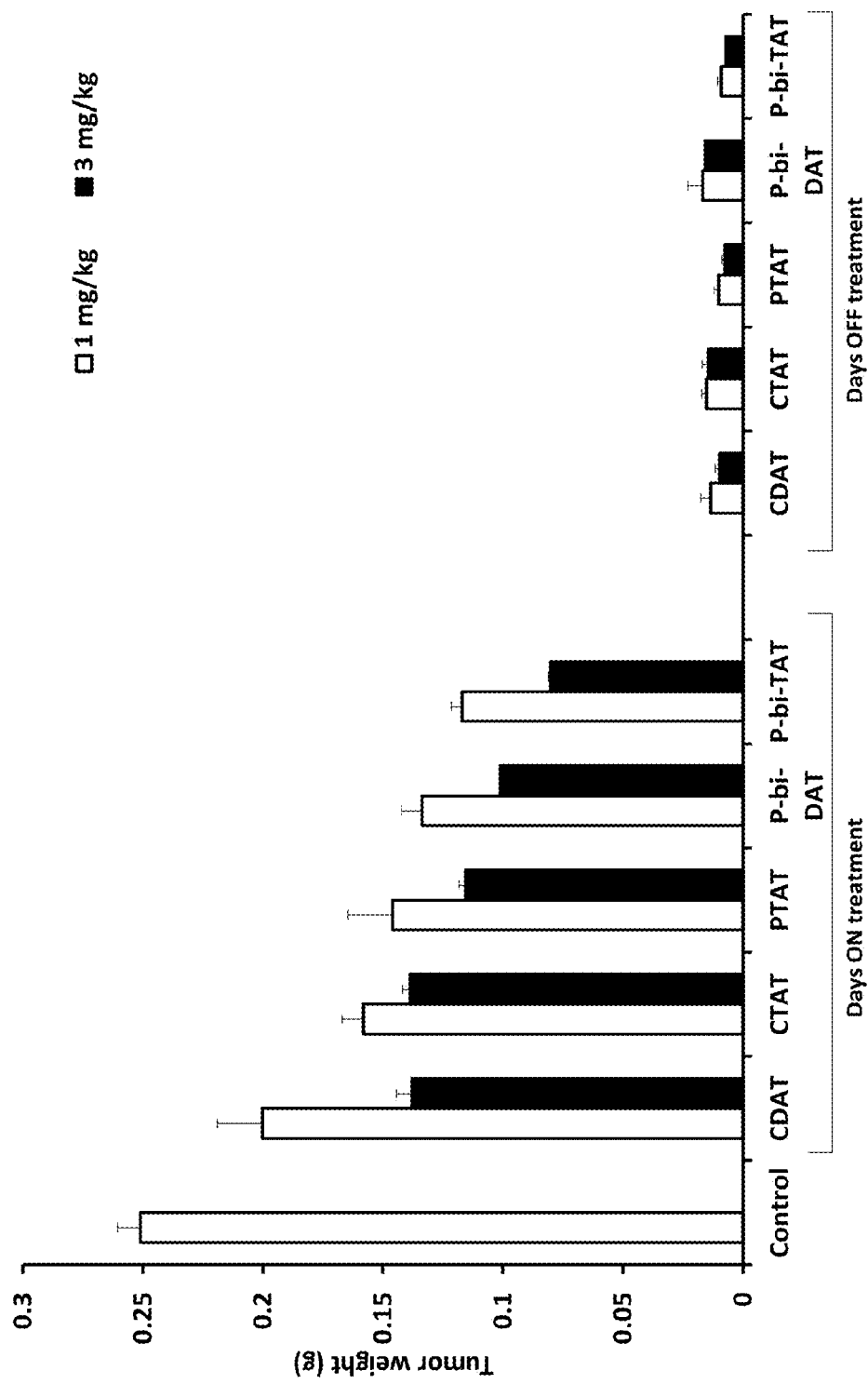
FIG. 28 depicts the effect of polymer Conjugated DAT or TAT on GBM tumor growth in nude mice xenografts after 21 days of daily treatment at 1 and 3 mg/Kg DAT or TAT equivalent (Days ON treatment) and in another arm of 21 days ON followed by 22 Days OFF treatment.
Figure 29:
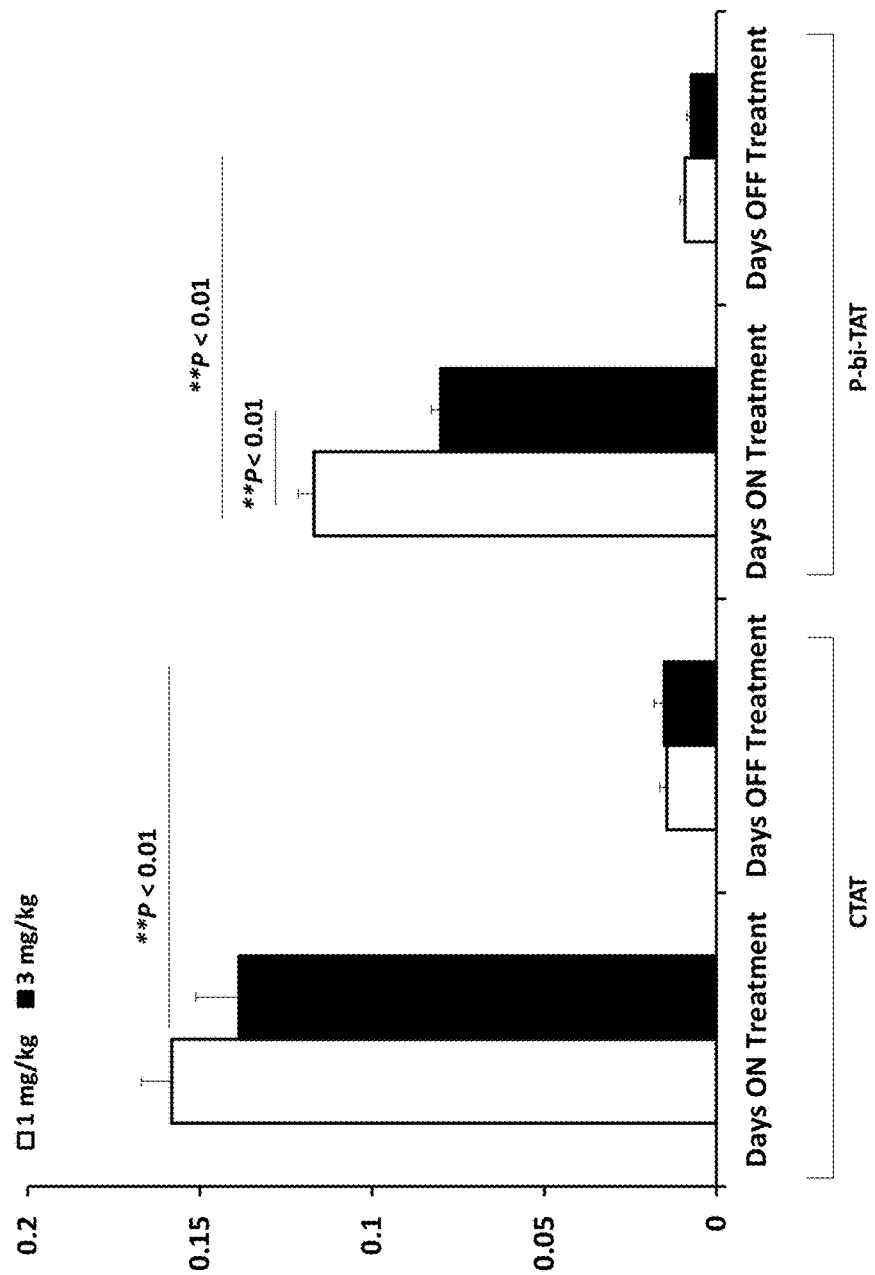
FIG. 29 depicts the effects polymer Conjugated C-TAT and P-bi-TAT on GBM tumor growth in nude mice xenografts after 21 days of daily treatment at 1 and 3 mg/Kg DAT or TAT equivalent (Days ON treatment) and in another arm of 21 Days ON followed by 22 Days OFF treatment.
Figure 30:
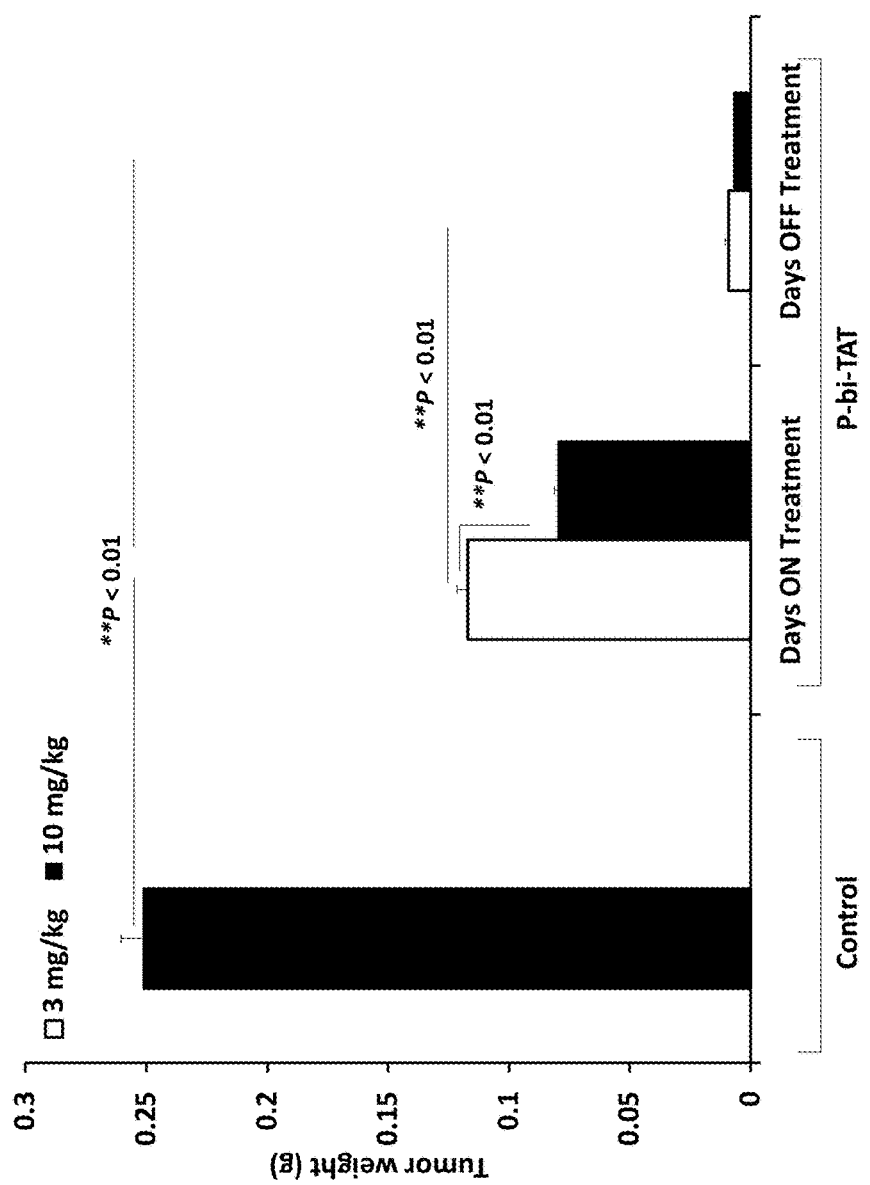
FIG. 30 depicts the effects of polymer conjugated P-bi-TAT on GBM tumor growth in nude mice xenografts after 21 days of daily treatment at 3 and 10 mg/kg, subcutaneously (SC) daily (1 and 3 mg/Kg TAT equivalent, respectively) (Days ON treatment) and in another arm of 21 Days ON followed by 22 Days OFF treatment.
Figure 31:
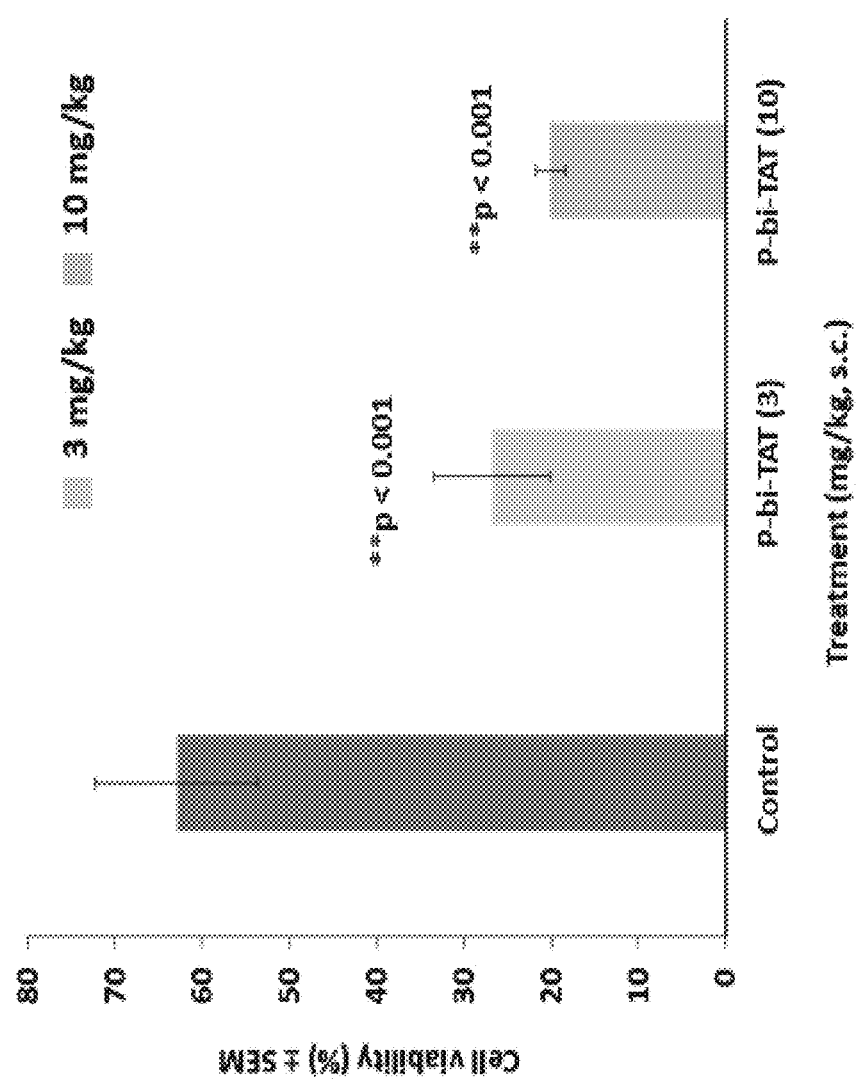
FIG. 31 depicts the loss of tumor cell viability induced by P-bi-TAT in GBM U87MG mouse xenografts. P-bi-TAT (3 mg/kg) and P-bi-TAT (10 mg/kg) are, respectively, daily drug dosages at 3 and 10 mg P-bi-TAT/kg s.c., for 21 days, achieving reductions in cell viability of 62% and 72% (based on histological score). Error bars represent standard error of the mean (S.E.M.).

The data presented in FIG. 28-30 describes the polymer conjugated thyrointegrin antagonists at both 3 and 10 mg/kg dosages dramatically reduced tumor weight. Xenografts in the second group of treated mice, observed for an additional 22 days with no further drug exposure (OFF treatment group), continued to decrease in size, achieving >95% decrease in tumor weight (p<0.01) over the study duration of 43 days at both the 3 and 10 mg/kg doses. The observations presented in FIGS. 28-30 are further supported by histologic assessment of cell viability in xenografts harvested at day 21 (FIG. 31) with P-bi-TAT 1030 as a representative polymer conjugated P-TAT 730**.

Figure 32:
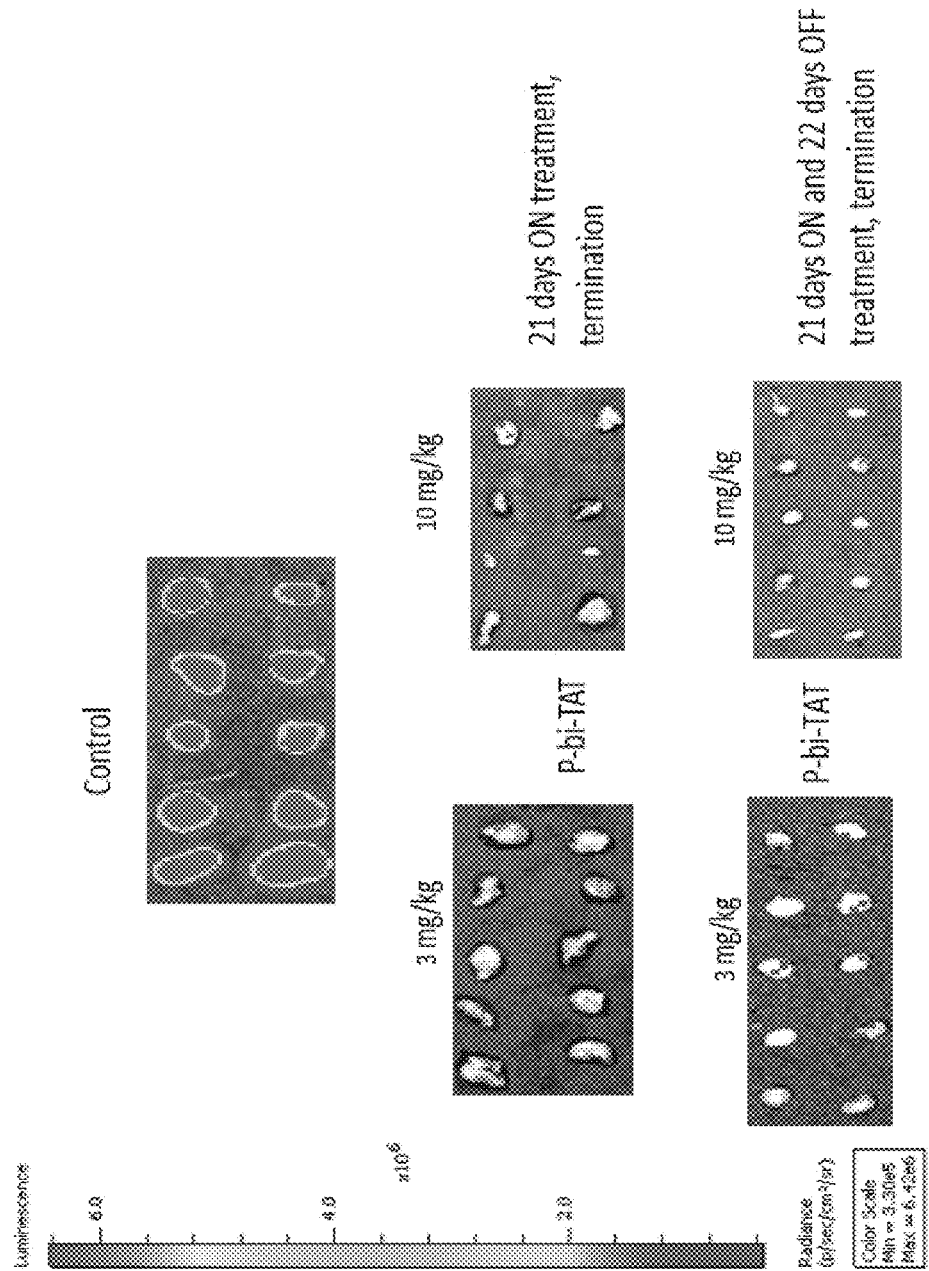
FIG. 32 depicts bioluminescent signals of GBM U87MG-luc mouse xenografts, 21-days ON treatment OR 21-days ON treatment and 22-days OFF treatment before termination. Average bioluminescent signal intensity in control was $2-3\times10^7$ photons/sec. In the treated groups, signal intensity was $<1-2\times104$ photons/sec (limit of detection). In these IVIS images, the vertical luminescence color bar (left margin) estimates viability, ranging from nonviable (0 p/sec/cm$^2$/sr) to fully viable (6 p/sec/cm$^2$/sr).

Histologic evaluation of paraffin-embedded tissue sections were stained (hematoxylin and eosin), and each section was coded. The area of the section measured with a stage micrometer, and the percentage of viable vs. necrotic tumor, manifested by loss of cell density, dissolution of the plasma membrane and loss of nuclear structure estimated visually. The number of mitoses and apoptotic cells per high power field was counted for 5 fields of viable tumor areas and averaged per tissue section. The degree of vascularization varied in the viable areas and this was graded from 1-4. Reductions in cell viability achieved by day 21 were 60-70% in the xenografts exposed to 3 mg/kg and 10 mg/kg dosages of P-bi-TAT 1030 (p<0.001). These findings are consistent with the systematic de-vascularization of tumors leading to necrosis and the multiple pro-apoptotic mechanisms that polymeric P-DAT 720 or P-TAT 730 induce. IVIS Imaging for viable cells (FIG. 32) and histological data (FIG. 31) confirm the effect of P-bi-TAT 1030 as a representative polymer conjugated P-DAT 720 or P-TAT 730** in affecting cancer cell survival.

Figure 33:
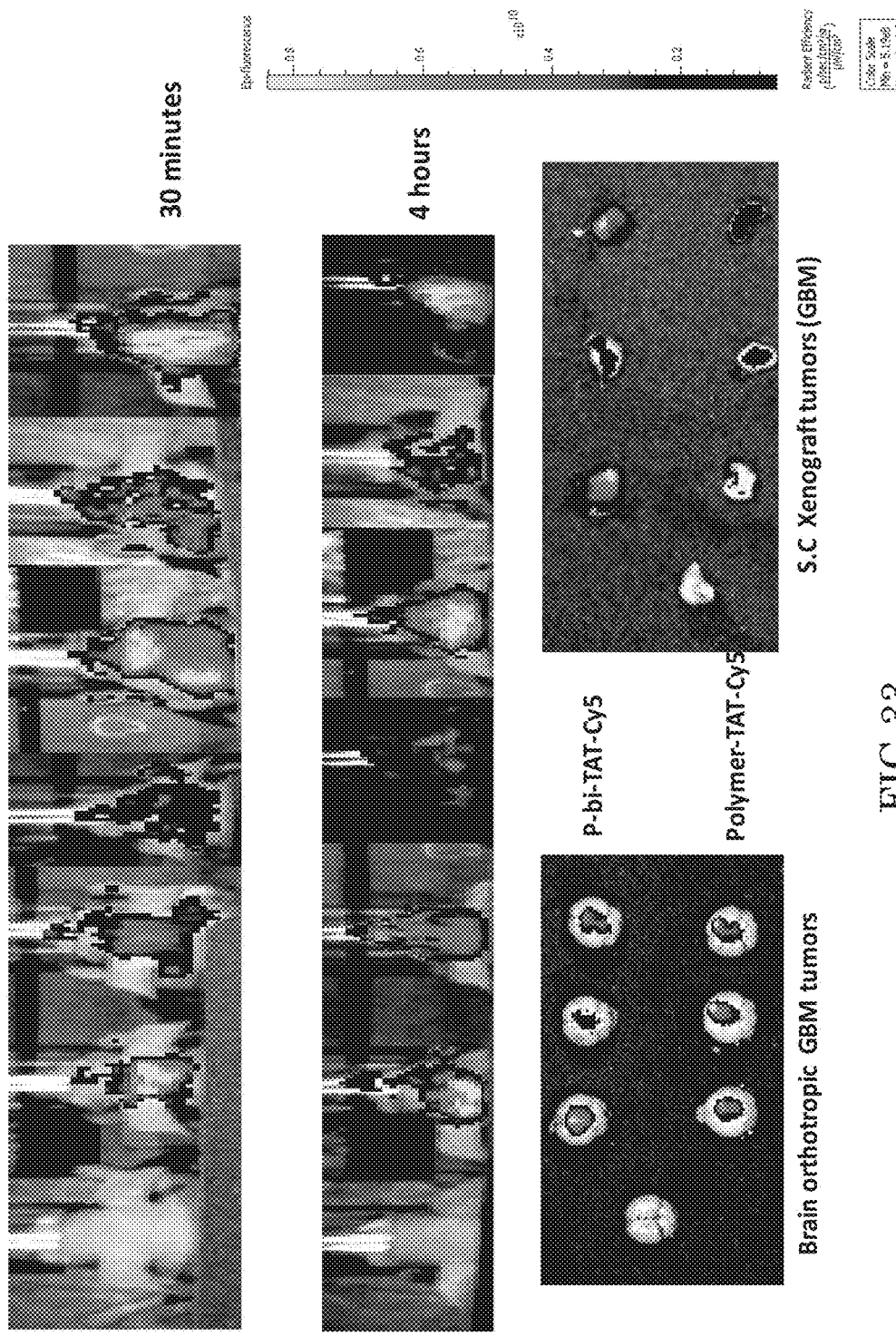
FIG. 33 depicts Cy5 signals in the orthotropic brain (GBM) tumors in vivo at 30 minutes and 4 hours post-administration of P-bi-TAT and other polymer conjugated TAT compositions (upper images). Lower Images illustrate the image intensity for CY5 P-bi-TAT and other polymer conjugated TAT in orthotopic brain GBM tumor and subcutaneous xenograft GBM tumor.
Figure 34:
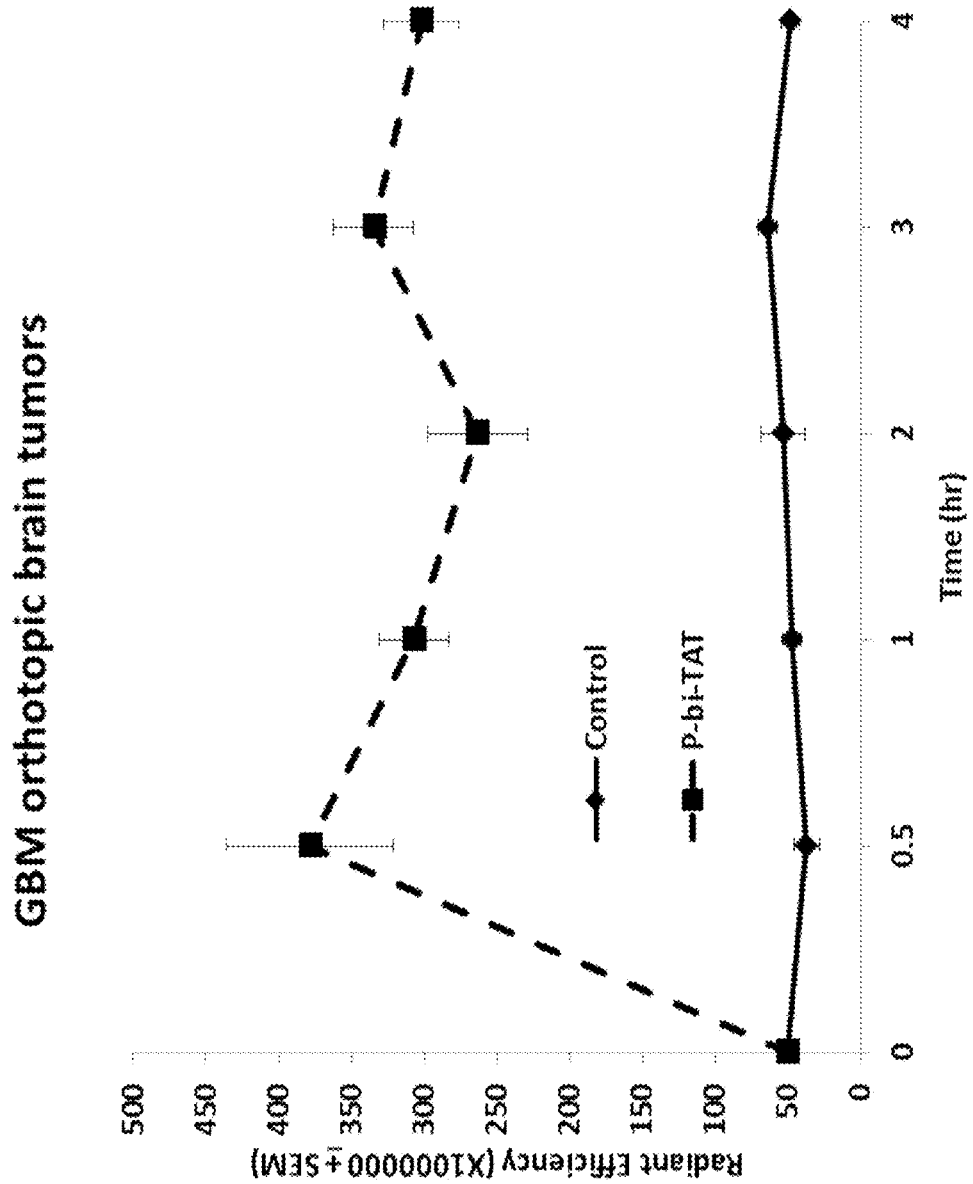
FIG. 34 depicts a graph of an embodiment of the kinetics of CY5 signal intensity of P-bi-TAT in GBM brain tumors.
Figure 35:
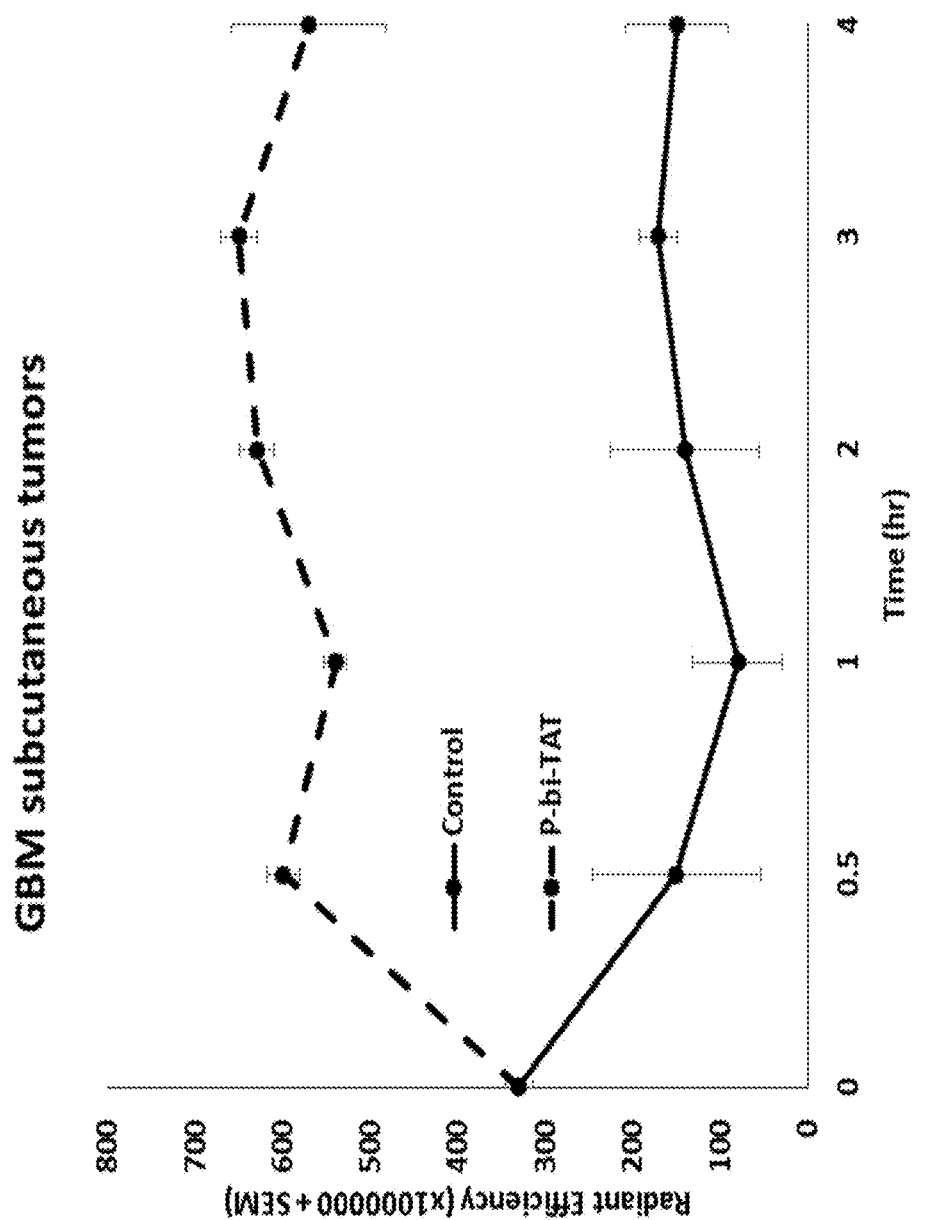
FIG. 35 depicts a graph of an embodiment of the kinetics of CY5 signal intensity of P-bi-TAT in subcutaneous xenograft GBM tumors.

Example 7: Kinetics of Cy5 Labeled P-Bi-TAT and Other Polymer Conjugated Thyrointegrin Antagonist Derivatives Each group of animals was provided with orthotropic implants (GBM) and after tumor growth in the brain and subcutaneously implanted GBM Xenografts. Polymer conjugated MAT 210, TAT 230 or DAT 220 derivatives were injected subcutaneously with P-bi-TAT-Cy5 and other polymer conjugated TAT 230 or DAT 220 derivative-Cy5. IVIS imaging was performed immediately after injection and at 30 min, 1 h, 2 h, 3 h, 4 h to detect the fluorescence intensity at the orthotropic brain xenograft tumor site (brain) and subcutaneous xenografts tumors. FIG. 33 is provided as a representative IVIS imaging illustrating optimal and comparable delivery to GBM in the brain or subcutaneously implanted tumors. The graphs depicted in FIGS. 34 and 35 describe the kinetics of the thyrointegrin antagonist derivatives' uptake into GBM tumors in the brain or subcutaneously implanted tumors. FIGS. 34-35 describe the effects of the polymer conjugated thyrointegrin antagonist derivatives containing MAT 210, DAT 220 and TAT 230 over time including bifunctional embodiments thereof.

Figure 36:
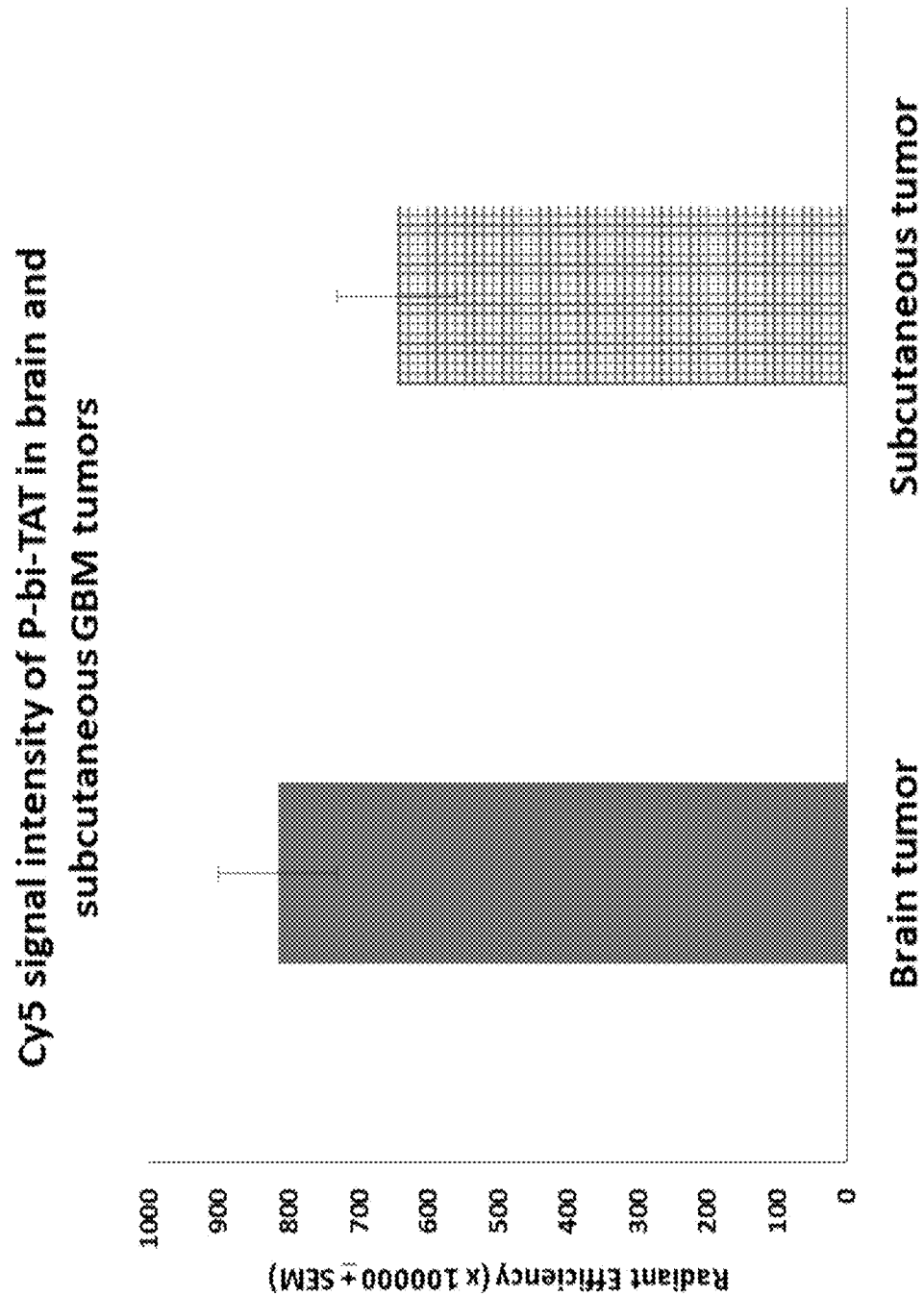
FIG. 36 depicts an embodiment of a graph describing Cy5 Labeled P-bi-TAT signal intensity in brain and subcutaneous GBM tumors removed at the end of the study (4 hours).

Cy5 signals of P-bi-TAT 1030 and polymer conjugated P-TAT 730 derivative-Cy5 was seen in the brain at 30 minutes and sustained for the 4 hours of monitoring with IVIS. Animal terminated after 4 hours and Cy5 signals detected in the brain GBM tumor and subcutaneous GBM tumor xenografts. Cy5 signal was comparable in the brain GBM tumor and the subcutaneous GBM tumor xenografts. FIG. 36 illustrate the comparable uptake into GBM in the brain and subcutaneously implanted tumor xenografts.

Example 8: Effect of P-Bi-TAT on GBM (U87-Luc) Xenografts (Orthotropic and Subcutaneous)

Figure 37:
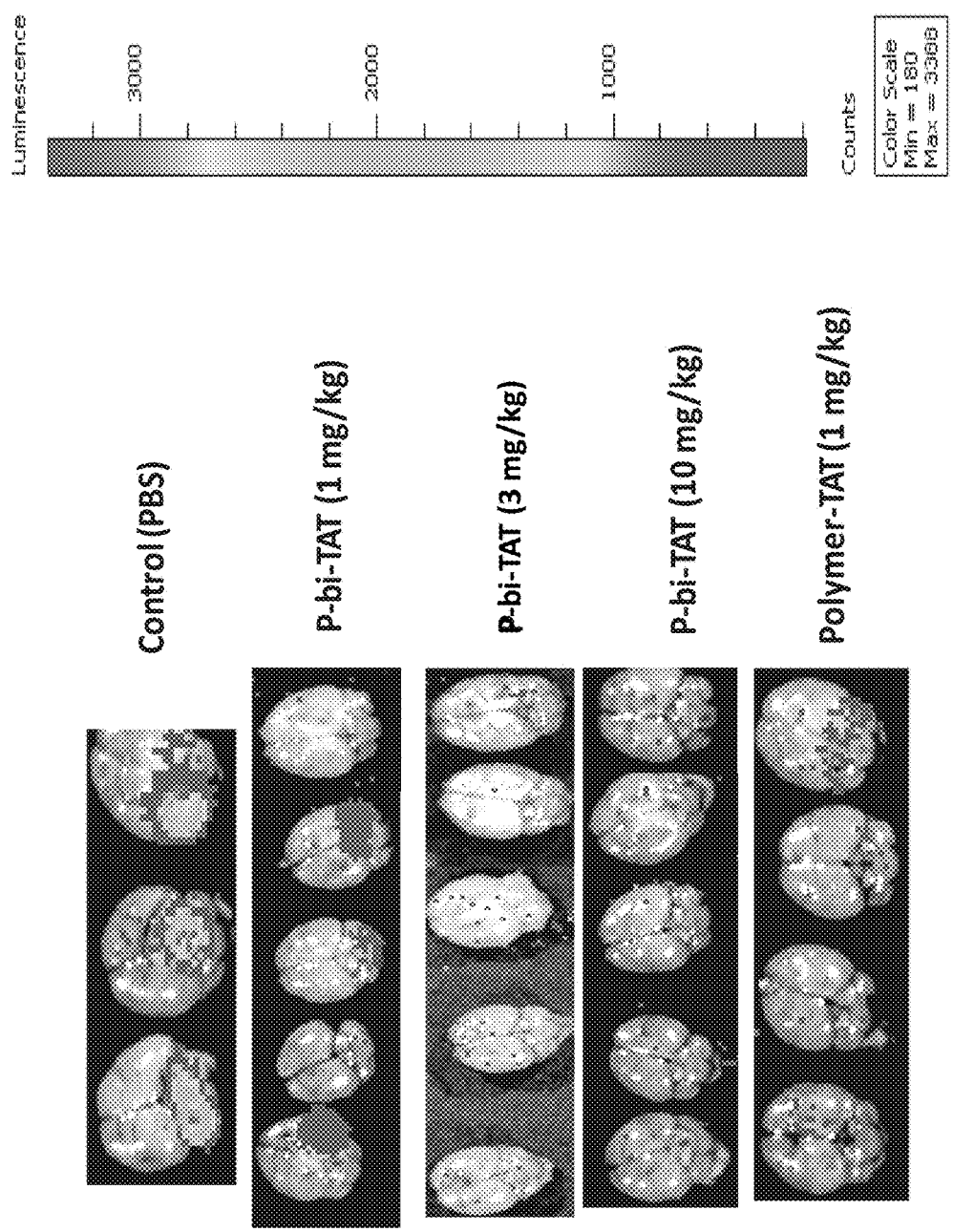
FIG. 37 depicts bioluminescent signals of GBM (U87-luc) orthotropic tumors in brain of a control versus P-bi-TAT treated animals at 1, 3 and 10 mg/kg, SC daily for 7 days.
Figure 38:
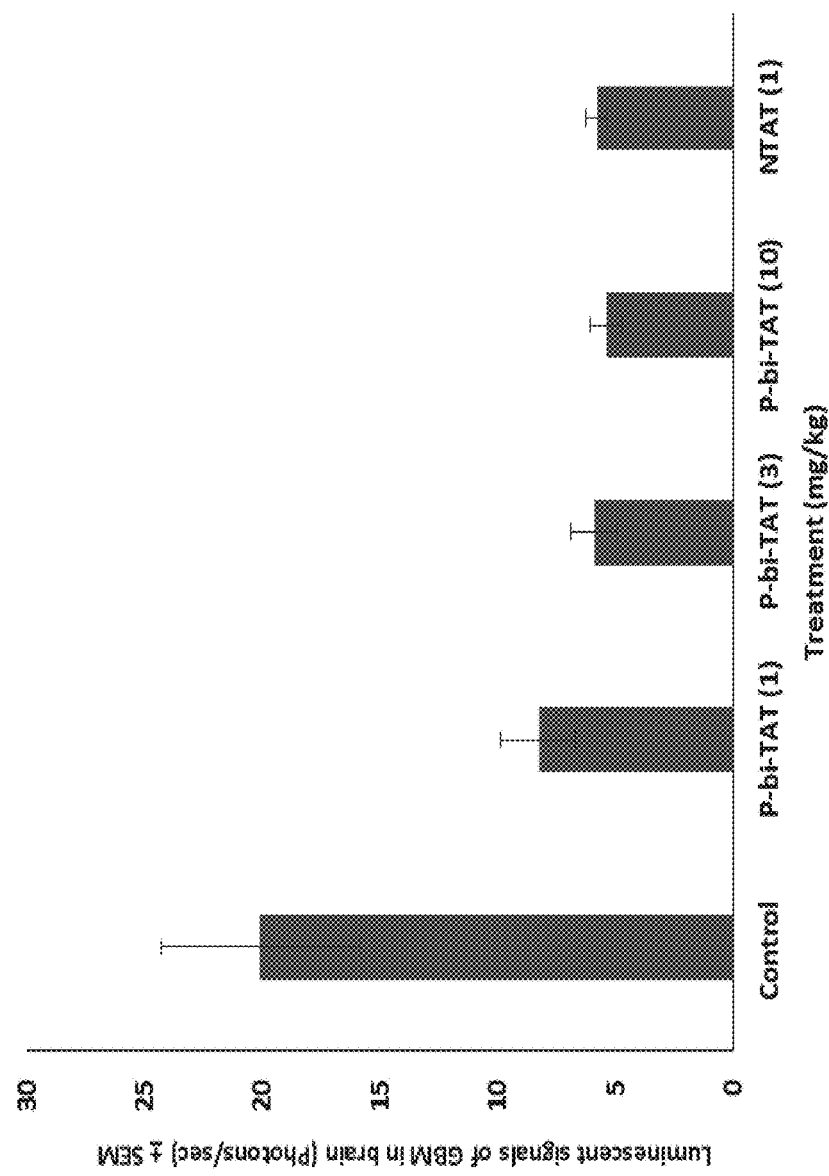
FIG. 38 depicts a graph describing the effects of P-bi-TAT and NTAT (Polymer Conjugated TAT at 1 mg/kg, SC daily for 7 days) on bioluminescent signals of GBM (U87-luc) in the brain.
Figure 39:
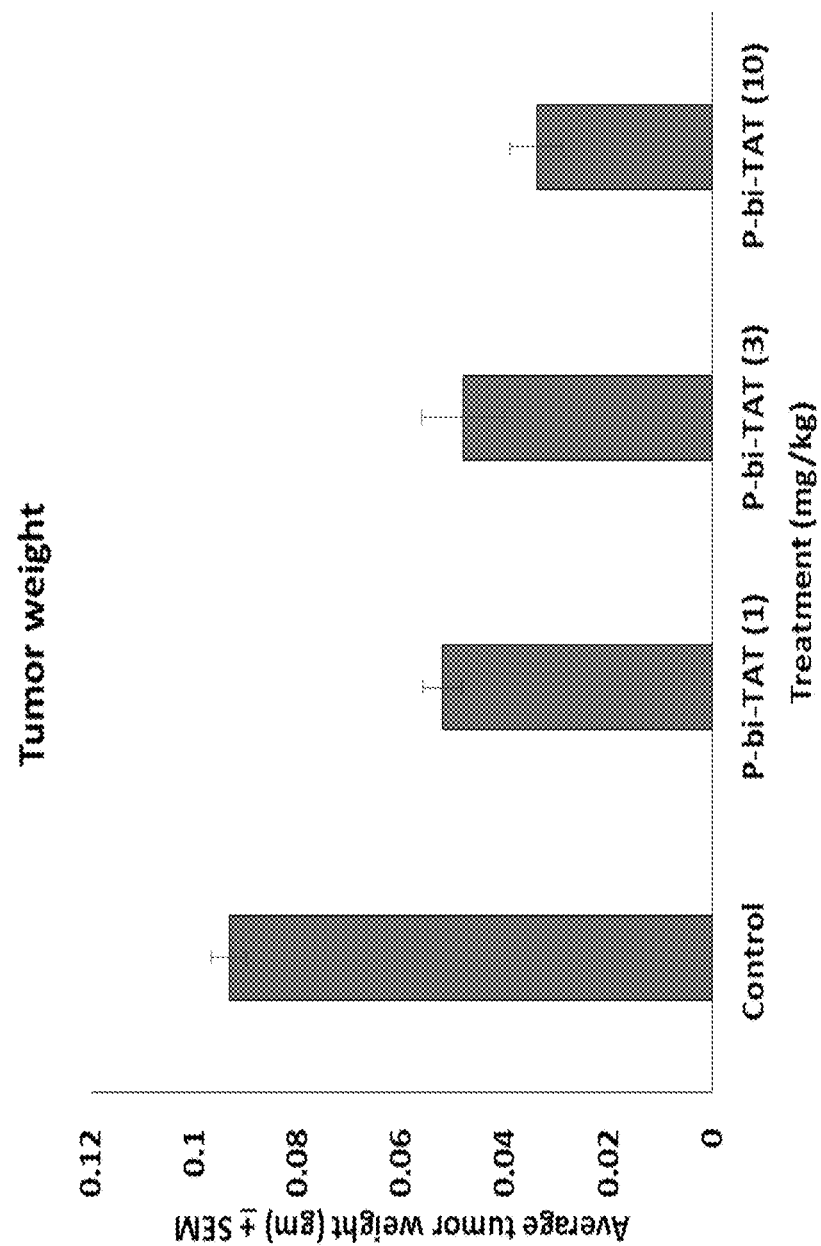
FIG. 39 depicts a graph describing the results of the effect of P-bi-TAT on GBM subcutaneous tumor growth after one-week treatment.
Figure 40:
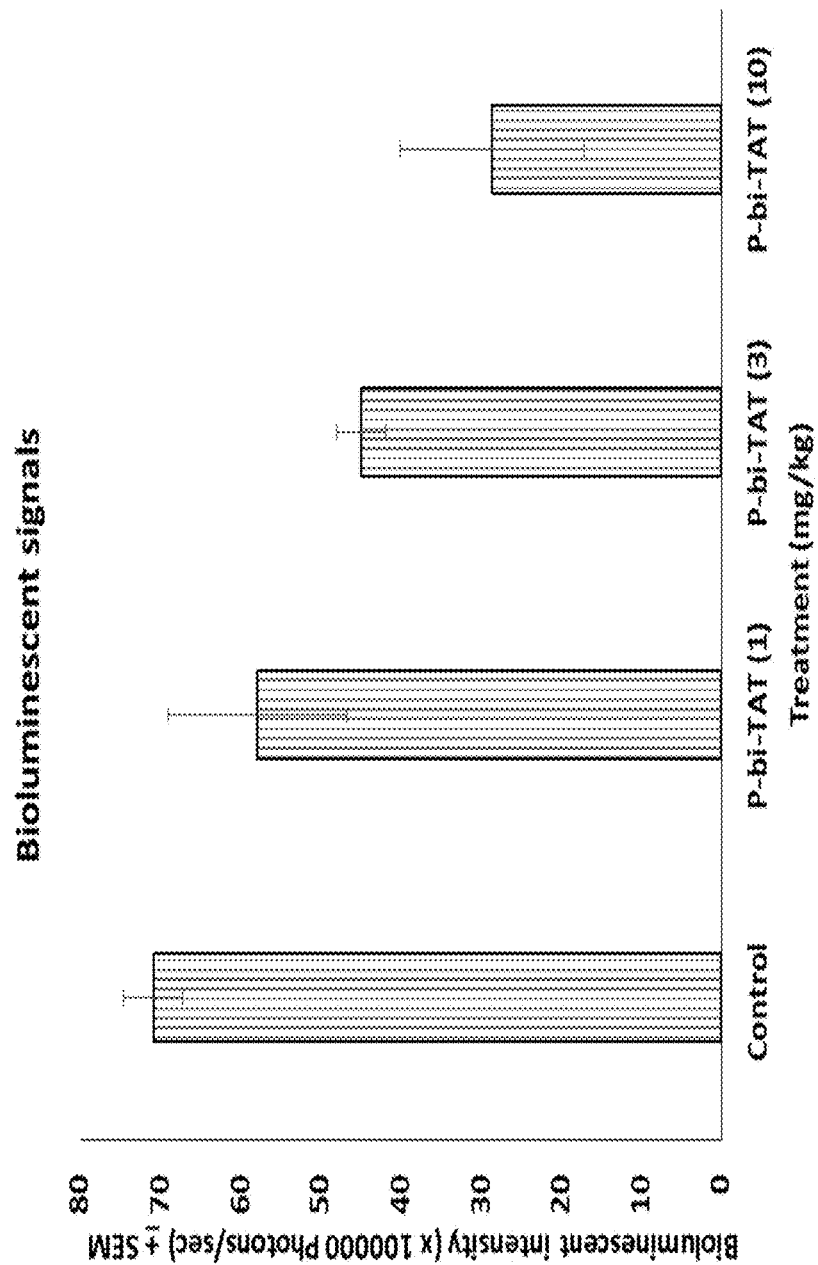
FIG. 40 depicts a graph describing the dosing effects of P-bi-TAT on GBM tumor viability using IVIS imaging.

Glioblastoma cells: U87-luc cells implanted orthotopically at $0.2 \times 10^6$ cell in 20 ul, in Matrigel and subcutaneously xenografted at $2 \times 10^6$ cells/implant with Matrigel in athymic female mice. Animals treated with polymers conjugated thyrointegrin antagonists, including derivatives of P-DAT 720, P-TAT 730 and bifunctional derivatives thereof for 7 days after 1 day post-implant and IVIS imaging of the brain tumor and subcutaneous tumor xenograft. FIG. 37 describe the dose dependent suppression of the tumor using P-bi-TAT 1030, including the suppression of cell viability in brain GBM tumor and subcutaneous GBM tumor. FIGS. 38-40 depict the measurable dose-dependent effects of p-bi-TAT 1030 on brain GBM tumor and subcutaneous GBM tumor including the effect on luminescent signals of GBM in the brain, average tumor weight and bioluminescent intensity.

Example 9: Effect of P-Bi-TAT on Pancreatic Cancer SUIT 2 Xenografts

Female NCr mice (Taconic Farms, Hudson, N.Y.) for in vivo studies obtained at 5-6 weeks of age (20 gm body weight) and maintained under specific pathogen-free conditions, and food and water provided ad libitum. The animals allowed to acclimate for 5 days. Cultured human SUIT 2 cells were harvested and implanted subcutaneously (s.c.) in each flank of the mice. Inocula comprising 100 μL, 50% Matrigel®, and containing 2×10$^6$ tumor cells was prepared. Tumors were grown for 7 days, at which time the animals were randomized into control and P-bi-TAT groups (6 animals/group, 12-carcinoma grafts/group). Starting on day 0, drug was administered at 3 or 10 mg of P-bi-TAT/kg body weight, daily for 20 days (to experimental day 19). Control animals received vehicle (PBS) daily. Animals were sacrificed on experimental day 20. Tumors were harvested and the weight of the tumors were measured. Tumors were formalin-fixed, imbedded in paraffin and sliced.

Effectiveness of radiation therapy, alone and in conjunction with P-bi-TAT was also assessed. The Radiation treatment was one Gy administered to right flank xenografts on days 10 and 17. Geometry of flank exposure excluded radiation exposure to the left flank of study animals, so that the left flank served as a control in the radiation studies.

Figure 41:
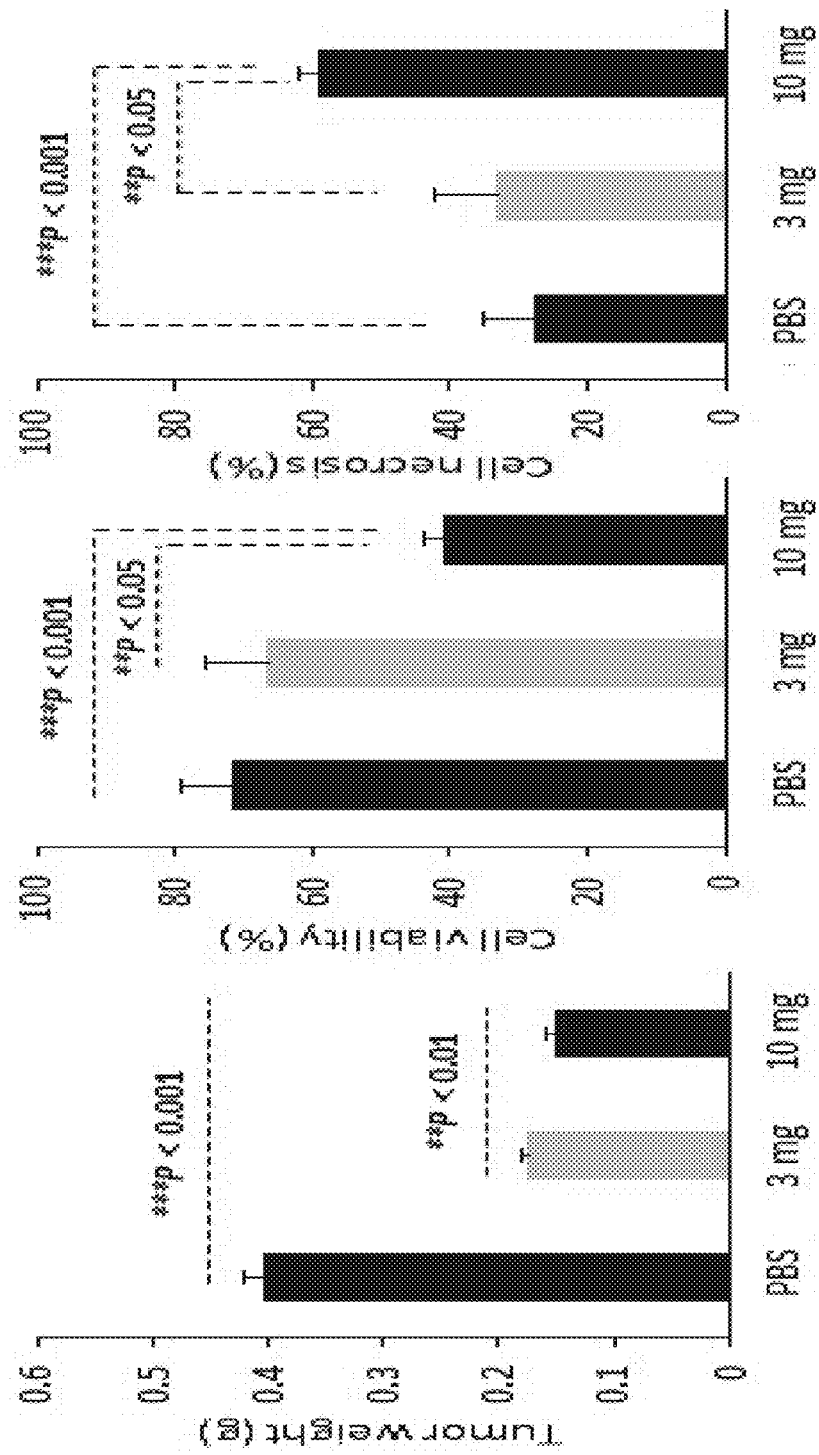
FIG. 41a depicts a graph of the anticancer efficacy of P-bi-TAT on pancreatic cancer, SUIT 2, at 3 mg/kg and 10 mg/kg compared with a control as a function of tumor weight.
FIG. 41b depicts a graph of the anticancer efficacy of P-bi-TAT on pancreatic cancer, SUIT 2, at 3 mg/kg and 10 mg/kg compared with a control as a function of cell viability.
FIG. 41c depicts a graph of the anticancer efficacy of P-bi-TAT on pancreatic cancer, SUIT 2, at 3 mg/kg and 10 mg/kg compared with a control as a function of % cell necrosis.

The effects of a representative polymer-conjugated thyrointegrin antagonist (P-bi-TAT 1030) on tumor weight, cell viability and cell necrosis was studied. Anticancer efficacy of P-bi-TAT on pancreatic cancer SUIT 2 xenograft weight, cell viability and cell necrosis shown in FIG. 41*a*-41*c*. The Tumor weight reduction after 20 days was 55% with the administration of P-bi-TAT at 3 mg/kg and 65% at 10 mg/kg (each *$P<0.001$ vs. control) (FIG. 41***a*). Percent reduction in tumor cell viability was insignificant at a drug concentration of 3 mg/kg and was 43% at 10 mg/kg (*$P<0.001$ vs. control) as shown in FIG. 41***b*. The increase in % cell necrosis in tissue sections was not significant at 3 mg/kg of P-bi-TAT, but there was more than a doubling of necrosis at a dose 10 mg/kg (*$P<0.001$ vs. control) as shown by the data in FIG. 41**C. Thus, in these short-term studies with P-bi-TAT, there were desirable alterations in tumor size and in histologically estimated cancer cell viability and necrosis.

Interactions of Radiation Exposure and P-Bi-TAT Administration:

The effects of radiation exposure, alone, and radiation in conjunction with P-bi-TAT on pancreatic cancer SUIT 2 xenograft weight, cell viability and cell necrosis is depicted in FIG. 42*a*-42*c*. Radiation treatment, alone, at one Gy to the right flank xenografts caused a decrease in tumor weight of these xenografts of 38% vs. left flank xenografts, which were unexposed to radiation (FIG. 42*a*). The combination of radiation and the exemplary embodiment the polymer conjugated thyrointegrin antagonist tested P-bi-TAT 1030 resulted in further decreases in tumor size of 71% (3 mg P-bi-TAT/kg) and 77% (10 mg P-bi-TAT/kg) (each ***$P<0.001$ vs. non-irradiated control). There was no P-bi-TAT dose effect on tumor weight when drug and radiation combined.

Figure 42:
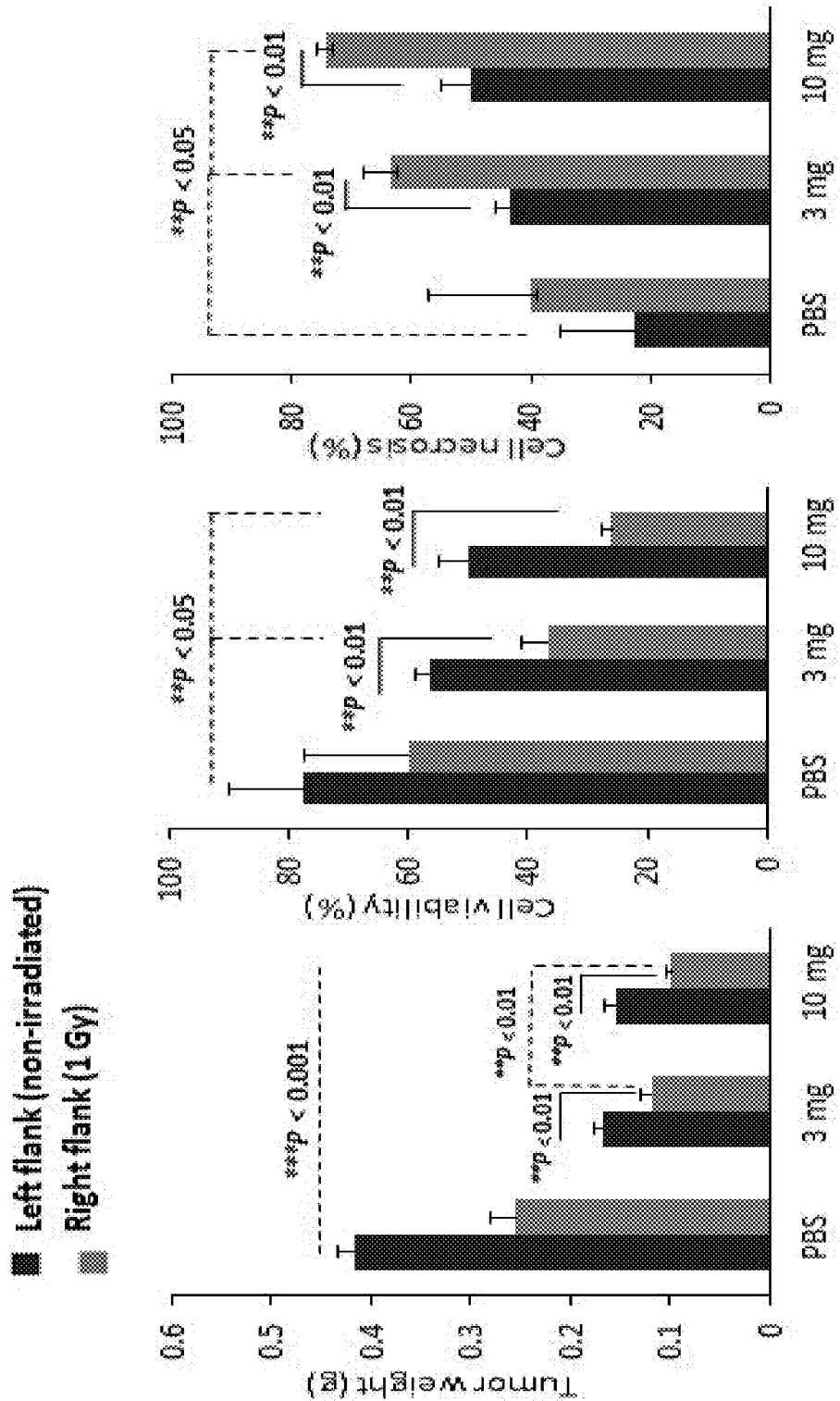
FIG. 42a depicts a graph describing the effects of radiation/non-radiation exposure alone (PBS), and radiation or none/radiation exposure in conjunction with dosages of P-bi-TAT (3 mg/kg and 10 mg/kg) on pancreatic cancer SUIT 2, the effects being described as a function of xenograft tumor weight.
FIG. 42b depicts a graph describing the effects of radiation/non-radiation exposure alone (PBS), and radiation or none/radiation exposure in conjunction with dosages of P-bi-TAT (3 mg/kg and 10 mg/kg) on pancreatic cancer SUIT 2, the effects being described as a function of % cell viability.
FIG. 42c depicts a graph describing the effects of radiation/none-radiation exposure alone (PBS), and radiation or none/radiation exposure in conjunction with dosages of P-bi-TAT (3 mg/kg and 10 mg/kg) on pancreatic cancer SUIT 2, the effects being described as a function of % cell necrosis.
Figure 43:
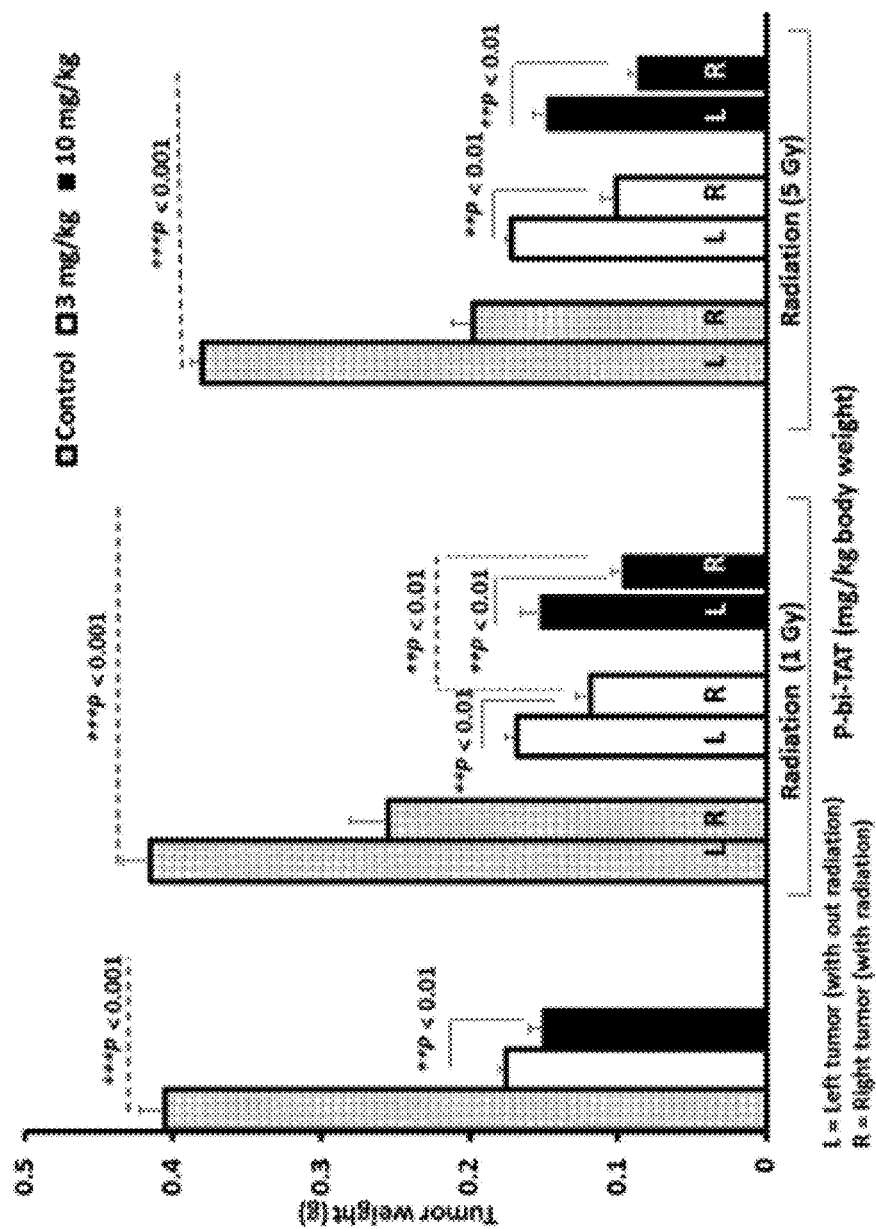
FIG. 43 depicts a graph describing the effects of radiation exposure alone and radiation exposure in conjunction with dosages of P-bi-TAT on pancreatic cancer SUIT 2 at 1GY and 5GYs of radiation with the results depicted as a function of xenograft tumor weight.

As shown in FIG. 42*b*, a decrease in % cell viability was shown at 1 Gy without P-bi-TAT was without statistical significance, but the combination of radiation and drug at 3 mg/kg resulted in a 54% decrease in viability and a 68% decrease was observed at 10 mg/kg (each $P<0.05$ vs. non-irradiated control xenografts). Moreover, an upward trend in necrosis with radiation, alone, was not statistically significant as shown by the graphical data presented in FIG. 42***c*, however, the combination of radiation and P-bi-TAT at 3 mg/kg resulted in an increase of necrosis of 65% and 70% at 10 mg/kg of (each $P<0.05$ vs. non-irradiated control). Moreover, FIG. 43** further demonstrates data showing the interactions between P-bi-TAT (3 and 10 mg/Kg, SC QD) and irradiation of pancreatic tumors at 1 and 5 Gy in comparison to controls.

Thus, based on the data provided in FIG. 42*a*-42*c*, it can be concluded that there is an unexpected combination therapy producing important additive effects on tumor weight reduction and on cell necrosis and viability. The anti-tumor effectiveness of the thyrointegrin antagonists, polymer conjugated thyrointegrin antagonists and bifunctional embodiments thereof, including the exemplary composition of P-bi-TAT on tumor mass at 3 mg/kg body weight is near maximal for the agent, i.e., results with dosages of 3 mg/kg and 10 mg/kg are comparable. The survey of histological changes obtained with and without radiation, however, suggests that 10 mg P-bi-TAT/kg was more effective than 3 mg/kg. The foregoing set of xenograft observations establish that the polymer conjugated thyrointegrin antagonists, such as P-bi-TAT are a highly effective therapeutic intervention in pancreatic carcinoma xenografts in the standard experimental context.

Example 10: Safety Studies, C57BL6 Mice

Preclinical toxicology of a representative of the polymer conjugated thyrointegrin antagonist antiangiogenic agent of P-bi-TAT was pursued in 5-to-6 week-old C57BL6 mice, treated for 14 days with varying doses of P-bi-TAT. The treatment groups were control (vehicle), 1 mg/kg, 3 mg/kg, 10 mg/kg, 30 mg/kg, 100 mg/kg and 330 mg/kg P-bi-TAT, administered daily s.c. for 14 days. Each treatment group consisted of 5 male and 5 female animals, and animal weights were measured twice weekly. Mice terminated after 14 days and blood samples collected from the retro-orbital venous plexus. Blood samples centrifuged, and harvested plasma was stored at −80° C. until subjected to analyses described below.

Figure 44:
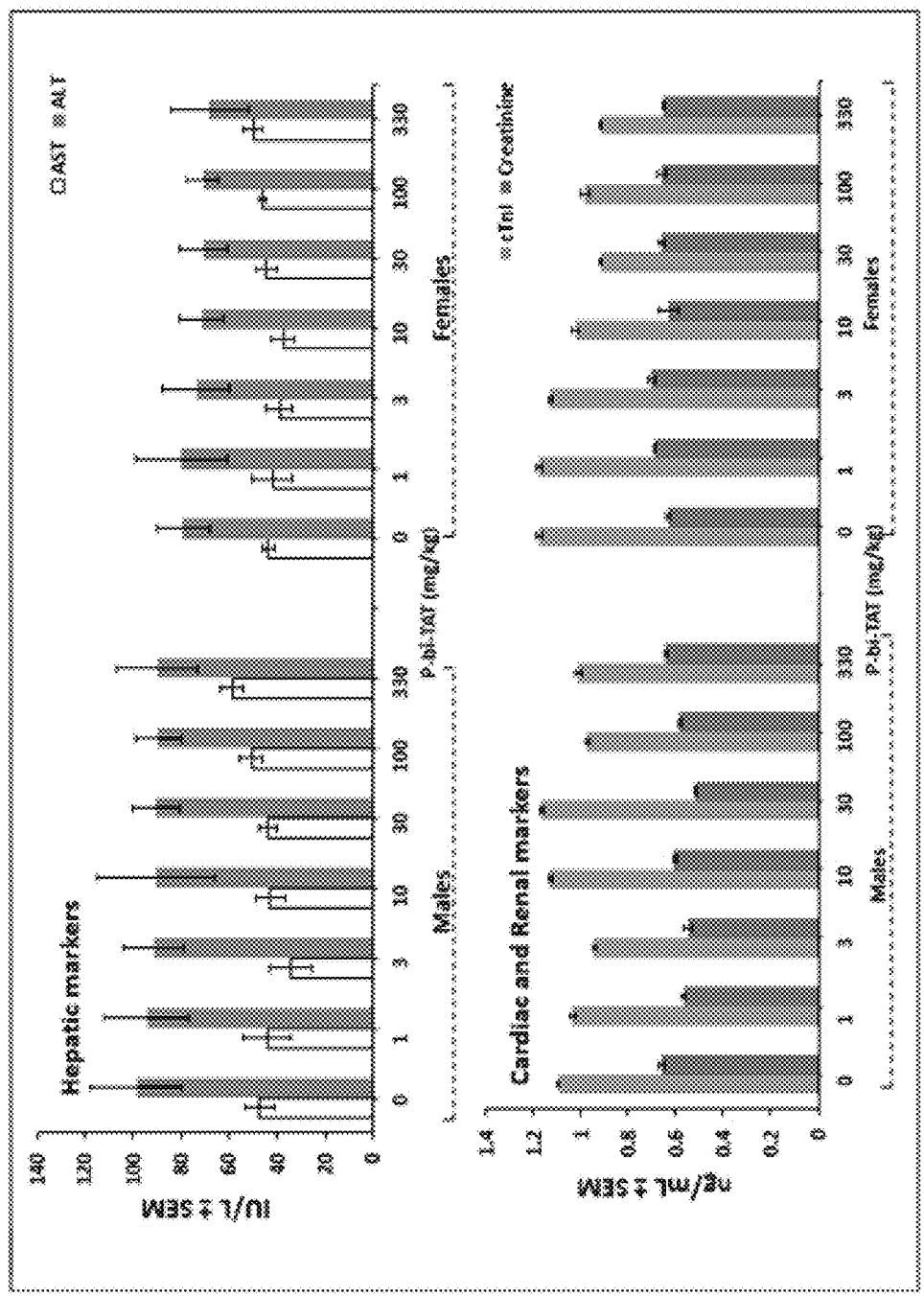
FIG. 44 depicts graphs describing Levels of hepatic, cardiac and renal markers in plasma of male and female mice treated with P-bi-TAT. Measurements in murine plasma of markers of liver damage (aspartate transaminase (AST) and alanine transaminase (ALT)), myocardial damage (cardiac troponin I (cTnI)) and renal function (creatinine) in mice treated daily for 14 days subcutaneously with P-bi-TAT in the concentrations (ng/mL) shown. Error bars represent standard error of the mean (S.E.M.).

Liver function was estimated by measurement in stored plasma of alanine transaminase (ALT) and aspartate transaminase (AST) activities (Colorimetric kit, Biovision, Inc., Milpitas, Calif.) the data for which is shown in FIG. 44. Cardiac troponin I (cTnI) levels in plasma were measured by an ELISA method (Life Diagnostics, West Chester, Pa.) as an index of myocardial damage (FIG. 44). It is a troponin found exclusively in the heart and not in other forms of muscle. Kidney function estimated by measurement of plasma creatinine concentration (Colorimetric kit, Biovision, Inc.) (FIG. 44). Satisfactory standard curves were constructed for each of the liver and kidney assays. Body weights were unaffected by the agent (results not shown). There was no evidence of liver, heart or kidney toxicity in male or female animals exposed for 2 weeks to as much as 100-fold the dose of P-bi-TAT that achieved maximal (3-10 mg/kg) anticancer therapeutic efficacy.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:
1. A composition comprising:
a general formula:

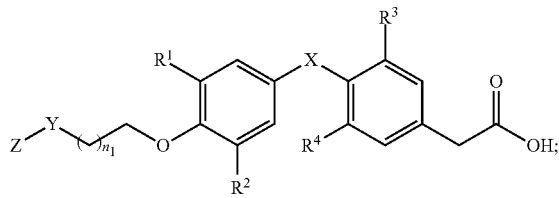

wherein $R^1$, $R^2$, $R^3$ and $R^4$ are each independently selected from the group consisting of hydrogen, iodine, linear alkanes and branched alkanes;
X is oxygen (O) or sulfur (S);
$n_1 \geq 0$;
Y=

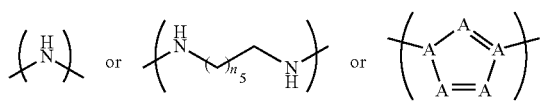

wherein $n_5$=1-5, and A=CH or N, with at least one A=N and
Z is a non-biodegradable polymer.
2. The composition of claim 1, wherein $n_1$ is 0, 1 or 2.
3. The composition of claim 1, wherein Y=

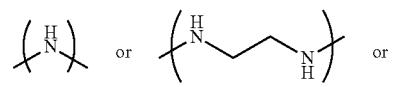

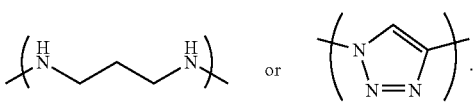

4. The composition of claim 1, wherein the non-biodegradable polymer, Z, is selected from the group consisting of polyethylene glycol (PEG), α-cyclodextrin, β-cyclodextrin, γ-cyclodextrin, alginic acid, chitosan and hyaluronic acid.
5. The composition of claim 1, wherein at least one of $R^1$, $R^2$, $R^3$ or $R^4$ is selected from the group consisting an isopropyl group, a tert-butyl group and a combination thereof.
6. The composition of claim 1, wherein the composition has a chemical formula of:

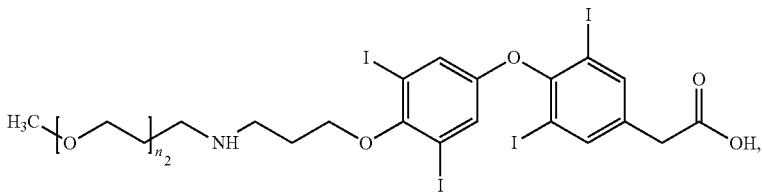

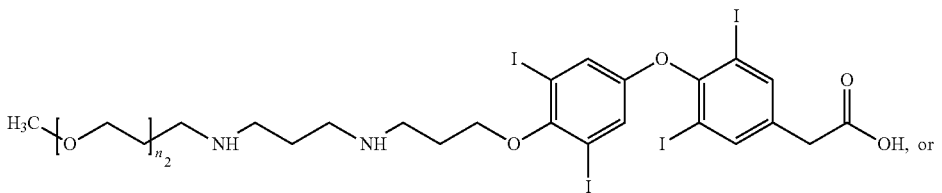

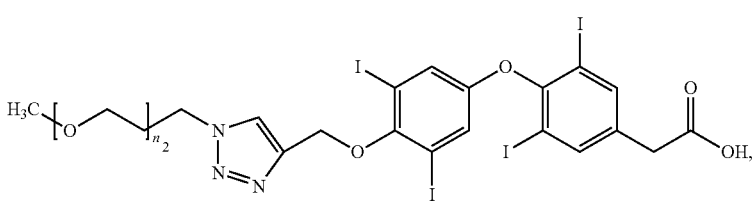

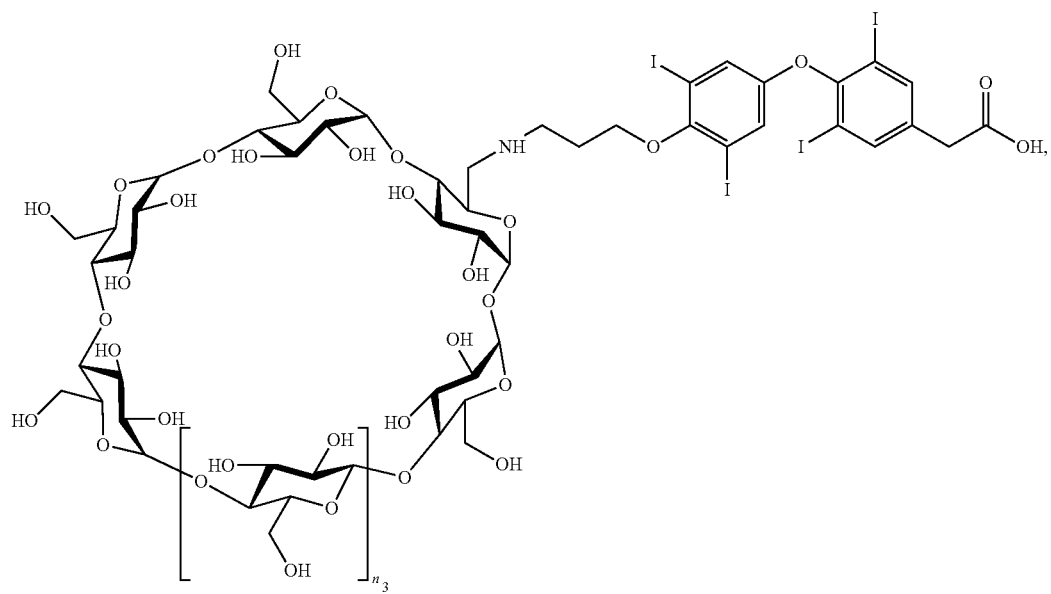
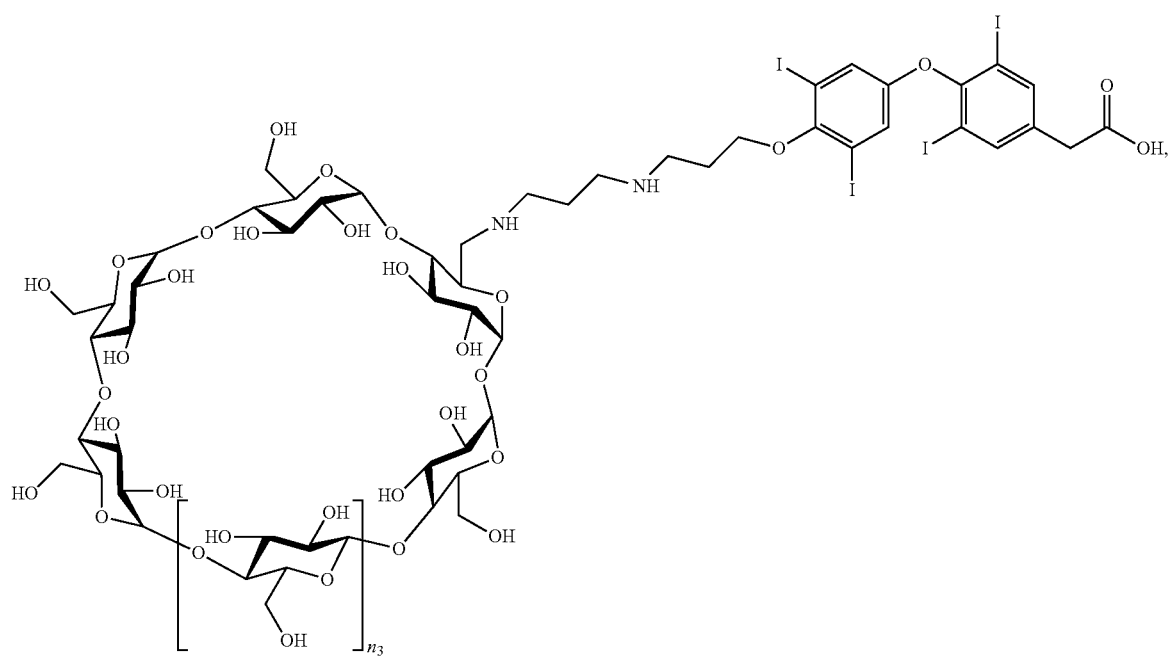

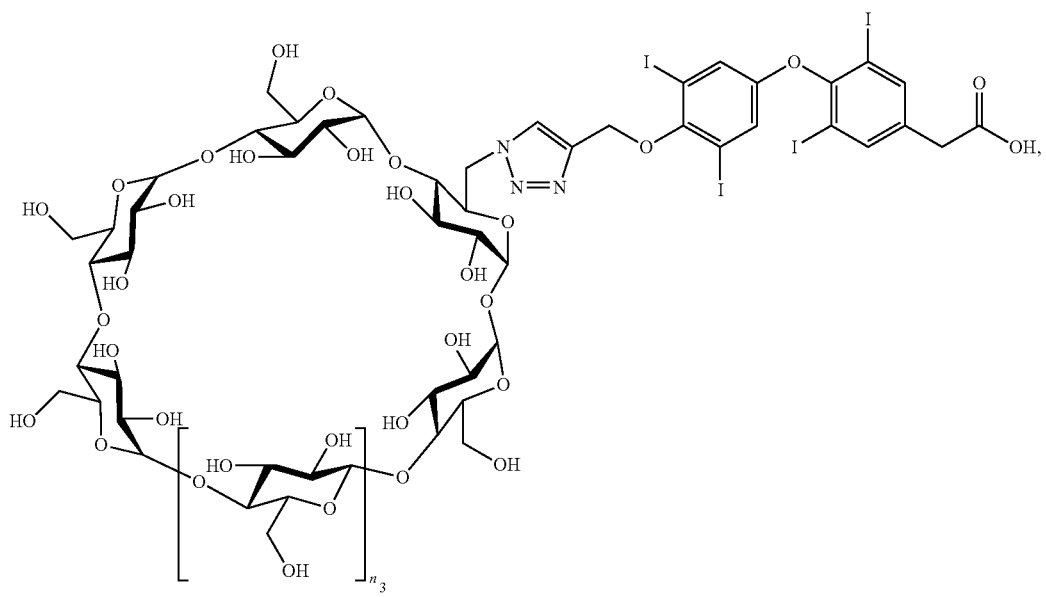
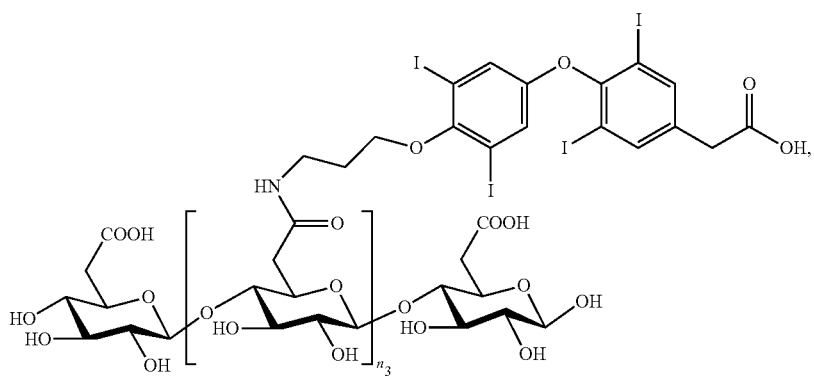
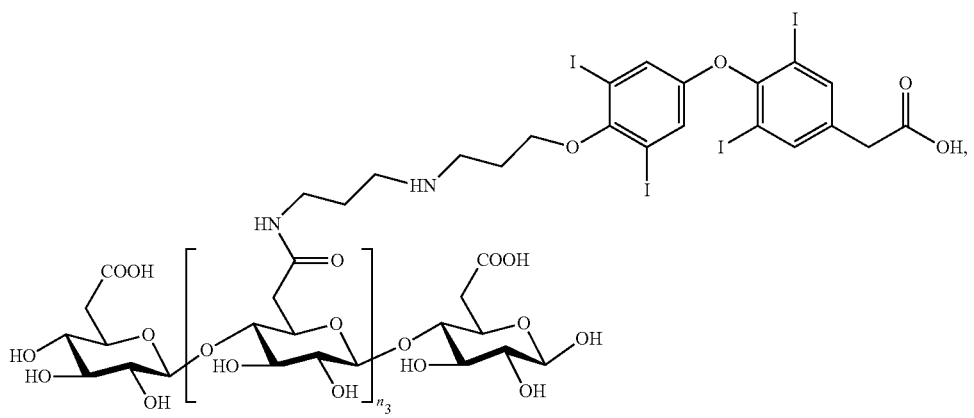

-continued
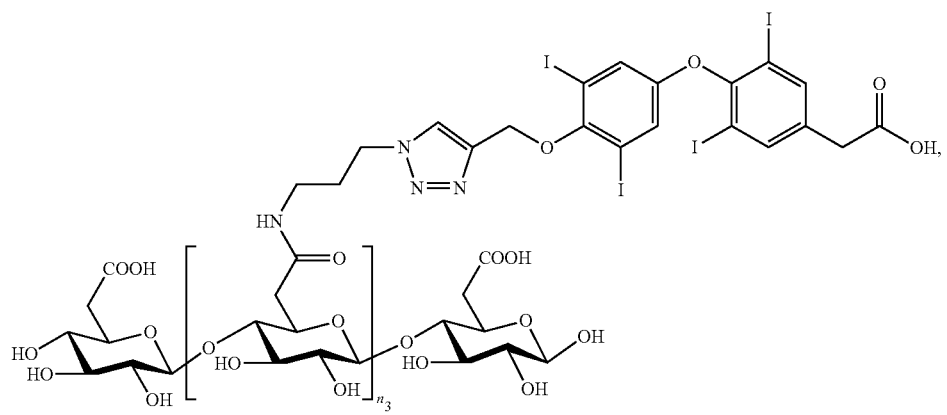
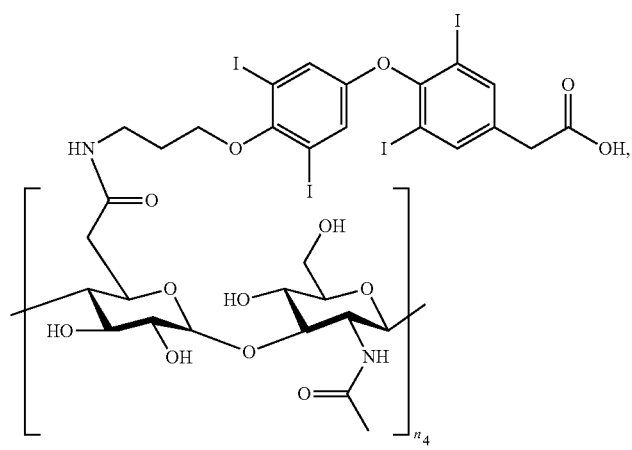
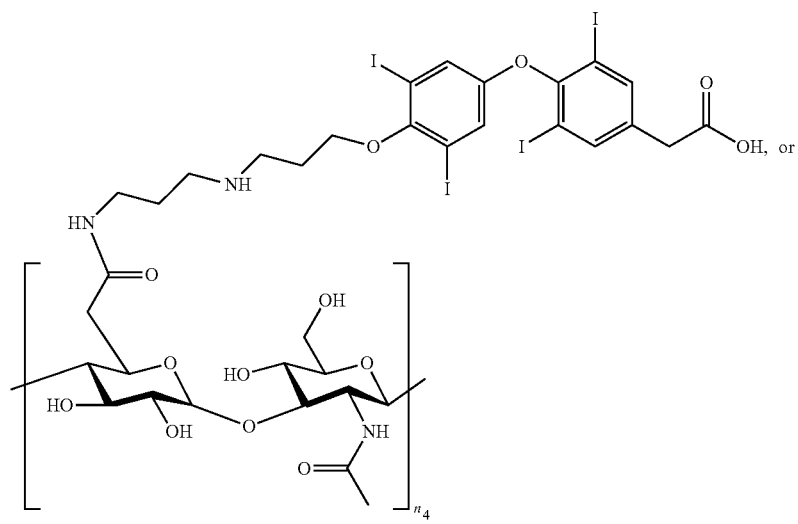

-continued

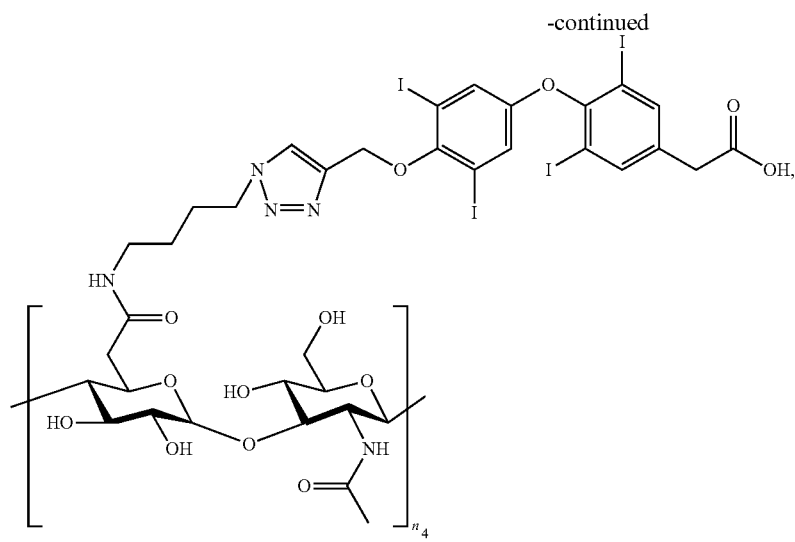

wherein $n_2$ is $\geq 1$, $n_3 = 1$, 2, or 3 and $n_4 \geq 1$.

7. A composition comprising:
a general formula:

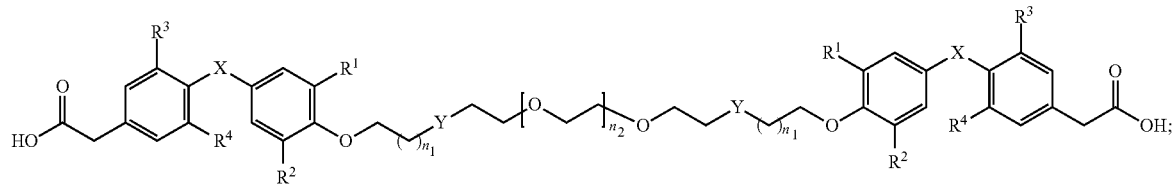

wherein $R^1$, $R^2$, $R^3$ and $R^4$ are each independently selected from the group consisting of hydrogen, iodine, linear alkanes and branched alkanes;
X is oxygen (O) or sulfur (S);
$n_1 \geq 0$;
$n_2 \geq 1$; and
Y=

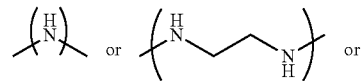

-continued

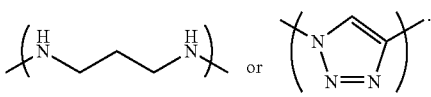

8. The composition of claim 7, wherein at least one of $R^1$, $R^2$, $R^3$ or $R^4$ is selected from the group consisting an isopropyl group, a tert-butyl group and a combination thereof.

9. The composition of claim 7, wherein the composition has a chemical formula of:

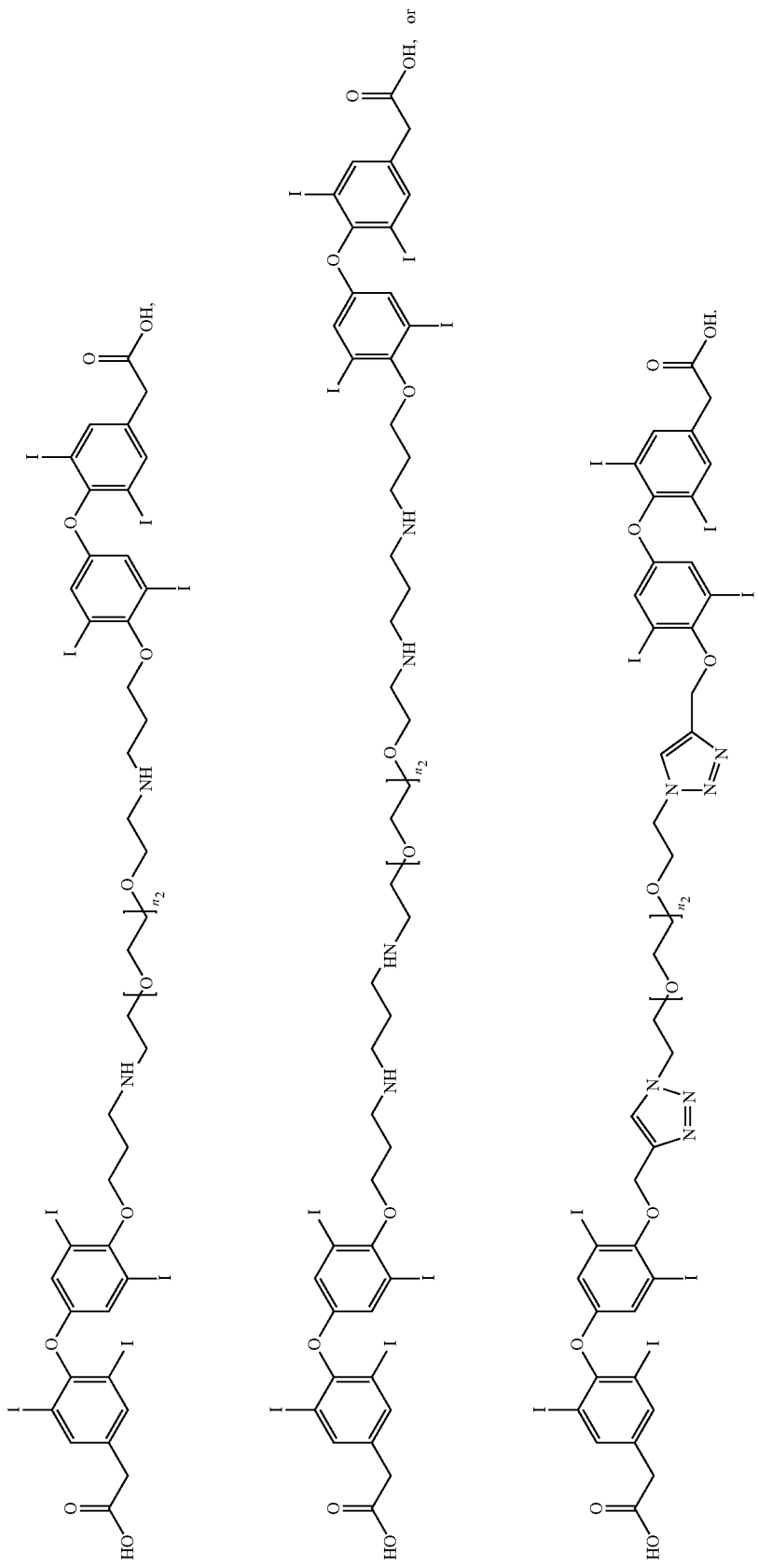

10. A composition comprising:
A thyroid antagonist;
a non-biodegradable polymer; and
a linker covalently bound to the thyroid antagonist and the non-biodegradable polymer via a non-cleavable covalent bond, wherein the linker comprises one of the following:

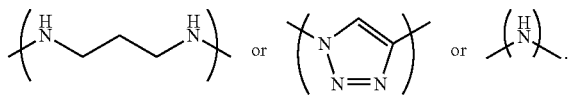

11. The composition of claim 10, wherein the thyroid antagonist is selected from the group consisting of tetraiodothyroacetic acid (tetrac), triiodothyroacetic acid (triac) and derivatives thereof.

12. The composition of claim 10, wherein the non-biodegradable polymer is selected from the group consisting of polyethylene glycol (PEG), α-cyclodextrin, β-cyclodextrin, γ-cyclodextrin, chitosan, alginic acid, hyaluronic acid and a combination thereof.

13. The composition of claim 10, wherein the composition is selected from the group consisting of PEG-diamino tetrac (P-DAT), PEG-monoamino tetrac (P-MAT), PEG-triazole tetrac (P-TAT), cyclodextrin bound diamino tetrac (C-DAT), cyclodextrin bound monoamino tetrac (C-MAT), cyclodextrin bound triazole tetrac (C-TAT), cyclodextrin bound P-DAT, cyclodextrin bound P-MAT, cyclodextrin bound P-TAT, chitosan bound diamino tetrac, chitosan bound monoamino tetrac, chitosan bound triazole tetrac, alginic acid-monoamino tetrac (A-MAT), alginic acid-diamino tetrac (A-DAT), alginic acid-triazole tetrac (A-TAT), hyaluronic acid-monoamino tetrac (H-MAT), hyaluronic acid-diamino tetrac (H-DAT) and hyaluronic acid-triazole tetrac (H-TAT).

14. The composition of claim 12 where the PEG is bi-functional or tetra-functional.

15. The composition of claim 14, wherein the composition is selected from the group consisting of PEG-bi-monoamino tetrac or triac (P-bi-MAT), PEG-bi-diamino tetrac or triac (P-bi-DAT), PEG-bi-triazole tetrac or triac (P-bi-TAT), PEG-tetra-monoamino tetrac (P-tetra-MAT), PEG-tetra-diamino tetrac or triac (P-tetra-DAT), PEG-tetra-triazole tetrac or triac (P-tetra-TAT) and derivatives thereof.

16. The composition of claim 1, wherein the composition have an anti-angiogenesis utility for the treatment of pathological angiogenesis associated disorders.

17. The composition of claim 16, wherein the pathological angiogenesis associated disorders include Cancer.

18. The composition of claim 17, where Cancer includes solid tumors and liquid cancer in humans or mammals.

19. The composition of claim 18, where solid tumors include Glioblastoma, pancreatic, ovarian, breast, prostate, bladder, lung, liver.

20. The composition of claim 18, where liquid cancer include acute myeloid leukemia, multiple myeloma, Lymphoma and chronic lymphocytic leukemia.

21. The composition of claim 16, wherein pathological angiogenesis associated disorders include Ocular vascular disorders, diabetic retinopathy, and age-Related Macular Degeneration.

22. The composition of claim 16, wherein pathological angiogenesis associated disorders include skin vascular disorders selected from the group consisting of Rosacea, Poikiloderma and Psoriasis.

23. The composition of claim 16, wherein pathological angiogenesis associated disorders include skin cancer.

* * * * *